(12) United States Patent
Adams et al.

(10) Patent No.: US 8,043,301 B2
(45) Date of Patent: Oct. 25, 2011

(54) VALVE LOADER METHOD, SYSTEM, AND APPARATUS

(75) Inventors: Martin Neal Adams, Seattle, WA (US); James Mark Kutsko, Carnation, WA (US); Desmond O'Connell, Lake Forest Park, WA (US)

(73) Assignee: Spiration, Inc., Redmond, WA (US)

( * ) Notice: Subject to any disclaimer, the term of this patent is extended or adjusted under 35 U.S.C. 154(b) by 107 days.

(21) Appl. No.: 12/422,179

(22) Filed: Apr. 10, 2009

(65) Prior Publication Data
US 2009/0292262 A1 Nov. 26, 2009

Related U.S. Application Data

(63) Continuation-in-part of application No. 12/249,243, filed on Oct. 10, 2008.

(60) Provisional application No. 60/979,690, filed on Oct. 12, 2007.

(51) Int. Cl.
*A61F 11/00* (2006.01)
*A61M 16/00* (2006.01)

(52) U.S. Cl. .................... 606/108; 128/207.14

(58) Field of Classification Search .......... 623/1.11, 623/1.12, 2.11, 23.68; 606/100, 108, 200; 600/139; 604/22, 529, 526, 523; 128/207.14, 128/207.16
See application file for complete search history.

(56) References Cited

U.S. PATENT DOCUMENTS

| | | | |
|---|---|---|---|
| 2,479,805 A | 8/1949 | Sabaratnam | |
| 2,832,078 A | 4/1958 | Williams | |
| 2,981,254 A | 4/1961 | Vanderbilt | |
| 3,320,972 A | 5/1967 | High et al. | |
| 3,370,305 A | 2/1968 | Goott et al. | |
| 3,445,916 A | 5/1969 | Schulte | |
| 3,472,230 A | 10/1969 | Forgarty | |
| 3,540,431 A | 11/1970 | Modin-Uddin | |
| 3,617,060 A | 11/1971 | Iezzi | |
| 3,657,744 A | 4/1972 | Ersek | |
| 3,671,979 A | 6/1972 | Moulopoulos | |
| 3,683,913 A | 8/1972 | Kurtz et al. | |
| 3,757,783 A | 9/1973 | Alley | |
| 3,760,808 A | 9/1973 | Bleuer | |
| 3,788,327 A | 1/1974 | Donowitz et al. | |

(Continued)

FOREIGN PATENT DOCUMENTS

AU 2002239759 5/2002

(Continued)

OTHER PUBLICATIONS

International Search Report Received in PCT/US2008/079650 Dated Jan. 30, 2009.

(Continued)

*Primary Examiner* — Julian Woo
(74) *Attorney, Agent, or Firm* — Knobbe, Martens, Olson & Bear, LLP

(57) ABSTRACT

A valve loading system is provided that uses a valve loader to transfer a valve or other medical device from a storage cartridge into a deployment catheter. The valve or other medical device can be implanted or positioned within a patient using the catheter after the valve or other medical device has been compressed and loaded into the catheter using the valve loader. The process then can be repeated by using the valve loading system to load or introduce another valve or other medical device into the catheter.

10 Claims, 32 Drawing Sheets

U.S. PATENT DOCUMENTS

| | | | |
|---|---|---|---|
| 3,874,388 A | 4/1975 | King et al. | |
| 4,014,318 A | 3/1977 | Dockum et al. | |
| 4,040,428 A | 8/1977 | Clifford | |
| 4,056,854 A | 11/1977 | Boretos et al. | |
| 4,084,268 A | 4/1978 | Ionescu et al. | |
| 4,086,665 A | 5/1978 | Poirlier | |
| 4,212,463 A | 7/1980 | Repinski et al. | |
| 4,218,782 A | 8/1980 | Rygg | |
| 4,222,126 A | 9/1980 | Boretos et al. | |
| 4,250,873 A | 2/1981 | Bonnet | |
| 4,301,810 A | 11/1981 | Belman | |
| 4,302,854 A | 12/1981 | Runge | |
| 4,339,831 A | 7/1982 | Johnson | |
| RE31,040 E | 9/1982 | Possis | |
| 4,403,616 A | 9/1983 | King | |
| 4,456,016 A | 6/1984 | Nowacki et al. | |
| 4,512,338 A | 4/1985 | Balko et al. | |
| 4,533,137 A | 8/1985 | Sonne | |
| 4,569,674 A | 2/1986 | Phillips et al. | |
| 4,582,058 A | 4/1986 | Depel et al. | |
| 4,619,246 A | 10/1986 | Molgaard-Nielsen et al. | |
| 4,681,110 A | 7/1987 | Wiktor | |
| 4,710,192 A | 12/1987 | Liotta et al. | |
| 4,732,152 A | 3/1988 | Wallsten et al. | |
| 4,759,758 A | 7/1988 | Gabbay | |
| 4,795,449 A | 1/1989 | Schneider et al. | |
| 4,808,183 A | 2/1989 | Panje | |
| 4,819,664 A | 4/1989 | Nazari | |
| 4,822,354 A | 4/1989 | Elosegui | |
| 4,830,003 A * | 5/1989 | Wolff et al. | 623/1.11 |
| 4,832,680 A | 5/1989 | Haber et al. | |
| 4,846,836 A | 7/1989 | Reich | |
| 4,850,999 A | 7/1989 | Planck | |
| 4,852,568 A | 8/1989 | Kensey | |
| 4,877,025 A | 10/1989 | Hanson | |
| 4,908,028 A | 3/1990 | Colon et al. | |
| 4,934,999 A | 6/1990 | Bader | |
| 4,936,823 A | 6/1990 | Colvin et al. | |
| 4,968,294 A | 11/1990 | Salama | |
| 4,973,047 A | 11/1990 | Norell | |
| 4,979,505 A | 12/1990 | Cox | |
| 4,984,581 A | 1/1991 | Stice | |
| 5,033,312 A | 7/1991 | Stupecky | |
| 5,038,621 A | 8/1991 | Stupecky | |
| 5,059,208 A | 10/1991 | Coe et al. | |
| 5,061,274 A | 10/1991 | Kensey | |
| 5,078,739 A | 1/1992 | Martin | |
| 5,092,781 A | 3/1992 | Casciotti et al. | |
| 5,116,360 A | 5/1992 | Pinchuk et al. | |
| 5,116,564 A | 5/1992 | Jansen et al. | |
| 5,123,919 A | 6/1992 | Sauter et al. | |
| 5,135,488 A | 8/1992 | Foote et al. | |
| 5,151,105 A | 9/1992 | Kwan-Gett | |
| 5,158,548 A | 10/1992 | Lau et al. | |
| 5,161,524 A | 11/1992 | Evans | |
| 5,171,299 A | 12/1992 | Heitzmann et al. | |
| 5,197,980 A | 3/1993 | Gorshkov et al. | |
| 5,255,687 A | 10/1993 | McKenna | |
| 5,275,169 A | 1/1994 | Afromowitz et al. | |
| 5,283,063 A | 2/1994 | Freeman | |
| 5,300,050 A | 4/1994 | Everett, Jr. et al. | |
| 5,304,199 A | 4/1994 | Myers | |
| 5,306,234 A | 4/1994 | Johnson | |
| 5,314,473 A | 5/1994 | Godin | |
| 5,339,805 A | 8/1994 | Parker | |
| 5,342,298 A | 8/1994 | Michaels | |
| 5,352,240 A | 10/1994 | Ross | |
| 5,353,470 A | 10/1994 | Bartlett | |
| 5,358,518 A | 10/1994 | Camilli | |
| 5,366,478 A | 11/1994 | Brinkerhoff et al. | |
| 5,370,657 A | 12/1994 | Irie | |
| 5,382,261 A | 1/1995 | Palmaz | |
| 5,383,470 A | 1/1995 | Kolby | |
| 5,391,205 A | 2/1995 | Knight | |
| 5,392,775 A | 2/1995 | Adkins, Jr. et al. | |
| 5,398,844 A | 3/1995 | Zaslavsky | |
| 5,409,019 A | 4/1995 | Wilk | |
| 5,409,444 A | 4/1995 | Kensey et al. | |
| 5,411,507 A | 5/1995 | Heckele | |
| 5,411,552 A | 5/1995 | Andersen et al. | |
| 5,413,599 A | 5/1995 | Imachi et al. | |
| 5,415,660 A | 5/1995 | Campbell et al. | |
| 5,417,226 A | 5/1995 | Juma | |
| 5,421,325 A | 6/1995 | Cinberg et al. | |
| 5,445,626 A | 8/1995 | Gigante | |
| 5,453,090 A | 9/1995 | Martenez et al. | |
| 5,459,544 A | 10/1995 | Emura | |
| 5,484,444 A | 1/1996 | Braunschweiler et al. | |
| 5,486,154 A | 1/1996 | Kelleher | |
| 5,499,995 A | 3/1996 | Teirstein | |
| 5,500,014 A | 3/1996 | Quijano et al. | |
| RE35,225 E | 4/1996 | Herweck et al. | |
| 5,507,754 A | 4/1996 | Green et al. | |
| 5,507,797 A | 4/1996 | Suzuki | |
| 5,509,900 A | 4/1996 | Kirkman | |
| 5,514,153 A | 5/1996 | Bonutti et al. | |
| 5,549,626 A | 8/1996 | Miller et al. | |
| 5,549,628 A | 8/1996 | Cooper et al. | |
| 5,562,608 A | 10/1996 | Sekins et al. | |
| 5,562,641 A | 10/1996 | Flomenblit et al. | |
| 5,562,728 A | 10/1996 | Lazarus et al. | |
| 5,603,698 A | 2/1997 | Roberts et al. | |
| 5,607,469 A | 3/1997 | Frey | |
| 5,645,565 A | 7/1997 | Rudd et al. | |
| 5,647,857 A | 7/1997 | Andersen et al. | |
| 5,660,175 A | 8/1997 | Dayal | |
| 5,662,622 A * | 9/1997 | Gore et al. | 604/526 |
| 5,662,713 A | 9/1997 | Andersen et al. | |
| 5,669,933 A | 9/1997 | Simon et al. | |
| 5,676,671 A | 10/1997 | Inoue | |
| 5,683,451 A | 11/1997 | Lenker et al. | |
| 5,690,644 A | 11/1997 | Yurek et al. | |
| 5,693,089 A | 12/1997 | Inoue | |
| 5,697,968 A | 12/1997 | Rogers et al. | |
| 5,702,343 A | 12/1997 | Alferness | |
| 5,702,409 A | 12/1997 | Rayburn et al. | |
| 5,725,519 A | 3/1998 | Penner et al. | |
| 5,752,522 A | 5/1998 | Murphy | |
| 5,752,965 A | 5/1998 | Francis et al. | |
| 5,755,770 A | 5/1998 | Ravenscroft | |
| 5,763,979 A | 6/1998 | Mukherjee et al. | |
| 5,782,896 A | 7/1998 | Chen et al. | |
| 5,797,920 A | 8/1998 | Kim | |
| 5,797,960 A | 8/1998 | Stevens et al. | |
| 5,800,339 A | 9/1998 | Salama | |
| 5,803,078 A | 9/1998 | Brauner | |
| 5,810,837 A | 9/1998 | Hofmann et al. | |
| 5,817,101 A | 10/1998 | Fiedler | |
| 5,830,217 A | 11/1998 | Ryan | |
| 5,833,694 A | 11/1998 | Poncet | |
| 5,840,081 A | 11/1998 | Andersen et al. | |
| 5,851,232 A | 12/1998 | Lois | |
| 5,855,587 A | 1/1999 | Hyon | |
| 5,855,597 A | 1/1999 | Jayaraman | |
| 5,855,601 A | 1/1999 | Bessler et al. | |
| 5,865,724 A | 2/1999 | Palmer et al. | |
| 5,876,434 A | 3/1999 | Flomenblit et al. | |
| 5,876,445 A | 3/1999 | Andersen et al. | |
| 5,911,756 A | 6/1999 | Debry | |
| 5,925,063 A | 7/1999 | Khosravi | |
| 5,944,738 A | 8/1999 | Amplatz et al. | |
| 5,947,997 A | 9/1999 | Pavcnik et al. | |
| 5,954,636 A | 9/1999 | Schwartz et al. | |
| 5,954,766 A | 9/1999 | Zadno-Azizi et al. | |
| 5,957,949 A | 9/1999 | Leonhardt et al. | |
| 5,957,978 A | 9/1999 | Blom | |
| 5,972,009 A | 10/1999 | Fortier et al. | |
| 5,976,158 A | 11/1999 | Adams et al. | |
| 5,976,174 A | 11/1999 | Ruiz | |
| 5,984,965 A | 11/1999 | Knapp et al. | |
| 5,989,234 A | 11/1999 | Valerio et al. | |
| 6,003,517 A | 12/1999 | Sheffield et al. | |
| 6,007,575 A | 12/1999 | Samuels | |
| 6,009,614 A | 1/2000 | Morales | |
| 6,010,511 A | 1/2000 | Murphy | |
| 6,010,525 A | 1/2000 | Bonutti et al. | |
| 6,020,380 A | 2/2000 | Killian | |

| | | | |
|---|---|---|---|
| 6,027,525 A | 2/2000 | Suh et al. | |
| 6,045,560 A | 4/2000 | McKean et al. | |
| 6,051,022 A | 4/2000 | Cai et al. | |
| 6,062,575 A | 5/2000 | Mickel et al. | |
| 6,068,635 A | 5/2000 | Gianotti | |
| 6,068,638 A | 5/2000 | Makower | |
| 6,077,291 A | 6/2000 | Das | |
| 6,079,413 A | 6/2000 | Baran | |
| 6,083,141 A | 7/2000 | Hougen | |
| 6,083,255 A | 7/2000 | Laufer et al. | |
| 6,096,027 A | 8/2000 | Layne | |
| 6,099,551 A | 8/2000 | Gabbay | |
| 6,123,663 A | 9/2000 | Rebuffat | |
| 6,132,458 A | 10/2000 | Staehle et al. | |
| 6,135,729 A | 10/2000 | Aber | |
| 6,135,991 A | 10/2000 | Muni et al. | |
| 6,141,855 A | 11/2000 | Morales | |
| 6,146,357 A | 11/2000 | Addis | |
| 6,149,664 A | 11/2000 | Kurz | |
| 6,162,245 A | 12/2000 | Jayaraman | |
| 6,165,179 A | 12/2000 | Cathcart et al. | |
| 6,168,614 B1 | 1/2001 | Andersen et al. | |
| 6,168,617 B1 | 1/2001 | Blaeser et al. | |
| 6,174,307 B1 | 1/2001 | Daniel et al. | |
| 6,174,323 B1 | 1/2001 | Biggs | |
| 6,183,520 B1 | 2/2001 | Pintauro et al. | |
| 6,193,748 B1 | 2/2001 | Thompson et al. | |
| 6,200,333 B1 | 3/2001 | Laufer | |
| 6,203,551 B1 | 3/2001 | Wu | |
| 6,206,918 B1 | 3/2001 | Campbell et al. | |
| 6,210,338 B1 | 4/2001 | Afremov et al. | |
| 6,231,587 B1 | 5/2001 | Makower | |
| 6,231,589 B1 | 5/2001 | Wessman et al. | |
| 6,234,996 B1 | 5/2001 | Bagaoisan et al. | |
| 6,238,334 B1 | 5/2001 | Easterbrook, III et al. | |
| 6,240,615 B1 | 6/2001 | Kimes et al. | |
| 6,241,654 B1 | 6/2001 | Alferness | |
| 6,241,678 B1 | 6/2001 | Afremov et al. | |
| 6,241,758 B1 | 6/2001 | Cox | |
| 6,242,472 B1 | 6/2001 | Sekins et al. | |
| 6,245,102 B1 | 6/2001 | Jayaraman | |
| 6,258,100 B1 | 7/2001 | Alferness et al. | |
| 6,264,700 B1 | 7/2001 | Kilcoyne et al. | |
| 6,267,775 B1 | 7/2001 | Clerc et al. | |
| 6,270,527 B1 | 8/2001 | Campbell et al. | |
| 6,287,290 B1 | 9/2001 | Perkins et al. | |
| 6,287,334 B1 | 9/2001 | Moll et al. | |
| 6,293,951 B1 | 9/2001 | Alferness et al. | |
| 6,299,604 B1 | 10/2001 | Ragheb et al. | |
| 6,302,893 B1 | 10/2001 | Limon et al. | |
| 6,312,407 B1 | 11/2001 | Zadno-Azizi et al. | |
| 6,325,777 B1 | 12/2001 | Zadno-Azizi et al. | |
| 6,325,778 B1 | 12/2001 | Zadno-Azizi et al. | |
| 6,327,505 B1 | 12/2001 | Medhkour et al. | |
| 6,327,772 B1 | 12/2001 | Zadno-Azizi et al. | |
| 6,328,689 B1 | 12/2001 | Gonzalez et al. | |
| 6,338,728 B1 | 1/2002 | Valerio et al. | |
| 6,350,278 B1 | 2/2002 | Lenker et al. | |
| 6,355,014 B1 | 3/2002 | Zadno-Azizi et al. | |
| 6,398,775 B1 | 6/2002 | Perkins et al. | |
| 6,402,754 B1 | 6/2002 | Gonzalez | |
| 6,416,554 B1 | 7/2002 | Alferness et al. | |
| 6,425,916 B1 | 7/2002 | Garrison et al. | |
| 6,428,561 B1 | 8/2002 | Johansson-Ruden et al. | |
| 6,439,233 B1 | 8/2002 | Geertsema | |
| 6,440,164 B1 | 8/2002 | DiMatteo et al. | |
| 6,447,530 B1 | 9/2002 | Ostrovsky et al. | |
| 6,454,754 B1 | 9/2002 | Frank | |
| 6,458,076 B1 | 10/2002 | Pruitt | |
| 6,458,153 B1 | 10/2002 | Bailey et al. | |
| 6,471,718 B1 | 10/2002 | Staehle et al. | |
| 6,471,979 B2 | 10/2002 | New et al. | |
| 6,485,407 B2 | 11/2002 | Alferness et al. | |
| 6,488,673 B1 | 12/2002 | Laufer | |
| 6,491,706 B1 | 12/2002 | Alferness et al. | |
| 6,493,589 B1 | 12/2002 | Medhkour et al. | |
| 6,503,272 B2 | 1/2003 | Duerig et al. | |
| 6,510,846 B1 | 1/2003 | O'Rourke | |
| 6,514,290 B1 | 2/2003 | Loomas | |
| 6,527,761 B1 | 3/2003 | Soltesz et al. | |
| 6,540,782 B1 | 4/2003 | Snyders | |
| 6,544,192 B2 | 4/2003 | Starr et al. | |
| 6,544,291 B2 | 4/2003 | Taylor | |
| 6,558,429 B2 | 5/2003 | Taylor | |
| 6,568,387 B2 | 5/2003 | Davenport et al. | |
| 6,569,166 B2 | 5/2003 | Gonzalez | |
| 6,585,639 B1 | 7/2003 | Kotmel et al. | |
| 6,589,256 B2 | 7/2003 | Forber | |
| 6,592,594 B2 | 7/2003 | Rimbaugh et al. | |
| 6,599,311 B1 | 7/2003 | Biggs et al. | |
| 6,600,307 B2 | 7/2003 | Turski | |
| 6,610,043 B1 | 8/2003 | Ingenito | |
| 6,629,951 B2 | 10/2003 | Laufer et al. | |
| 6,632,243 B1 | 10/2003 | Zadno-Azizi et al. | |
| 6,634,363 B1 | 10/2003 | Danek et al. | |
| 6,638,285 B2 | 10/2003 | Gabbay | |
| 6,669,724 B2 | 12/2003 | Park et al. | |
| 6,673,070 B2 | 1/2004 | Edwards et al. | |
| 6,679,264 B1 | 1/2004 | Deem et al. | |
| 6,682,250 B2 | 1/2004 | Banks | |
| 6,682,520 B2 | 1/2004 | Ingenito | |
| 6,694,979 B2 | 2/2004 | Deem et al. | |
| 6,709,401 B2 | 3/2004 | Soltesz et al. | |
| 6,712,812 B2 | 3/2004 | Roschak et al. | |
| 6,716,208 B2 | 4/2004 | Humes | |
| 6,722,360 B2 | 4/2004 | Doshi | |
| 6,743,259 B2 | 6/2004 | Ginn | |
| 6,746,686 B2 | 6/2004 | Hughes et al. | |
| 6,749,606 B2 | 6/2004 | Keast et al. | |
| 6,749,658 B1 | 6/2004 | Seagren | |
| 6,840,952 B2 | 1/2005 | Saker et al. | |
| 6,849,049 B2 | 2/2005 | Starr et al. | |
| 6,849,084 B2 | 2/2005 | Rabkin et al. | |
| 6,860,847 B2 | 3/2005 | Alferness et al. | |
| 6,887,256 B2 | 5/2005 | Gilson | |
| 6,904,909 B2 | 6/2005 | Andreas et al. | |
| 6,911,028 B2 | 6/2005 | Shadduck | |
| 6,929,637 B2 | 8/2005 | Gonzalez et al. | |
| 6,941,950 B2 | 9/2005 | Wilson et al. | |
| 6,951,571 B1 | 10/2005 | Srivastava | |
| 6,955,675 B2 | 10/2005 | Jain | |
| 6,958,059 B2 | 10/2005 | Zadno-Azizi | |
| 6,958,076 B2 | 10/2005 | Acosta et al. | |
| 6,989,027 B2 | 1/2006 | Allen et al. | |
| 6,997,951 B2 | 2/2006 | Solem et al. | |
| 7,011,094 B2 * | 3/2006 | Rapacki et al. | 604/249 |
| 7,086,398 B2 | 8/2006 | Tanaka | |
| 7,100,616 B2 | 9/2006 | Springmeyer | |
| 7,141,046 B2 | 11/2006 | Perkins et al. | |
| 7,169,140 B1 * | 1/2007 | Kume | 604/529 |
| 7,175,644 B2 | 2/2007 | Cooper et al. | |
| 7,207,946 B2 | 4/2007 | Sirokman | |
| 7,252,086 B2 | 8/2007 | Tanaka | |
| 7,273,469 B1 | 9/2007 | Chan et al. | |
| 7,278,430 B2 | 10/2007 | Kumar | |
| 7,357,795 B2 | 4/2008 | Kaji et al. | |
| 7,412,977 B2 | 8/2008 | Fields et al. | |
| 7,422,584 B2 | 9/2008 | Loomas et al. | |
| 7,434,578 B2 | 10/2008 | Dillard et al. | |
| 7,476,203 B2 | 1/2009 | DeVore et al. | |
| 7,530,995 B2 | 5/2009 | Quijano et al. | |
| 7,533,671 B2 | 5/2009 | Gonzalez et al. | |
| 7,637,934 B2 | 12/2009 | Mangiardi et al. | |
| 7,691,151 B2 | 4/2010 | Kutsko | |
| 7,757,692 B2 | 7/2010 | Alferness et al. | |
| 7,798,974 B2 | 9/2010 | Sirokman | |
| 7,842,061 B2 | 11/2010 | Dillard et al. | |
| 7,854,228 B2 | 12/2010 | Wilson et al. | |
| 7,875,048 B2 | 1/2011 | Dillard et al. | |
| 7,887,585 B2 | 2/2011 | Gonzalez et al. | |
| 7,896,887 B2 | 3/2011 | Rimbaugh et al. | |
| 7,913,698 B2 | 3/2011 | Barry et al. | |
| 7,942,931 B2 | 5/2011 | Gonzalez et al. | |
| 2001/0001817 A1 | 5/2001 | Humes | |
| 2001/0010017 A1 | 7/2001 | Letac et al. | |
| 2001/0012949 A1 | 8/2001 | Forber | |
| 2001/0025132 A1 | 9/2001 | Alferness et al. | |
| 2001/0034518 A1 | 10/2001 | Edwards et al. | |

| | | |
|---|---|---|
| 2001/0037808 A1 | 11/2001 | Deem et al. |
| 2001/0041906 A1 | 11/2001 | Gonzalez |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0007831 A1 | 1/2002 | Davenport et al. |
| 2002/0029004 A1 | 3/2002 | Starr et al. |
| 2002/0052626 A1 | 5/2002 | Gilson |
| 2002/0062120 A1 | 5/2002 | Perkins et al. |
| 2002/0072730 A1 | 6/2002 | McGill et al. |
| 2002/0077564 A1 | 6/2002 | Campbell et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0091411 A1 | 7/2002 | Saker et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0123749 A1 | 9/2002 | Jain |
| 2002/0138135 A1 | 9/2002 | Duerig et al. |
| 2002/0147462 A1 | 10/2002 | Mair et al. |
| 2003/0013935 A1 | 1/2003 | Alferness et al. |
| 2003/0018327 A1 | 1/2003 | Truckai et al. |
| 2003/0018344 A1 | 1/2003 | Kaji et al. |
| 2003/0024527 A1 | 2/2003 | Ginn |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0070682 A1 | 4/2003 | Wilson et al. |
| 2003/0083671 A1 | 5/2003 | Rimbaugh et al. |
| 2003/0083730 A1 | 5/2003 | Stinson |
| 2003/0109869 A1 | 6/2003 | Shadduck |
| 2003/0125763 A1 | 7/2003 | McInnes |
| 2003/0127090 A1 | 7/2003 | Gifford et al. |
| 2003/0154988 A1 | 8/2003 | DeVore |
| 2003/0158515 A1 | 8/2003 | Gonzalez et al. |
| 2003/0167065 A1 | 9/2003 | Kumar |
| 2003/0181922 A1 | 9/2003 | Alferness |
| 2003/0183235 A1 | 10/2003 | Rimbaugh et al. |
| 2003/0195385 A1 | 10/2003 | DeVore |
| 2003/0199972 A1 | 10/2003 | Zadno-Azizi et al. |
| 2003/0212337 A1 | 11/2003 | Sirokman |
| 2003/0212412 A1 | 11/2003 | Dillard et al. |
| 2003/0216769 A1 | 11/2003 | Dillard et al. |
| 2003/0225445 A1 | 12/2003 | Derus |
| 2003/0228344 A1 | 12/2003 | Fields et al. |
| 2004/0010209 A1 | 1/2004 | Sirokman |
| 2004/0024356 A1 | 2/2004 | Tanaka |
| 2004/0039250 A1 | 2/2004 | Tholfsen et al. |
| 2004/0039443 A1 | 2/2004 | Solem et al. |
| 2004/0040555 A1 | 3/2004 | Tanaka |
| 2004/0059263 A1 | 3/2004 | DeVore |
| 2004/0102248 A1 | 5/2004 | Young et al. |
| 2004/0127912 A1 | 7/2004 | Rabkin et al. |
| 2004/0143282 A1 | 7/2004 | Dillard et al. |
| 2004/0167636 A1 | 8/2004 | Dillard et al. |
| 2004/0194780 A1 | 10/2004 | Doshi |
| 2004/0206349 A1 | 10/2004 | Alferness et al. |
| 2004/0210306 A1 | 10/2004 | Quijano et al. |
| 2004/0211412 A1 | 10/2004 | Alferness et al. |
| 2004/0211434 A1 | 10/2004 | Loomas et al. |
| 2004/0243140 A1 | 12/2004 | Alferness et al. |
| 2004/0244802 A1 | 12/2004 | Tanaka |
| 2005/0033310 A1 | 2/2005 | Alferness et al. |
| 2005/0033344 A1 | 2/2005 | Dillard et al. |
| 2005/0096721 A1 | 5/2005 | Mangin et al. |
| 2005/0137611 A1 | 6/2005 | Escudero et al. |
| 2005/0137714 A1 | 6/2005 | Gonzalez et al. |
| 2005/0145253 A1 | 7/2005 | Wilson et al. |
| 2005/0166925 A1 | 8/2005 | Wilson et al. |
| 2005/0222580 A1 | 10/2005 | Gifford, III et al. |
| 2005/0245894 A1 | 11/2005 | Zadno-Azizi |
| 2005/0267323 A1 | 12/2005 | Dorros et al. |
| 2006/0032497 A1 | 2/2006 | Doshi |
| 2006/0074382 A1 | 4/2006 | Gonzalez et al. |
| 2006/0155217 A1 | 7/2006 | DeVore et al. |
| 2006/0200076 A1 | 9/2006 | Gonzalez et al. |
| 2006/0206147 A1 | 9/2006 | DeVore et al. |
| 2006/0235432 A1 | 10/2006 | DeVore |
| 2006/0235467 A1 | 10/2006 | DeVore |
| 2006/0249164 A1 | 11/2006 | Springmeyer |
| 2006/0270940 A1 | 11/2006 | Tsukashima et al. |
| 2007/0185531 A1 | 8/2007 | Rimbaugh et al. |
| 2007/0209204 A1 | 9/2007 | Chase et al. |
| 2007/0221230 A1 | 9/2007 | Thompson et al. |
| 2007/0225747 A1 | 9/2007 | Perkins et al. |
| 2007/0232992 A1 | 10/2007 | Kutsko |
| 2007/0250022 A1 | 10/2007 | Sirokman |
| 2008/0015627 A1 | 1/2008 | DeVore |
| 2008/0119866 A1 | 5/2008 | Alferness |
| 2008/0132989 A1 | 6/2008 | Snow et al. |
| 2009/0099530 A1 | 4/2009 | Adams et al. |
| 2009/0182369 A1 | 7/2009 | Gonzalez et al. |
| 2009/0205667 A1 | 8/2009 | Alferness et al. |
| 2009/0292262 A1 | 11/2009 | Adams et al. |
| 2010/0256714 A1 | 10/2010 | Springmeyer |
| 2010/0262071 A1 | 10/2010 | Kutsko et al. |
| 2011/0054632 A1 | 3/2011 | Alferness |
| 2011/0079221 A1 | 4/2011 | Dillard |

FOREIGN PATENT DOCUMENTS

| | | |
|---|---|---|
| AU | 2004263132 | 10/2010 |
| CA | 2308186 | 5/1999 |
| CA | 2375752 | 1/2001 |
| CA | 2401331 | 3/2001 |
| CA | 2408923 | 11/2001 |
| CN | 101868199 | 10/2010 |
| DE | 100 04 979 | 8/2000 |
| EP | 0 665 029 | 8/1995 |
| EP | 0 743 071 | 11/1996 |
| EP | 1 151 729 | 11/2001 |
| EP | 1 157 663 | 11/2001 |
| EP | 1 206 276 | 5/2002 |
| EP | 1 198 269 | 10/2009 |
| EP | 03 716 212 | 12/2010 |
| GB | 2 082 071 | 3/1982 |
| GB | 2 324 729 | 11/1998 |
| GB | 2 348 138 | 9/2000 |
| JP | 58-163332 | 9/1983 |
| JP | 60-10740 | 1/1994 |
| JP | 2003-503162 | 1/2003 |
| JP | 2004-535887 | 12/2004 |
| JP | 2005-527297 | 9/2005 |
| JP | 3742010 | 11/2005 |
| JP | 4387803 B2 | 10/2009 |
| JP | 2011-500171 | 1/2011 |
| RU | 2140211 | 10/1999 |
| SU | 852321 | 8/1981 |
| SU | 1371700 | 2/1988 |
| SU | 1593651 | 9/1990 |
| WO | WO 88/09683 | 12/1988 |
| WO | WO 94/26175 | 11/1994 |
| WO | WO 95/32018 | 11/1995 |
| WO | WO 96/34582 | 11/1996 |
| WO | WO 96/37167 | 11/1996 |
| WO | WO 97/09932 | 3/1997 |
| WO | WO 97/13471 | 4/1997 |
| WO | WO 97/27893 | 8/1997 |
| WO | WO 97/42871 | 11/1997 |
| WO | WO 97/44085 | 11/1997 |
| WO | WO 98/00840 | 1/1998 |
| WO | WO 98/01084 | 1/1998 |
| WO | WO 98/19633 | 5/1998 |
| WO | WO 98/39047 | 9/1998 |
| WO | WO 98/44854 | 10/1998 |
| WO | WO 98/48706 | 11/1998 |
| WO | WO 99/01076 | 1/1999 |
| WO | WO 99/13801 | 3/1999 |
| WO | WO 99/26692 | 6/1999 |
| WO | WO 99/32040 | 7/1999 |
| WO | WO 99/42059 | 8/1999 |
| WO | WO 99/42161 | 8/1999 |
| WO | WO 99/59503 | 11/1999 |
| WO | WO 99/64109 | 12/1999 |
| WO | WO 00/18329 | 4/2000 |
| WO | WO 00/27292 | 5/2000 |
| WO | WO 00/42950 | 7/2000 |

| | | |
|---|---|---|
| WO | WO 00/51500 | 9/2000 |
| WO | WO 00/51510 | 9/2000 |
| WO | WO 00/62699 | 10/2000 |
| WO | WO 00/78386 | 12/2000 |
| WO | WO 00/78407 | 12/2000 |
| WO | WO 01/02042 | 1/2001 |
| WO | WO 01/03641 | 1/2001 |
| WO | WO 01/03642 | 1/2001 |
| WO | WO 01/05334 | 1/2001 |
| WO | WO 01/10313 | 2/2001 |
| WO | WO 01/10314 | 2/2001 |
| WO | WO 01/12104 | 2/2001 |
| WO | WO 01/13839 | 3/2001 |
| WO | WO 01/13908 | 3/2001 |
| WO | WO 01/28433 | 4/2001 |
| WO | WO 01/30266 A | 5/2001 |
| WO | WO 01/37897 | 5/2001 |
| WO | WO 01/45590 | 6/2001 |
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | WO01/66190 | 9/2001 |
| WO | WO 01/66190 | 9/2001 |
| WO | WO 01/70114 | 9/2001 |
| WO | WO 01/74271 | 10/2001 |
| WO | WO 01/87170 | 11/2001 |
| WO | WO 01/89366 | 11/2001 |
| WO | WO 01/95786 | 12/2001 |
| WO | WO 02/05884 | 1/2002 |
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/056794 | 7/2002 |
| WO | WO 02/064045 | 8/2002 |
| WO | WO 02/064190 | 8/2002 |
| WO | WO 02/069823 | 9/2002 |
| WO | WO 02/094087 | 11/2002 |
| WO | WO 03/022124 | 3/2003 |
| WO | WO 03/030975 | 4/2003 |
| WO | WO 03/034927 | 5/2003 |
| WO | WO 03/034946 | 5/2003 |
| WO | WO 03/041779 | 5/2003 |
| WO | WO 03/047468 | 6/2003 |
| WO | WO 03/078579 | 9/2003 |
| WO | WO 03/079944 | 10/2003 |
| WO | WO 03/088820 | 10/2003 |
| WO | WO 03/094996 | 11/2003 |
| WO | WO 03/099164 | 12/2003 |
| WO | WO 2004/010845 | 5/2004 |
| WO | WO 2004/080347 | 9/2004 |
| WO | WO 2005/013835 | 2/2005 |
| WO | WO 2007/123690 | 11/2007 |
| WO | WO 2009/049261 | 4/2009 |
| WO | WO 2009/135070 | 11/2009 |
| WO | WO 2010/118056 | 10/2010 |

OTHER PUBLICATIONS

International Preliminary Report on Patentability for PCT/US2008/079650 mailed Dec. 23, 2009.
International Search Report and Written Opinion for PCT/US2010/030131 mailed Jun. 18, 2010.
U.S. Appl. No. 11/417,738, filed May 3, 2006, Issued as 7,042,931 on May 17, 2011, and its ongoing prosecution history including without limitation Office Actions, Amendments, Remarks, and any other potentially relevant documents.
Amendment mailed Mar. 3, 2004 in response to Office Action dated Oct. 3, 2003 in the related copending U.S. Appl. No. 09/951,105.
Andre A. Kulisz, Autocath 100—Nonsurgical, Intraurethral Bladder Control Device for Urinary Incontinent and Urinary Retentive Women—Another Dr. Kulisz's Development, http://www.kulisz.com/autocath.htm, 2003, 3 pp.
Chest Drains, from webmaster@atroi.ed/cp., from website Mar. 21, 2002; pp. 1-3.
Chest Drains, from webmaster@surgical-tutor.org.uk; from Website on Mar. 21, 2002; pp. 1-3.
Dillard et al.,"Evaluation of a Nvel Intra-bronchial Valve Device to Produce Lung Volume Reduction," Poster show at conference in Jun. 2002.
EDO Certamics Products and Services, from webmaster@edocorp.com; from website on Mar. 21, 2002; pp. 1,2.
Ellis, James H., Balloon Catheter Occlusion of Bronchopleural Fistulae, May 7, 1981, AJR: 138, Jan. 1982, p. 157-159.
EWS Endobronchial Watanabe Spigots, Novatech, edited Apr. 17, 2002.
Exploring Chest Drain Options; from webmaster google.com; RNWeb: Continuing Education; from website on Mar. 21, 2002; pp. 1-6.
Harris et al., "The Experimental Production in Dogs of Emphysema with Associated Asthatic Syndrome by Means of an Interatracheal Ball Valve," J Exp Med 30:1919; 75-88.
Horiuchi et al: Three Cases of Intractable Pneumothorax Treated Sucessfully by Bronchial Embolization using Silicon; JJSB, 2001. pp. 25-30.
Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.
Jones et al: Closure of a Benign Broncho-Oesophageal Fistula by Endoscopic Injection of Bovine Collagen, Cyanocrylate Glue and Gelfoam; 1996, pp. 53-55 Aust. N. Z. J.. Surg.
Lewis et al, "Pulmonary Interstitial Emphysema: Selective Bronchial Occlusion with a Swan-Ganz Catheter." Archives of Disease in Childhood, 63:1988, 313-315.
Marco: Bubble Detector, from webmaster@marco.de, from Website on Mar. 21, 2002; pp. 1-3.
Matthew et al. "Selective Bronchial Obstruction for Treatment of Bullous Interstitial Emphysema," J. of Ped. 96:1980, 475-477.
Oasis Dry Suction Chest Drains; Instructions for Use; Atrium Medical Corporation, Hudson New Hampshire, on Mar. 27, 2002,pp. 1-4.
Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081.
Puhakka et al., "Acute Bronchial Obstruction: An Experimental Rabbit Model Study." Int. J. of Pediatric Otorhinolaryngology. 18:1989, 107-118.
SIII Control and Display Modules; from webmaster@stoeckert.de; from website on Mar. 21, 2002, pp-15.
Snider et al., "The Definition of Emphysema: Report of the National Heart Lung and Blood Institute, Division of Lung Diseases Workshop", Am. Ev. Respir. Dis., 132:182-185, 1985.
Tube Thorascostomy; from webmaster@merck.com/pubs/mmanual; from Website Mar. 21, 2003, pp. 1,2.
Understanding Chest Drainage; from webmaster@nursingceu.com; from website on Mar. 21, 2002; pp. 1-15.
Watanabe et al: Bronchial Embolization Using Dental Impression Material in a Case of Pyelo-bronchial Fistula with Candida Fungemia; 1991. Journal of the Japan Society for Bronchology, pp. 607-610.
International Search Report in International application No. PCT/US00/40701, mailed Jan. 25, 2001, 3 pp.
European Supplemental Search Report in European Appln. No. 00969008.2, dated Feb. 26, 2004, 5 pp.
International Search Report in International application No. PCT/US02/25555, mailed Mar. 19, 2003, 4 pp.
European Search Report in European Appln. No. 02759335.9, dated Jan. 31, 2007.
Extended European Search Report for EP 08 0205468, dated Jul. 28, 2009.
Canadian Office Action dated Apr. 28, 2009 for Canadian Application No. 2,459,702.
Canadian Office Action dated Mar. 9, 2010 for Canadian Application No. 2,459,702.
Canadian Office Action dated Dec. 14, 2010 for Canadian Application No. 2,459,702.
European Supplemental Search Report dated Nov. 19, 2009 for EP Application No. 03 71 0804.

European Examination Report dated Apr. 14, 2010 for EP Application No. 03 71 0804.
International Search Report of Jul. 7, 2003, Application No. PCT/US03/05968.
European Supplemental Search Report of Feb. 28, 2008, Application No. 03 716 212.0-1265.
European Office Action of Dec. 23, 2008, Application No. 03 716 212.0-1265.
European Office Action of Jun. 17, 2009, Application No. 03 716 212.0-1265.
European Office Action of Apr. 28, 2011, Application No. 10196887.3-1269.
European Office Action on May 6, 2011, Application No. 09739872.1.
European Office Action of Dec. 8, 2010, Application No. 09739872.1.
Australian Office Action of Oct. 29, 2007, Application No. 2003219927.
Canadian Office Action of Apr. 28, 2009, Application No. 2,479,805.
Japanese Office Action of Feb. 3, 2009, Application No. 2003-577779.
International Search Report dated Oct. 1, 2003 re PCT Application No. PCT/US2003/14868.
PCT Search Report and Written Opinion from corresponding PCT Application No. PCT/US2004/007721 dated Mar. 12, 2004.
PCT International Search Report from corresponding PCT Application No. PCT/US2007/007923, dated May 20, 2008 in 2 pages.
PCT Preliminary and Written Report from corresponding PCT Application No. PCT/US2007/007923, dated Sep. 30, 2008 in 7 pages.
Chinese Office Action dated Jun. 4, 2010 re CN Application No. 200780019455.6.
International Preliminary Report on Patentability for Application No. PCT/US2010/030131, dated Mar. 18, 2011.
International Search Report and Written Opinion for Application No. PCT/US2004/025458, mailed Nov. 30, 2004.
Russian Office Action, for App. No. 2008139081/14(050381), dated Nov. 24, 2010.
US Office Action of Feb. 8, 2006, U.S. Appl. No. 10/103,487, filed Mar. 3, 2002.
US Office Action of Jun. 14, 2005, U.S. Appl. No. 10/103,487, filed Mar. 3, 2002.
US Office Action of Mar. 22, 2007, U.S. Appl. No. 10/103,487, filed Mar. 3, 2002.
US Office Action of May 19, 2006, U.S. Appl. No. 10/103,487, filed Mar. 3, 2002.
US Office Action of Dec. 10, 2010, U.S. Appl. No. 11/880,090, filed Jul. 19, 2007.
US Office Action mailed Oct. 3, 2003 from related copending U.S. Appl. No. 09/951,105.

* cited by examiner

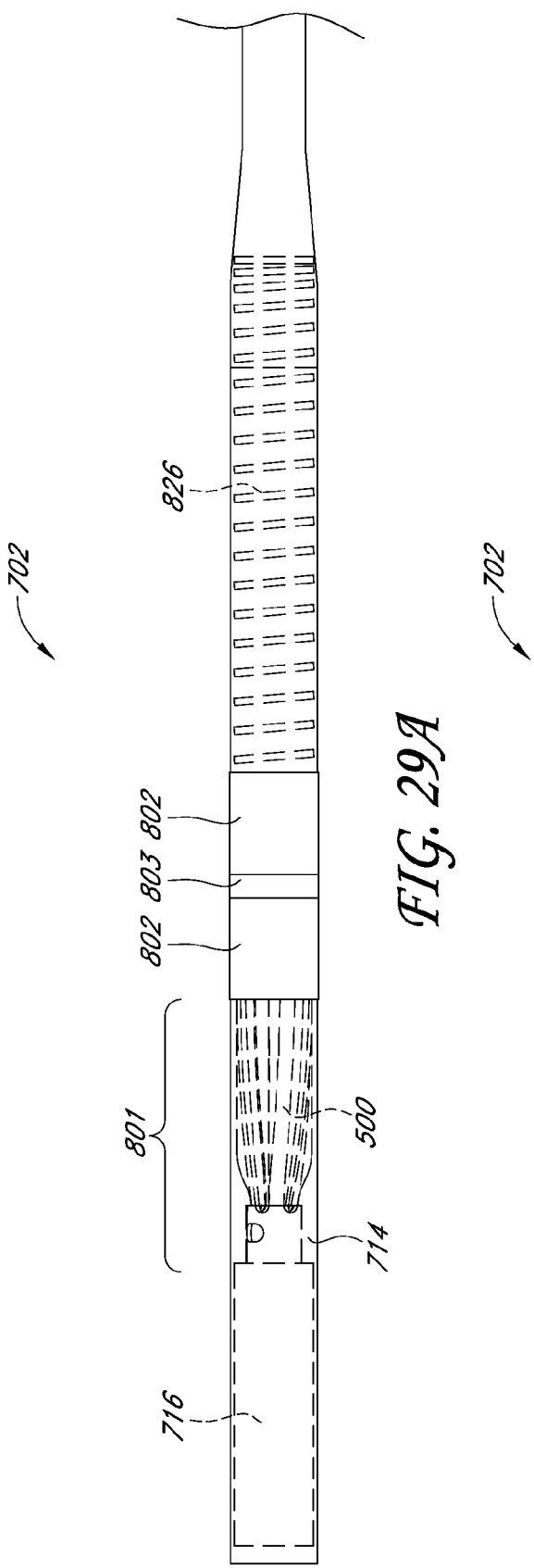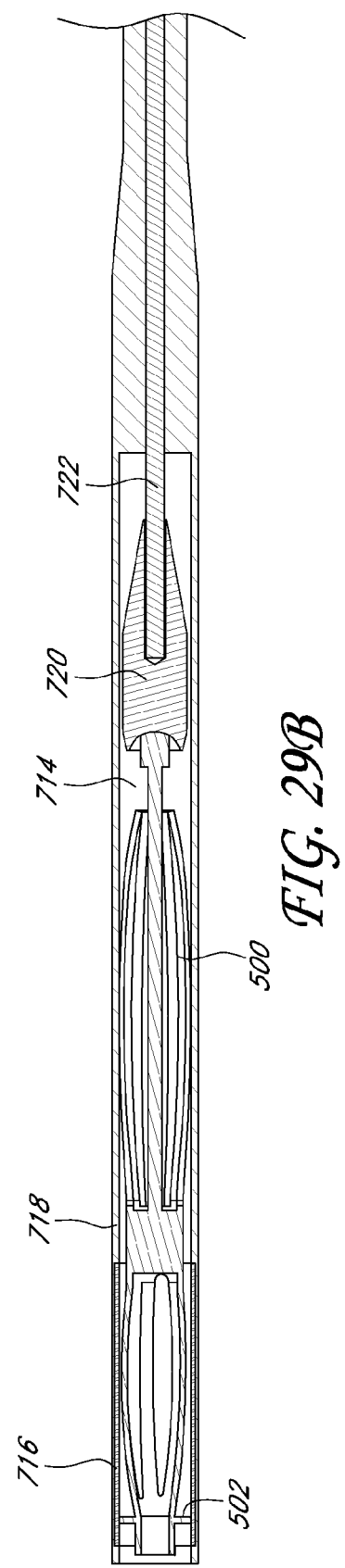

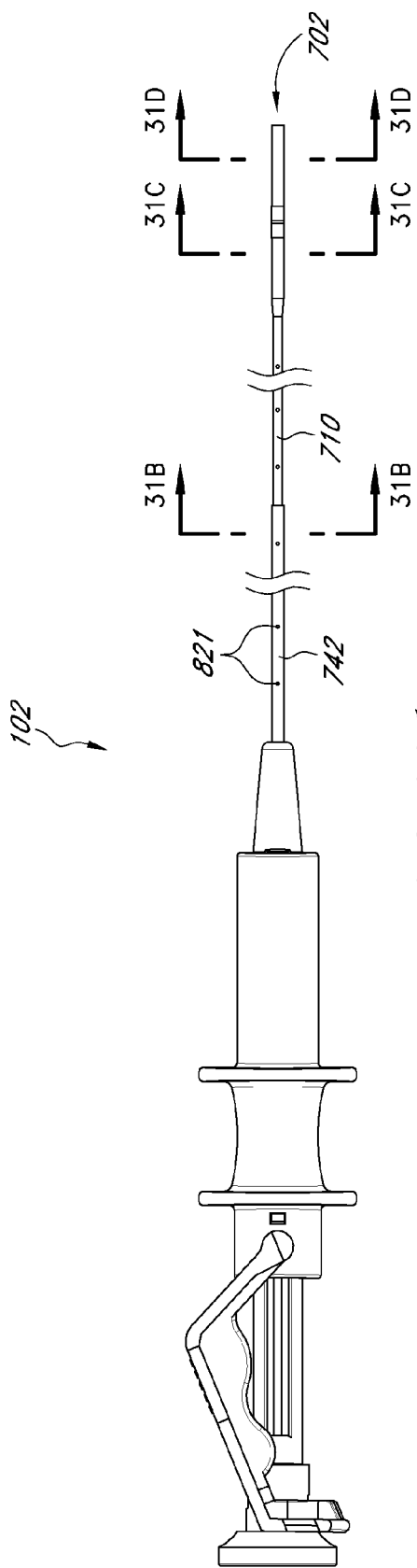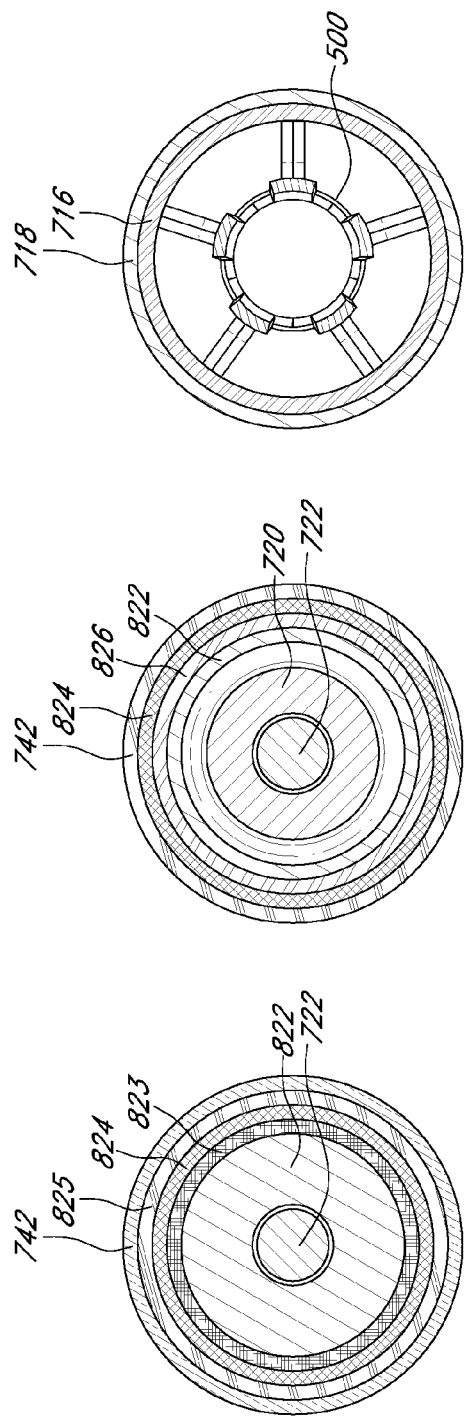
FIG. 31A
FIG. 31D
FIG. 31C
FIG. 31B

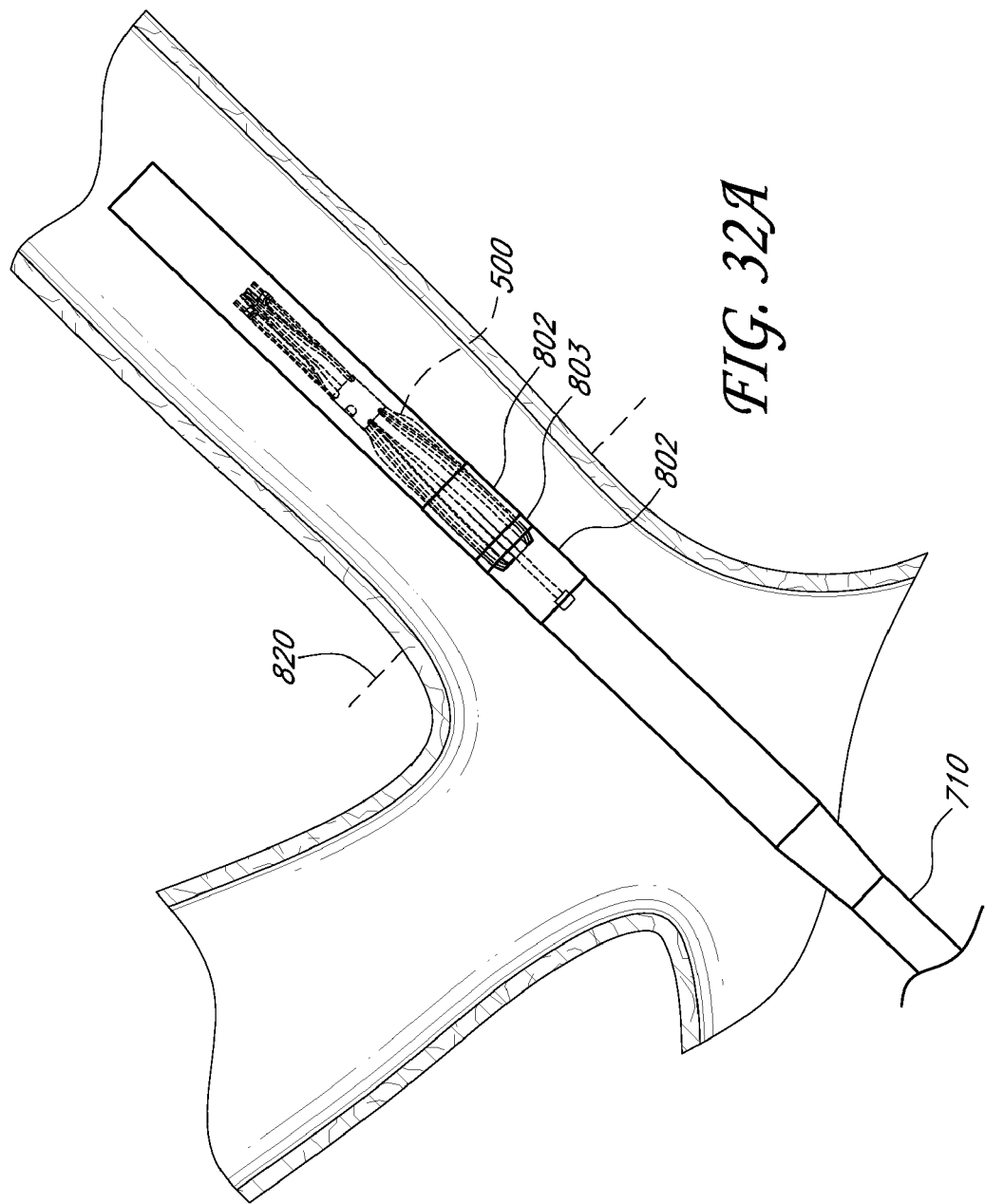

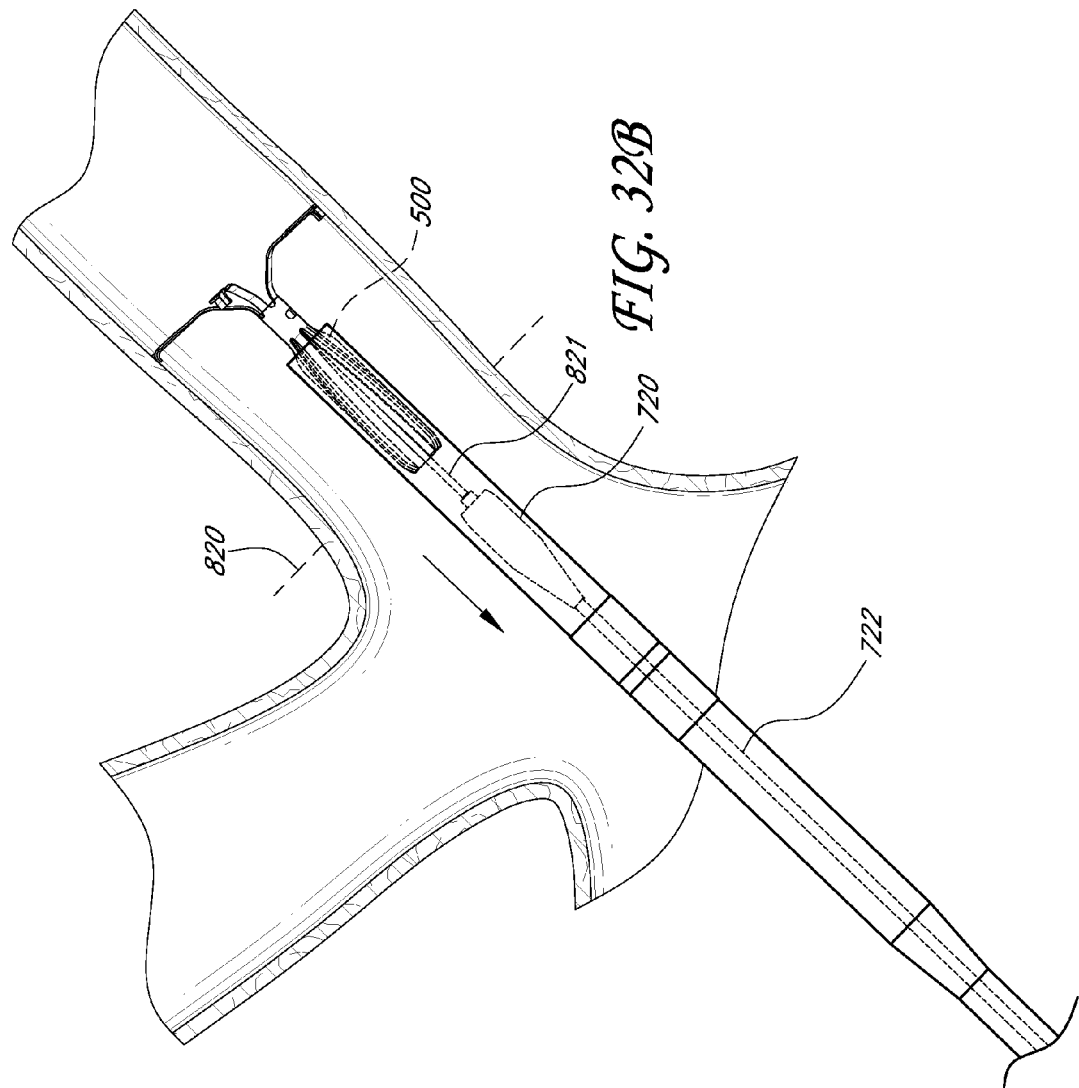

VALVE LOADER METHOD, SYSTEM, AND APPARATUS

CROSS-REFERENCE TO RELATED APPLICATIONS

This application claims the benefit of U.S. Provisional Application No. 60/979,690, titled VALVE LOADER SYSTEM, filed Oct. 12, 2007, which is hereby incorporated by reference in its entirety, and specifically with respect to the valve loading method, system, and apparatus disclosed therein. This application is also a continuation-in-part of U.S. patent application Ser. No. 12/249,243, titled VALVE LOADER METHOD, SYSTEM, AND APPARATUS, filed Oct. 10, 2008, which is hereby incorporated by reference in its entirety.

BACKGROUND OF THE INVENTION

1. Field of the Invention

Embodiments of the invention generally relate to the field of medical devices, and in particular, to methods, systems, and devices for loading or introducing into a catheter a valve or stent for implantation into a body.

2. Description of the Related Art

A catheter is a tube that can be inserted into a body, or body cavity, duct or vessel. A range of polymers are used for the construction of catheters, including but not limited to silicone, rubber, latex, polyurethane, Nylon, copolymers of polyurethane and polyether such as PEBAX®, and thermoplastic elastomers. Silicone is one of the most common choices because it is generally inert and generally not reactive to body fluids and a range of medical fluids with which it might come into contact. Catheters can be used to allow for drainage or injection of fluids to the body, or access into the body by surgical instruments and/or implantable devices. In order for a catheter to provide access to the body, the implantable device must be inserted into the catheter.

SUMMARY

Embodiments of the invention generally relate to loader devices, systems, and methods for loading and/or introducing into a catheter a valve or other medical device for implantation into a body. In certain embodiments, the medical devices, systems, and methods allow the catheter to be loaded or introduced with multiple valves or other medical devices.

In certain embodiments, a system for the sterile loading of a deployable medical device into a deployment apparatus comprises a housing comprising a cavity, the cavity configured to receive for receiving within a cavity of the housing at least one interchangeable medical device cartridge configured to house the deployable medical device therein, the housing further comprising an actuator or loader plunger configured to direct the deployable medical device from the at least one interchangeable medical device cartridge to a discharge end of said housing. The discharge end can be configured to receive the deployment apparatus into which the deployable medical device may be loaded.

In certain embodiments, the housing further comprises a funnel-shaped channel positioned between the cavity and the discharge end, the funnel-shaped channel configured to permit the passage of the deployable medical device therethrough when the actuator directs the deployable medical device from the at least one interchangeable medical device cartridge to the discharge end for loading into a deployment apparatus. In other embodiments, the system comprises the at least one interchangeable medical device medical device cartridge.

In certain embodiments, the at least one interchangeable medical device medical device cartridge comprises a tapered lumen for compressing the deployable medical device prior to loading into a deployment device. The actuator can comprise a plunger configured to engage the deployable medical device housed within the at least one interchangeable medical device cartridge. In certain embodiments, the housing further comprises a clamp configured to secure the deployment apparatus to the housing when it is desired to loading the deployable medical device into the deployment apparatus.

In certain embodiments, the housing can comprise a lock to prevent undesired release of the deployment apparatus prior to correct loading of the deployable medical device into the deployment apparatus. The housing can comprise a stop to signal the user that the actuator has traveled to the correct position for completely loading the deployable medical device into the deployment apparatus. In certain embodiments, the housing comprises a means for providing an audible sound or visual confirmation to signal the user that the actuator has traveled to the correct position for completely loading the deployable medical device into the deployment apparatus. The housing can also comprise a means for providing an audible sound or visual confirmation to signal the user that the deployment apparatus has been locked into the housing clamp and that loading may commence. In certain embodiments, the housing further comprises a safety apparatus to protect the actuator from being damaged by improper installation or removal of the at least one interchangeable medical device interchangeable cartridge within the cavity.

In certain embodiments, a kit for use in the storage, transport and loading of a deployable medical device into a deployment apparatus, the kit comprising the system described herein and may further comprise the deployment apparatus. The kit can further comprise a plurality of interchangeable medical device cartridges. The kit can comprise at least one of the interchangeable medical device cartridges contains a medical device having a size different from at least one other medical device within another of the interchangeable medical device cartridges.

In certain embodiments, a storage and transport cartridge comprising an enclosure for interchangeable use in a loading system, the enclosure configured to house a deployable medical device that may be directed by the loading system into a deployment apparatus.

In certain embodiments, a kit for use in loading a medical device into a deployment apparatus, the kit comprising the cartridge as described herein and a loading system into which the cartridge may be interchangeably inserted.

In certain embodiments, a method of loading a medical device into a deployment apparatus comprises inserting an interchangeable medical device cartridge into a loading system, the system comprising a housing comprising a cavity for receiving the interchangeable medical device cartridge, and activating an actuator within the loading system to direct a medical device within the interchangeable medical device cartridge through said loading system and into the deployment apparatus. For purposes of this summary, certain aspects, advantages, and novel features of the invention are described herein. It is to be understood that not necessarily all such aspects, advantages, and features may be employed and/or achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIGS. 29A-B are enlarged views of the distal end of an embodiment of the deployment catheter or other deployment apparatus.

FIG. 31A is a view of an embodiment of the deployment catheter. FIGS 31B-D represent sections taken at various positions along the deployment catheter. In FIG. 31C, the valve 500 has been removed for clarity.

FIGS. 32A-C are a sequence of illustrations depicting an embodiment of the deployment catheter deploying a valve into a lung passageway.

DETAILED DESCRIPTION OF THE EMBODIMENTS

Figure 1:
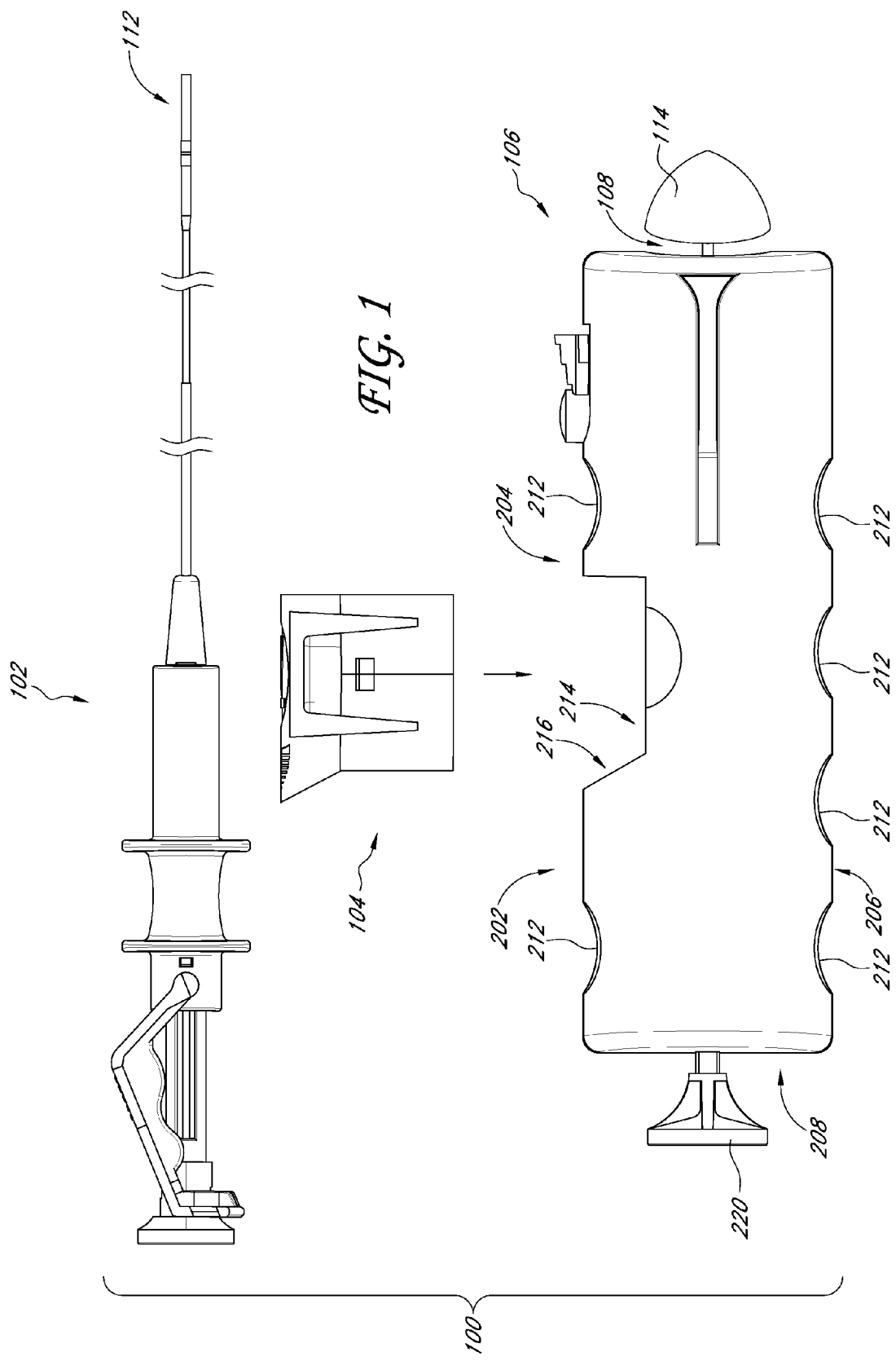
FIG. 1 is a system view of an embodiment of a valve loading system used for loading and/or introducing a valve or other medical device into a deployment catheter or other deployment apparatus.

A valve loading system and related components will now be described with reference to the accompanying figures of one or more embodiments. The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

The terms "valve," "deployable medical device," and "medical device" as used herein are broad interchangeable terms and, unless otherwise indicated, the terms can include within their meanings, without limitation, stents, valves, lung reduction valves, coils, filters, embolic protection devices, balloons, augmentation devices, probes, anchors, sponges, or any other medical device, deployable or otherwise, that is configured to be loaded or introduced into a catheter or other deployment apparatus. In certain embodiments, the valve and/or medical device is the type disclosed in U.S. Pat. No. 6,293,951 or in U.S. Patent Application Publication No. 2003-0050648, each of which is hereby incorporated in its entirety.

In certain embodiments, the valve loading system described herein can be configured to load valves or medical devices as small as about 5 mm, 6 mm, 7 mm, and 9 mm in diameter. The valve loading system, in certain embodiments, can be configured to compress or collapse valves or medical devices for deployment using a bronchoscope comprising a working channel diameter of about 2.0 mm or greater, for example, about 2.6 mm. In certain embodiments, the valve or medical device comprises a radiopaque material that is visible through a deployment catheter or other deployment apparatus, bronchoscope, or body.

The terms "body" and "patient" as used herein are broad interchangeable terms that generally refer to mammalian (human or animal) bodies, patients, organs, lumens, cavities, vessels, passageways, channels, or the like.

As discussed above, a valve or other medical device, deployable or otherwise, can be introduced into a catheter or other deployment apparatus using methods, systems, and devices described herein. In some embodiments, a valve loading system is provided that generally comprises, without limitation, a deployment catheter or other deployment apparatus, a valve loader, a valve-carrying cartridge (also referred to herein as a interchangeable medical device cartridge), and/or other components. The valve or other medical device can be implanted or positioned within a patient using the catheter or other deployment apparatus after the valve or other medical device has been loaded into the catheter or other deployment apparatus using the valve loader. In some embodiments, the process then can be repeated by using the valve loading system to load or introduce another valve or other medical device into the catheter (as used herein, the term "catheter" includes without limitation any other deployment apparatus).

FIG. 1 illustrates an embodiment of a valve loading system 100 that is arranged and configured in accordance with certain features, aspects and advantages of the present invention. The illustrated valve loading system 100 generally comprises, among other components, a deployment catheter 102, a cartridge 104, and a valve loader 106. The cartridge 104 carries, transports, and/or stores a valve or other medical device. In some configurations, the cartridge 104 is designed to store the valve or other medical device for limited or more extended periods of time. In some embodiments, the cartridge 104 is interchangeable with other cartridges. The valve loader can comprise a first open cavity 214 that accommodates the cartridge 104. With the cartridge 104 positioned in the cavity 214 and with a distal end 112 of the deployment catheter 104 positioned in a connection port 108, the valve or other medical device can be transferred from the cartridge 104 into the deployment catheter 102 using the valve loader 106. Thus, the illustrated valve loader 106 can be configured to provide sterile loading of the valve or other medical device into the deployment catheter 102.

The illustrated valve loader 106 comprises an outer housing structure 202. In some embodiments, the outer housing structure 202 is constructed of plastic, metal, or other like material. Preferably, the outer housing structure 202 is sized and configured for holding in a hand. In some embodiments, the outer housing structure 202 can have a length that easily allows for placement in a user's hand. For example, the outer housing structure 202 can be 5, 6, 7, or 8 inches in length, which will easily fit within a user's hand. The outer housing structure 202 can comprise a generally cylindrical shape or other suitable form to enhance the ergonomics and to provide for easy placement in or control by a human hand. In the illustrated configuration, the outer housing structure 202 comprises a flattened cylindrical shape. Other structures, materials, shapes, and sizes also are possible.

Figure 2:
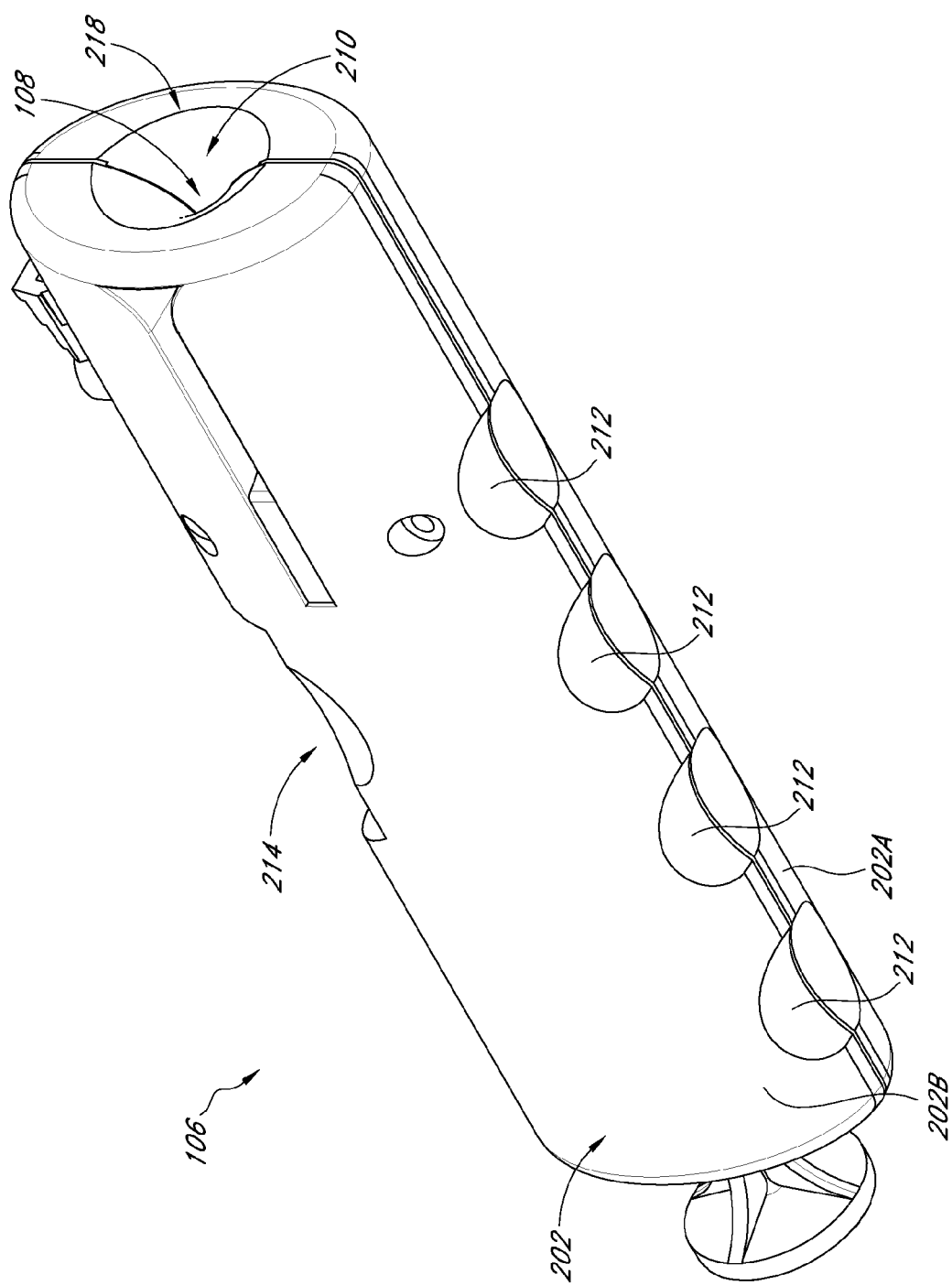
FIG. 2 is a perspective view of an embodiment of a valve loader of the system of FIG. 1, which valve loader is used for loading and/or introducing a valve or other medical device into a deployment catheter or other deployment apparatus.

As illustrated in FIG. 1 and FIG. 2, the housing structure 202 can have a top side 204, a bottom side 206, a proximal end 208, and a distal end 210. Any directional terms used herein are merely to provide a frame of reference and should not be considered to limit the scope of the claimed invention. As used herein, "distal" means toward the location in which the valve or other medical device will be deployed while "proximal" means toward the user of the component (e.g., toward the user of the valve loader 106).

The outer housing structure 202 preferably features a plurality of recesses 212 along the top and bottom sides 204, 206. The illustrated outer housing structure 202 comprises two recesses 212 along the top side 204 and four recesses 212 along the bottom side 206. In some embodiments, the two recesses 212 along the top side 204 are generally aligned with two of the four recesses 212 along the bottom side 206. Preferably, the two recesses 212 are positioned on opposite ends of the top side 204. More preferably, the two recesses 212 on the top side 204 are positioned with one of the two recesses 212 on each side of a first open cavity 214.

The first open cavity 214 can have any suitable configuration. In some embodiments, the first open cavity 214 comprises a substantially rectangular shape with an angled portion 216; however, other shapes and dimensions are possible. In certain embodiments, the shape and configuration of the first open cavity 214 corresponds to the outer shape and configuration of the cartridge 104 such that the cartridge 104 can be inserted into the first open cavity 214 in only one direction, orientation or position. In other words, the cavity 214 of the housing 202 can comprise a first shape and the cartridge 104 can comprise a complementary shape such that, when inserted into or coupled with the housing 202, the cartridge 104 is properly oriented for its intended use.

With reference to FIG. 1 and FIG. 2, the housing structure 202 can comprise the connection port 108 that is defined in part by a second open cavity 218 that can receive a distal end 112 of the deployment catheter 102 or another device, for example, a shipping lock 114. In some embodiments, the proximal end of the shipping lock 114 can be shaped and configured to closely correspond to the shape and configuration of the distal end 112 of the deployment catheter 102. While the illustrated housing structure 202 comprises the second open cavity 218, which comprises a funnel-type configuration that helps to receive the distal end 112 of the deployment catheter 102, the housing structure 202 can comprise a generally flat distal end 210 or a protruding distal end 210.

The housing structure 202 of the valve loader 106 can be constructed of two halves or sides 202A, 202B that are secured together in any suitable manner. In some configurations, the two portions 202A, 202B snap together and can be secured together with posts or the like. Preferably, one of the two portions 202B is considered a male portion while the other one of the two portions 202A is considered a female portion and the male and female portions can be joined together in any suitable manner.

Figure 3:
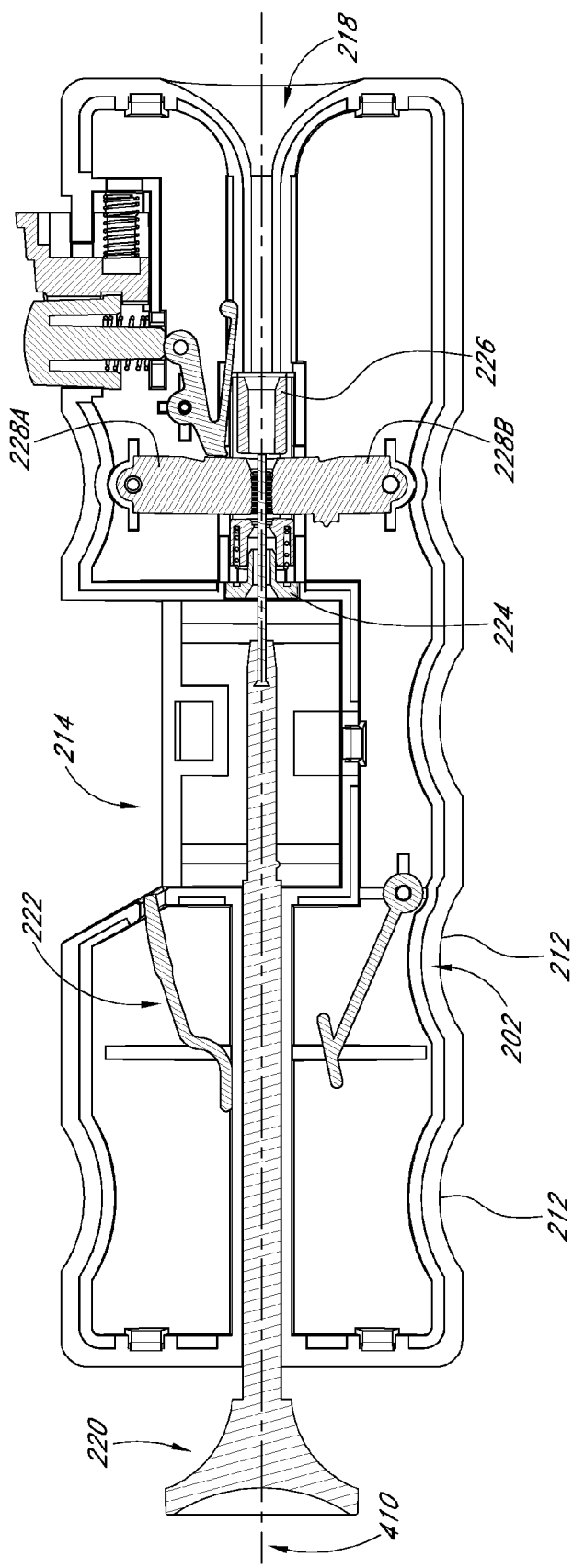
FIG. 3 is a sectioned view of the valve loader of FIG. 2.
Figure 4:
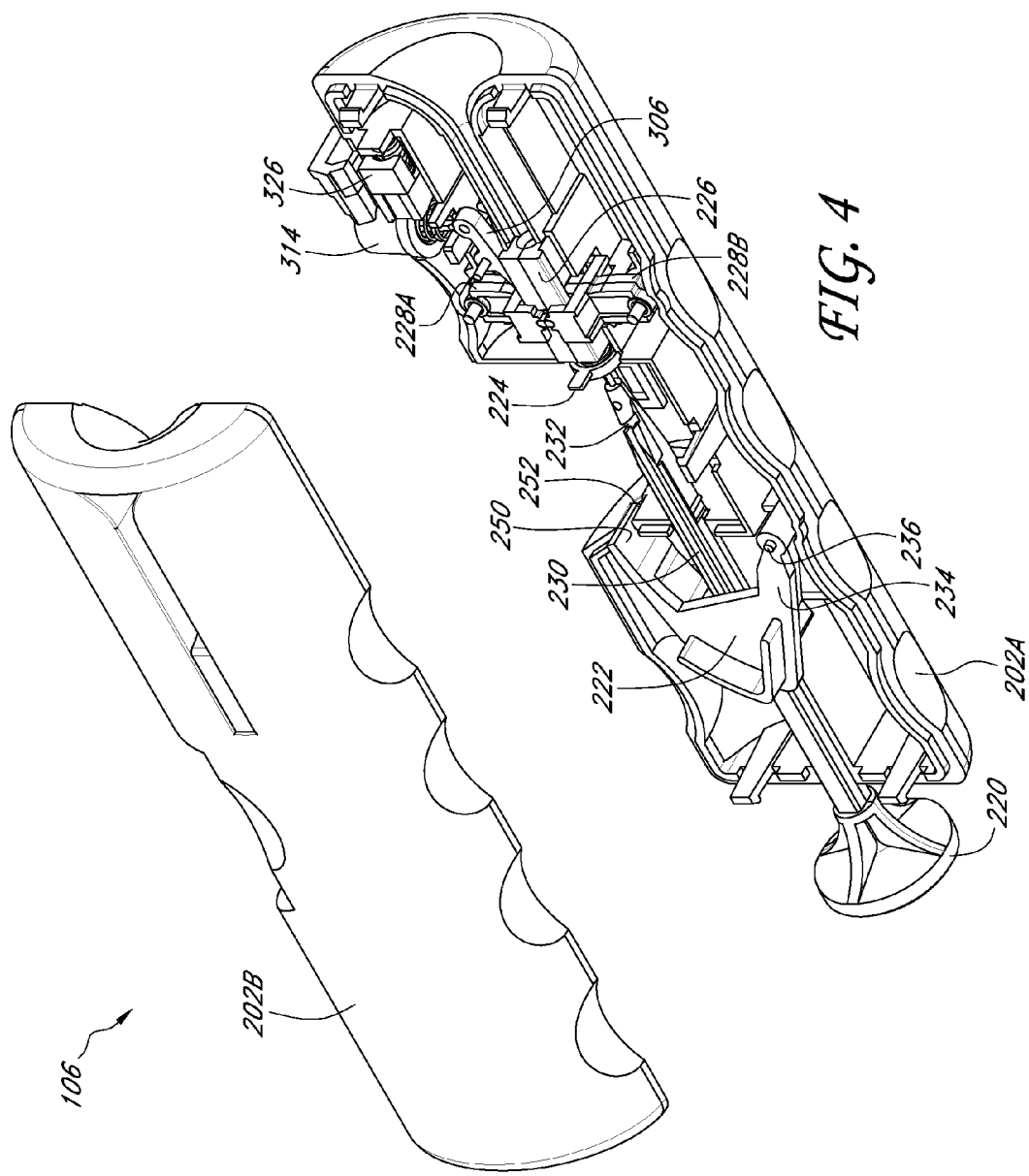
FIG. 4 is an exploded perspective view of the valve loader of FIG. 2.

In certain embodiments and as shown best in FIG. 3 and FIG. 4, the housing structure 202 defines one or more inner chambers that contain a plurality of components, including but not limited to a loader plunger 220 (also referred to herein as an actuator), a cartridge locking mechanism 222, an alignment insert 224, an alignment tube 226, and a first and a second grip pawl 228A, 228B.

Figure 5:
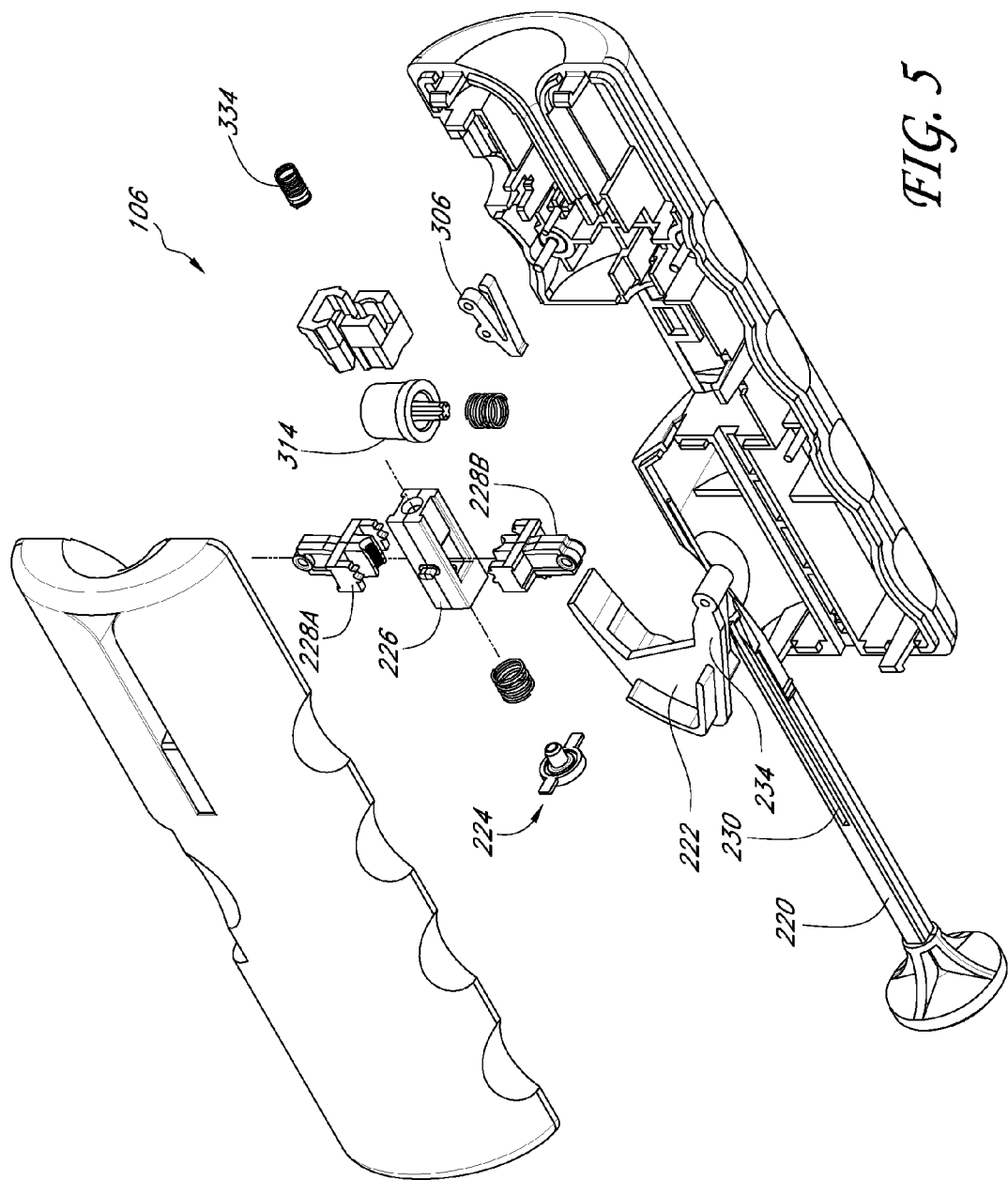
FIG. 5 is a further exploded perspective view of the valve loader of FIG. 2.

With reference to FIGS. 4 and 5, the loader plunger or actuator 220 is configured to slide within and along an axial center of the illustrated housing structure 202. In certain embodiments, the loader plunger or actuator 220 is configured to be screwed or rotated into and along an axial center of the housing structure 202. In certain embodiments, the housing structure 202 comprises a stop to signal or indicate to the user when the plunger or actuator 220 has traveled to the correct position in the housing for completely loading the valve or medical device into the deployment catheter or deployment apparatus. In certain embodiments, the cartridge 104 comprises a cover, cap, or lid 422 having a thicker tab 431 to act as a stop or signal or indication to the user when the plunger or actuator 220 has traveled to the correct position in the housing for completely loading the valve or medical device into the deployment catheter or deployment apparatus. In certain embodiments, the thicker tab 431 is changes length, shape, and/or size to determine how far the plunger or actuator 220 can travel into the housing thereby affecting the position of the valve or medical device within the deployment catheter or deployment apparatus. In certain embodiments, the cover, cap, or lid 422 can be positioned flushed with the outer surface of the cartridge 104 or the cover, cap, or lid 422 can be positioned (at different depths) inset from the outer surface of the cartridge 104 to determine how far the plunger or actuator 220 can travel into the housing thereby affecting the position of the valve or medical device within the deployment catheter or deployment apparatus. In certain embodiments, the cartridge 104 comprises a cover, cap, or lid 422 having a tooth or thinner tab 430 that provides an audible indication that the plunger or actuator 220 has traveled to the correct position in the housing for completely loading the valve or medical device into the deployment catheter or deployment apparatus. As shown in FIG. 5, the loader plunger or actuator 220 can have an axial groove 230 that extends along at least a portion of the loader plunger 220. The axial groove 230 preferably terminates proximally of the distal end of the loader plunger 220. The distal end of the axial groove 230 preferably terminates within a further groove 232 (see FIG. 4) that extends diagonally across the axial groove 230.

Figure 6:
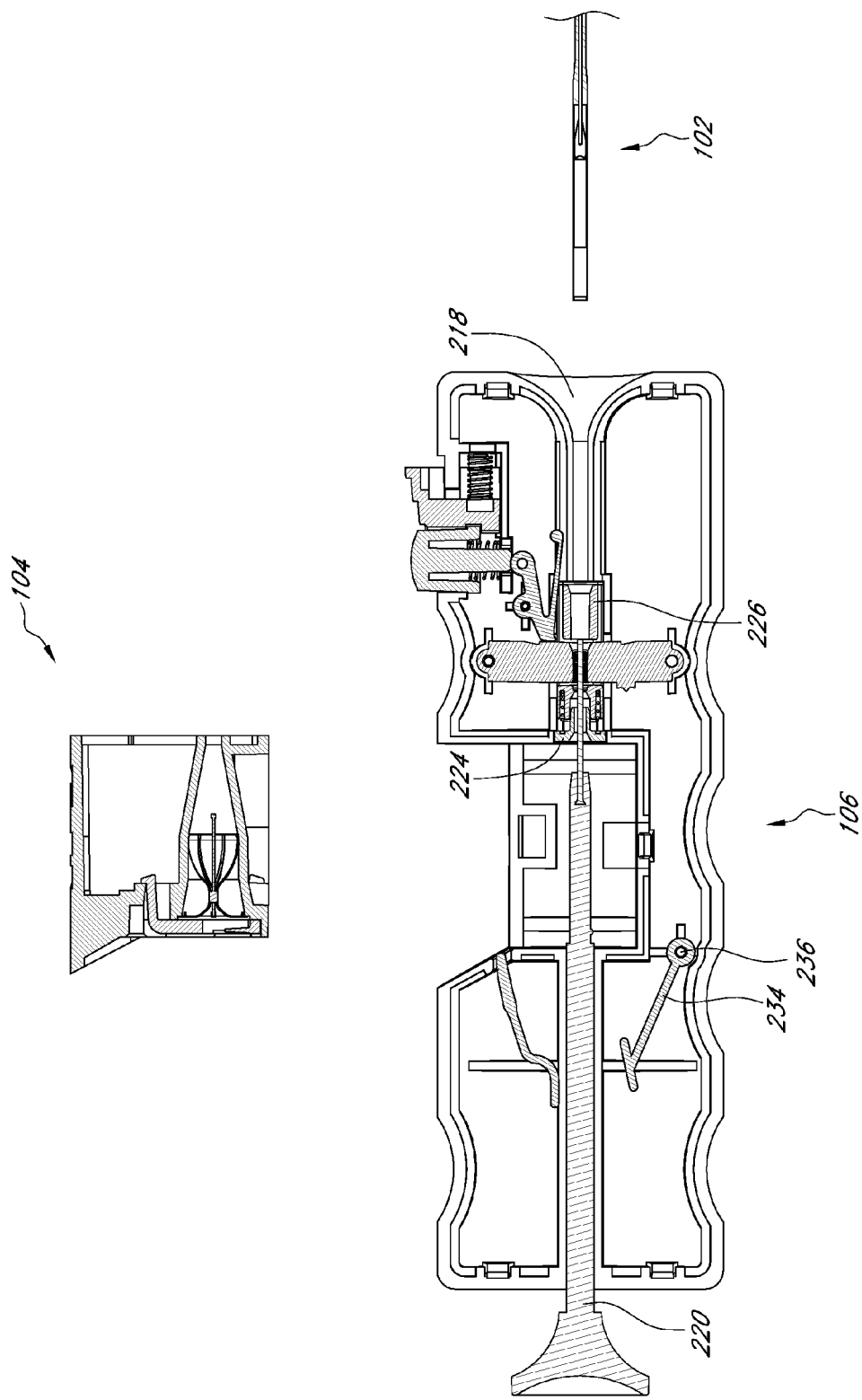
FIG. 6 is a sectioned view of some of the system components of FIG. 1 showing the valve loader in conjunction with an embodiment of a cartridge and an embodiment of a medical device to be loaded into an embodiment of a catheter or other deployment apparatus.
Figure 7:
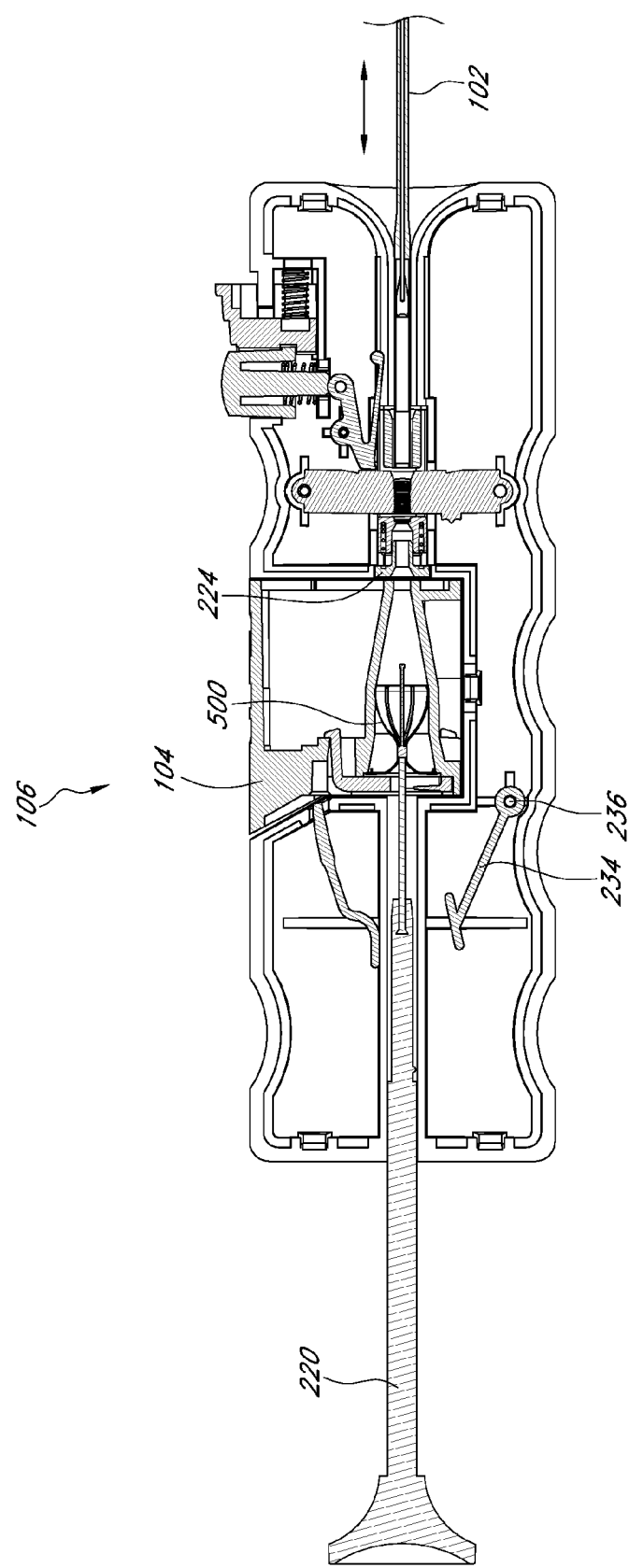
FIG. 7 is a sectioned view of the valve loader within the cartridge and the medical device of FIG. 6 loaded into the valve loader of FIG. 2.

As illustrated in FIGS. 4, 5 and 6, the cartridge locking mechanism 222 (also referred to herein as a safety apparatus) can be positioned within the housing structure 202. The illustrated cartridge locking mechanism 222 comprises a generally "U" shaped configuration or the like comprising a first end 234 and a second end. The first end 234 of the illustrated cartridge locking mechanism 222 is supported by and/or coupled to a pivot pin 236, and the balance of locking mechanism 222 is allowed to rotate or swing or move thereabout.

Figure 9:
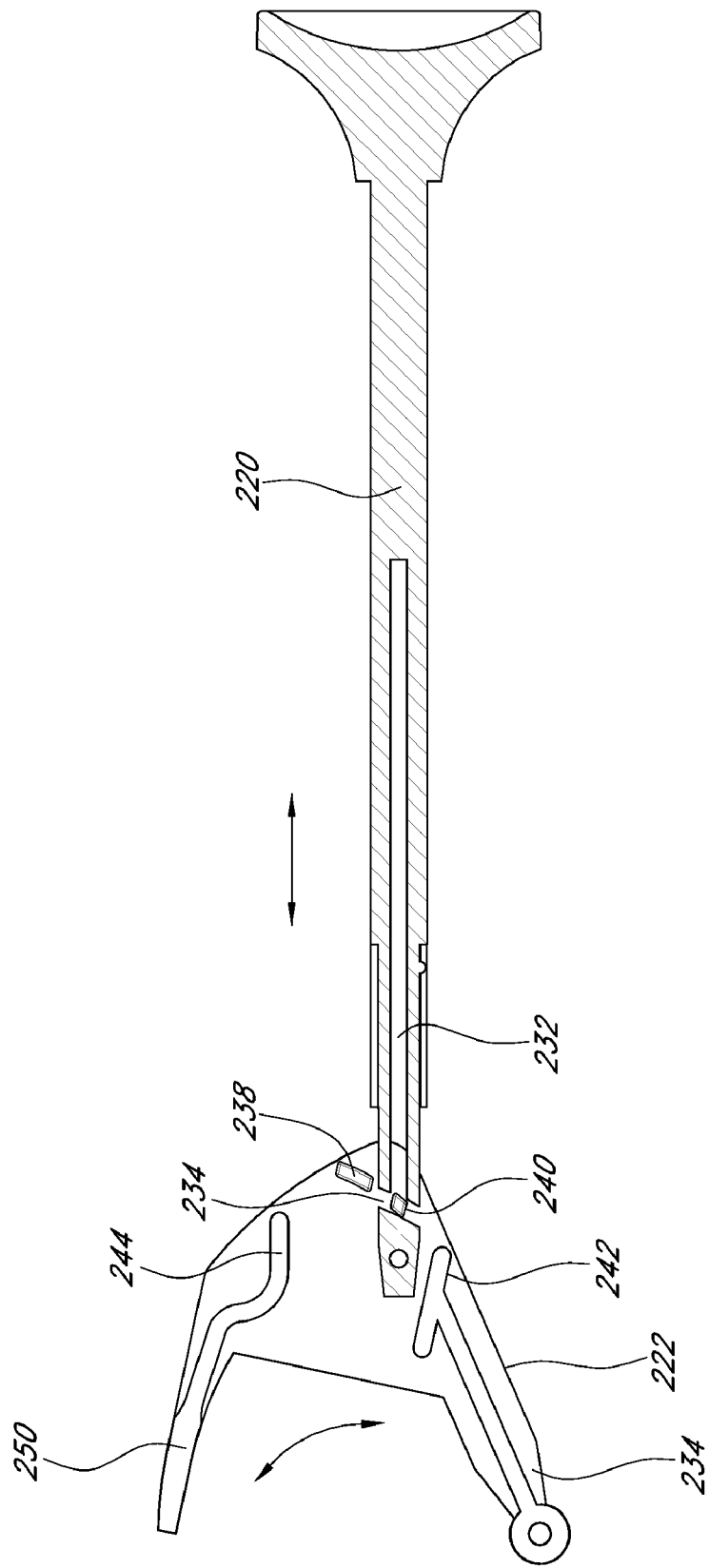
FIG. 9 is a sectioned view of a plunger and a locking mechanism of the valve loader of FIG. 2.

As shown in FIG. 5 and FIG. 9, the locking mechanism 222 comprises a first nub 238 and a second nub 240 that, in the illustrated configuration, face the male half 202A of the illustrated outer housing 202. The first nub 238 is slightly larger than the second nub 240 and the first nub 238 has a shape and orientation that generally corresponds to the shape and orientation of the groove 232. The first nub 238 is separated from the second nub 240 by a distance that can accommodate at least one of the surfaces that extends axially alongside the axial groove 230. In addition, the second nub 240 is sized such that it can be received within the axial groove 230 while the first nub 238 is sized such that it cannot be received within the axial groove 230.

Thus, as the loader plunger 220 is pushed into the housing structure 202, the locking mechanism 222 rotates slightly as the first nub 238 moves within the generally diagonal groove 232 until the second nub 240 is aligned with the axial groove 230. When the locking mechanism 222 has rotated and the second nub 240 is aligned with the axial groove 230, further pushing of the loader plunger 220 into the housing structure 202 causes the loader plunger 220 to move distally with the second nub 240 moving axially along the axial groove 232. During this continued movement, the locking mechanism is secured against rotation due to the positioning of the second nub 240 within the axial groove 230.

Similarly, as the loader plunger is withdrawn from the housing structure 202, the axial groove 230 moves relative to the second nub 240 until the second nub 240 reaches the diagonal groove 232. When the second nub 240 reaches the diagonal groove 232, the second nub 240 slides within the diagonal groove, which causes rotation of the locking mechanism 222. The rotation of the locking mechanism 222 draws the first nub 238 into the diagonal groove 232. The first nub 238 stops further withdrawal of the loader plunger 220 from the outer housing structure 202 after the first nub 238 is positioned within the diagonal groove 232.

Figure 8:
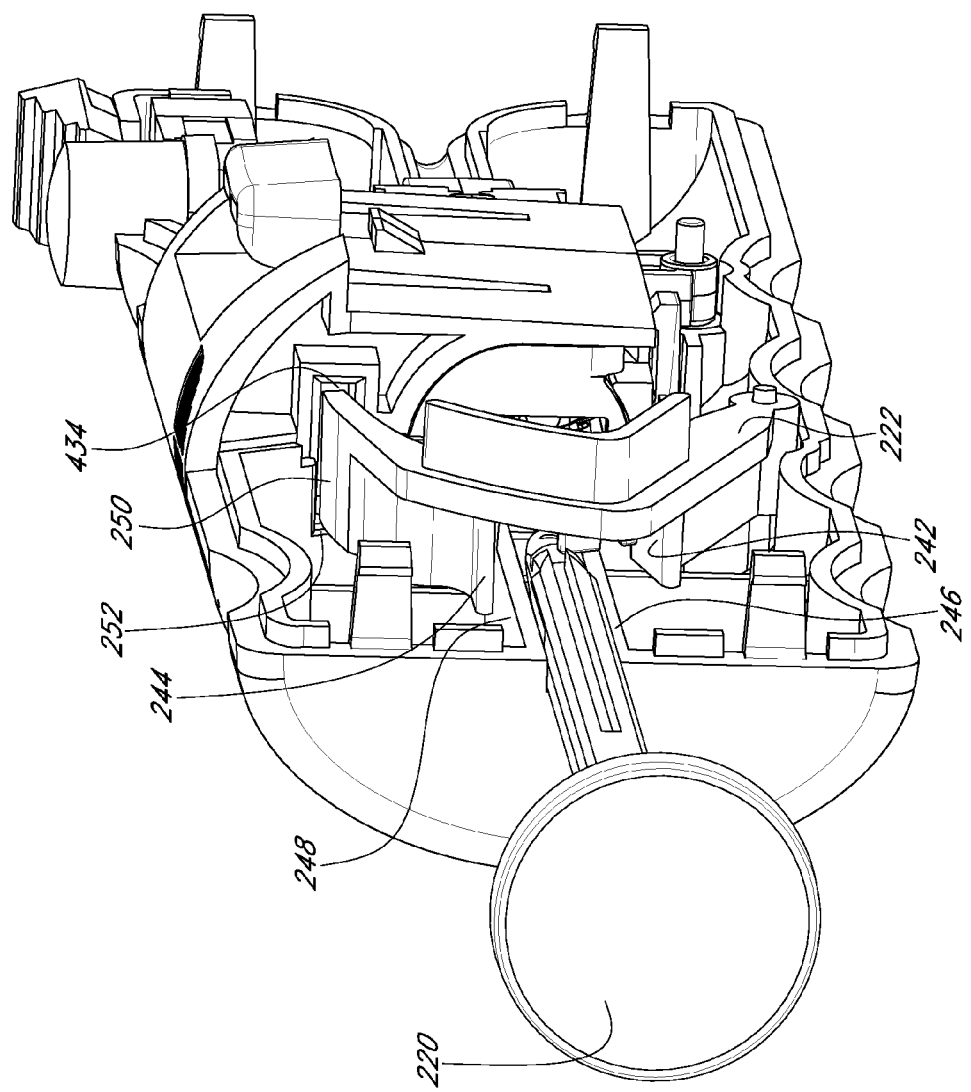
FIG. 8 is an enlarged perspective view of the valve loader of FIG. 2 with certain components removed.

With reference to FIG. 8, the locking mechanism 222 also comprises a first stop 242 and a second stop 244. The rotational movement of the locking mechanism 222 is limited in the illustrated configuration by the first stop 242 and the second stop 244. The first stop 242 moves into abutment with a first surface 246 of the housing structure 202 during rotation in a first direction (i.e., upward or clockwise rotation) and the second stop 244 moves into abutment with a second surface 248 of the housing structure 202 during rotation in a second direction (i.e., downward or counterclockwise rotation). Other configurations also can be used to limit the range of rotational movement of the locking mechanism 222.

As described above, the illustrated locking mechanism 222 also comprises a second end 250. The second end extends through an opening 252 that opens into the first open cavity 214. The second end 250 of the cartridge locking mechanism 222 acts as an arm, or a bracket, or a bar that secures the cartridge 104 into the first open cavity 214 of the housing structure 202, or that reduces the likelihood of the cartridge 104 being inserted into the first open cavity 214 without the loader plunger 220 being fully retracted from the housing structure 202. In this manner, the locking mechanism 222 safeguards the plunger 220 against damage that can be caused by insertion or removal of the cartridge 104 without the plunger 220 being fully retracted from the first open cavity 214 or the cartridge 104. As the locking mechanism 222 rotates, swings, or moves toward the first open cavity 214 of the housing structure 202, the arm, bracket, or bar of the second end 250 enters or moves into the first open cavity 214 of the housing structure 202 through the opening 252. If the cartridge 104 is within the first open cavity 214, then the arm, bracket, or bar of the second end 250 can engage with or otherwise lock the cartridge 104 into the first open cavity 214. As the loader plunger 220 is pulled out of the housing structure 202, the cartridge locking mechanism 222 rotates, swings, or moves the cartridge locking mechanism 222 away from the first open cavity 214 of the housing structure 202, thereby allowing the arm, bracket, or bar of the second end 250 to be removed or substantially removed from the first open cavity 214 of the housing structure 202 and to unlock or disengage the cartridge 104 if the cartridge is present within the first open cavity 214.

Figure 10:
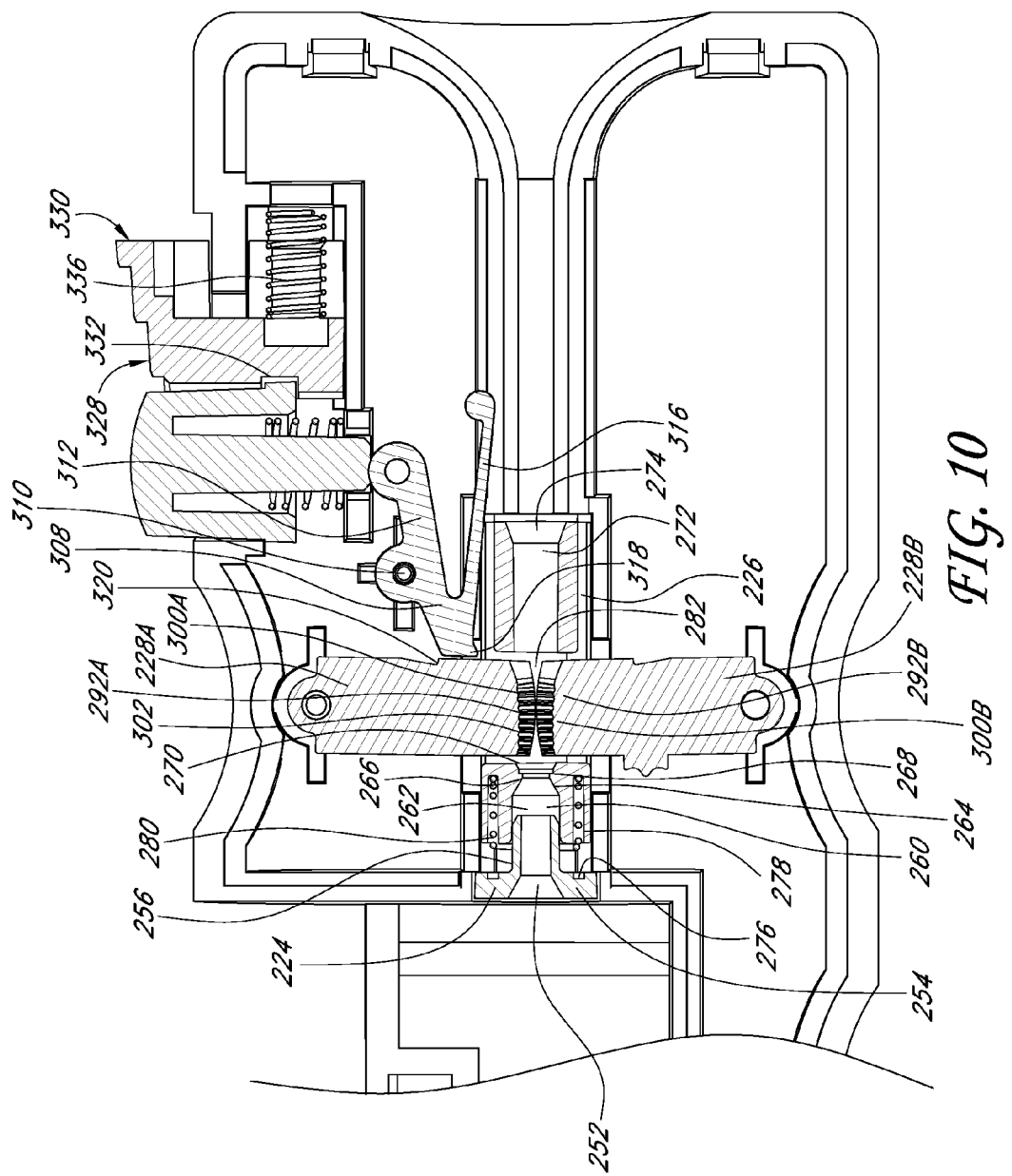
FIG. 10 is an enlarged sectioned partial view of the valve loader of FIG. 2
Figure 11:
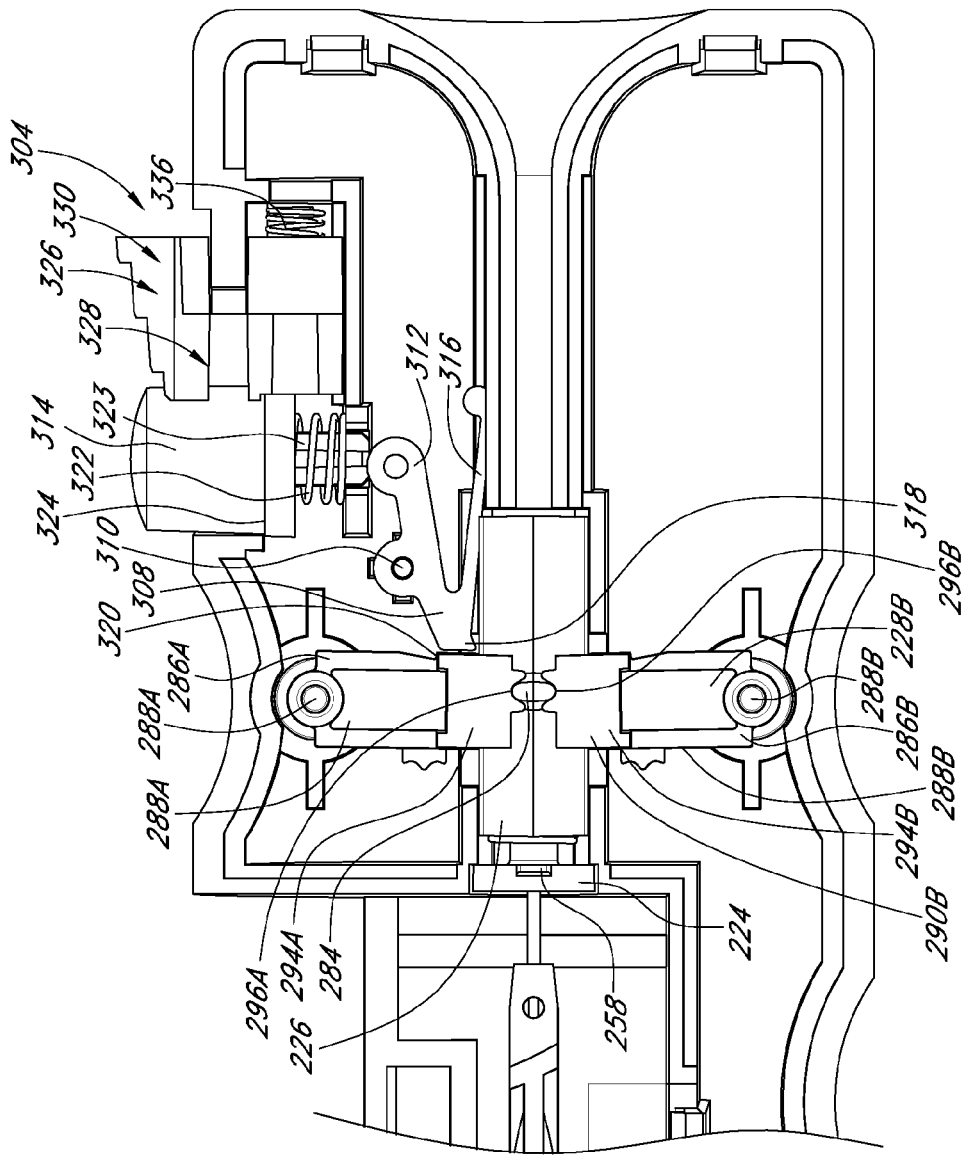
FIG. 11 is another enlarged sectioned partial view of the valve loader of FIG. 2
Figure 12:
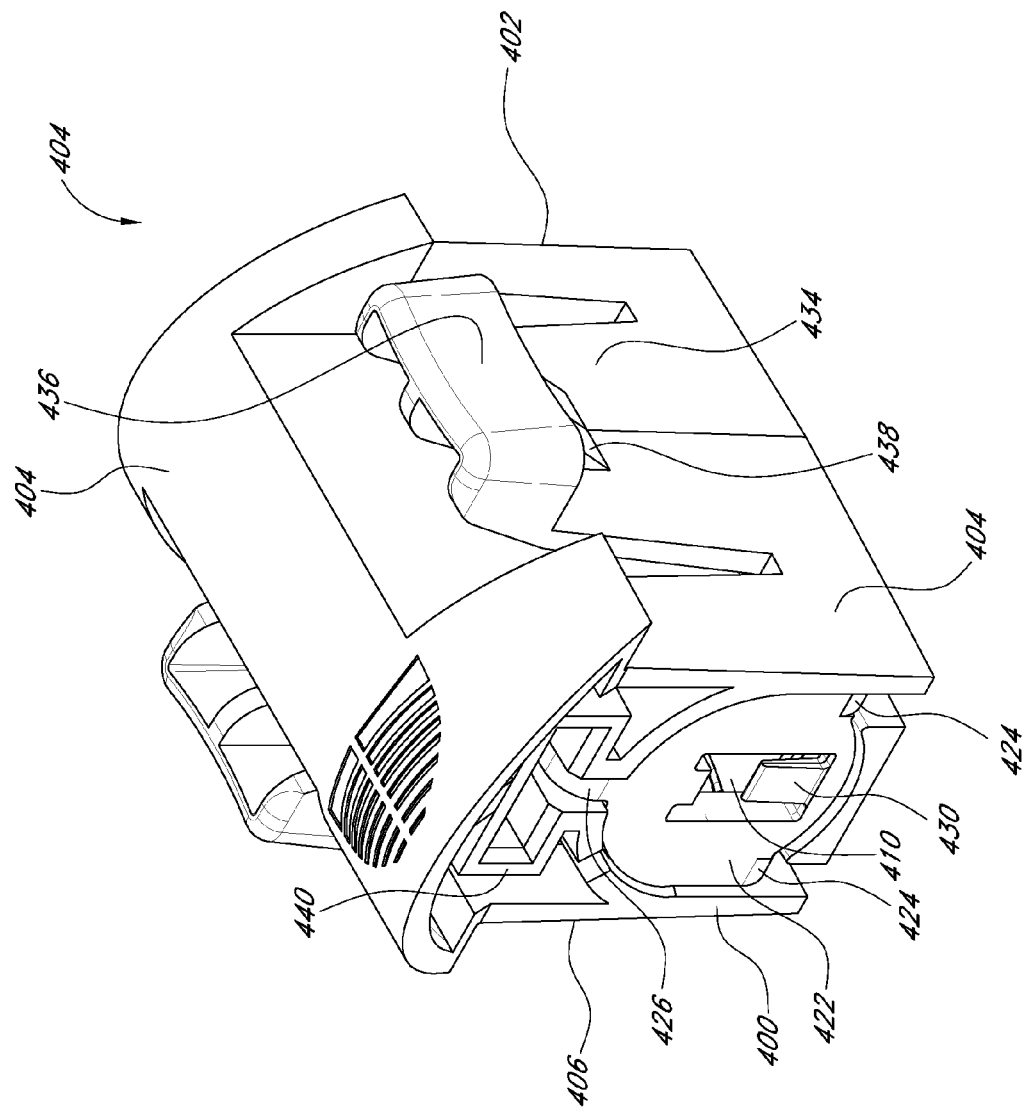
FIG. 12 is a perspective view of a cartridge used with the valve loader of FIG. 2.
Figure 13:
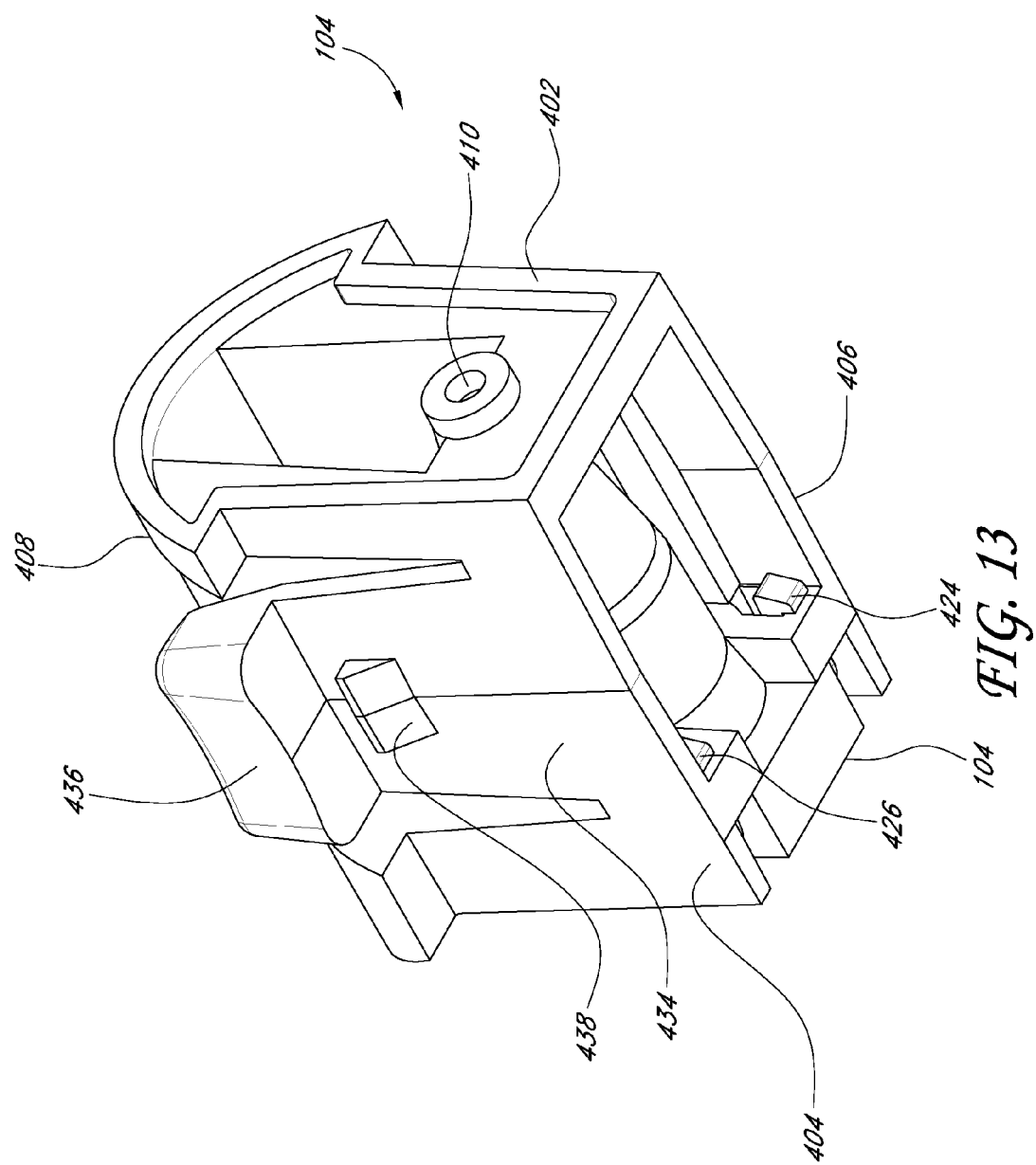
FIG. 13 is another perspective view of the cartridge of FIG. 12.

With reference to FIG. 10 and FIG. 11, the alignment insert 224 generally defines a passageway 252. At least a portion of the passageway 252 reduces in diameter from a proximal end of the portion to a distal end of the portion. In some embodiments, the diameter decreases from a proximal end of the alignment insert 224 to a location partway through the alignment insert 224. Other configurations are possible.

While the outer structure of the alignment insert 224 can have any suitable configuration, the illustrated configuration comprises a generally cylindrical proximal end 254 and a smaller diameter generally cylindrical proximal end 256. Preferably, the proximal end 254 of the alignment insert 224 is located such that its proximal end surface is generally flush with a surrounding or adjacent surface of the first open cavity 214.

The alignment insert 224 can be positioned in the housing structure 202, and can be configured to guide and/or compress the valve or medical device 704 into a compressed state for insertion or positioning into the deployment catheter 102. The alignment insert 224 can be constructed of plastic, metal, or other similar material. In the illustrated configuration, the proximal end 254 comprises two or more tabs 258. The tabs 258 can be positioned within recesses formed in the outer housing 202. Thus, the tabs 258 can help to properly locate the alignment insert 224 within the outer housing 202 and to limit axial movement of the alignment insert 224 relative to the outer housing 202.

The passage 252 defined by the alignment insert 224 preferably is axially aligned with a passage 260 defined by the alignment tube 226. The passage 260 comprises a proximal generally cylindrical portion 262, a tapering portion or funnel-shaped channel 264, a smaller diameter generally cylindrical portion 266, another slightly larger diameter generally cylindrical portion 268 and a slightly expanding portion 270. The passage further comprises a generally cylindrical distal portion 272 and a distal portion 274 that is generally conical in configuration.

The smaller diameter portion 266 preferably is smaller than the outer diameter of the catheter that the loader 106 is designed to be used with while the slightly larger diameter portion 268 is slightly larger than the same outer diameter. Accordingly, during insertion, the distal end of the deployment catheter 102 can abut against the step defined between these two portions 266, 268.

The generally cylindrical proximal portion 262 of the alignment tube 226 preferably is sized and configured to receive the distal end 256 of the alignment insert 224. As shown, the distally facing surface of the proximal end 254 of the alignment insert 224 can comprise a shallow channel 276 and the proximally facing proximal surface of a proximal end of the alignment tube 226 can be provided with a somewhat deeper channel 278.

A spring 280 or the like can be positioned within a proximal end within the shallow channel 276 of the alignment insert 224 and with a distal end within the deeper channel 278 of the alignment tube 226. The spring 280 or other biasing member advantageously biases apart the alignment insert 224 and the alignment tube 226. Because the alignment insert 224 is generally axially fixed relative to the outer housing 202 by the tabs 258, the alignment tube 226 is capable of axial movement relative to the outer housing 202 and can be biased by the spring 280 toward a first position, which can be defined by a feature of the surrounding portion of the outer housing 202.

The alignment tube 226 can constructed of plastic, metal, or other similar material. In certain embodiments, the alignment tube 226 has a generally rectangular outer shape (however, other shapes and configurations are possible without deviating from the spirit of the embodiment).

The alignment tube 226 preferably has an opening 282. The illustrated opening 282 is generally vertical. Preferably, the opening 282 extends through a central portion of the illustrated alignment tube 226. The opening 282 is configured to receive the first grip pawl 228A and the second grip pawl 228B, one on either side of the opening 282. In certain embodiments, the opening 282 has a rectangular shape but other shapes and configurations are possible as well. The alignment tube 226 also preferably comprises a first and a second external post 284. The post 284 extends laterally outward from the lateral surfaces of the alignment tube 226. Preferably, the position of the posts 284 are to each lateral side of the opening 282 such that the axial location of the posts 284 are between the proximal and distal ends of opening 282. Other configurations are possible.

The first and second grip pawls 228A, 228B preferably are constructed of plastic, rubber, polymer, or other similar material. The first grip pawl 228A can be positioned generally above the alignment tube 226 while the second grip pawl 228B can be positioned generally below the alignment tube 226. The grip pawls 228A, 228B each can comprise a first end 286A, 286B supported and/or coupled to a respective pivot pin 288A, 288B that is connected to the housing structure 202. Thus, the grip pawls 228A, 228B are allowed to swing or rotate about the pivot pins 288A, 288B. The grip pawls 228A, 228B each can also have a second end 290A, 290B.

Each second end 290A, 290B in the illustrated configuration comprises a gripping portion 292A, 292B and a surrounding portion 294A, 294B. The gripping portions 292A, 292B can be configured to be at least partially inserted into the opening 282 in the alignment tube 226, and the surrounding portions 294A, 294B can be configured to be at least partially wrapped around the outer surface of the alignment tube 226. More preferably, the surrounding portions 294A, 294B abut against the posts 284 of the alignment tube 226. Even more preferably, mounting recesses 296A, 296B formed in the surrounding portions 294A, 294B abut against the posts 284 of the alignment tube 226 and the mounting recesses 296A, 296B are offset in the distal direction relative to the rotational axes defined by the pins 288A, 288B. The slight offset in the location of the recesses 296A, 296B relative to the rotational axes defined by the pins 288A, 288B cause the alignment tube 226 to snap into the first position following any slight displacement in the proximal direction.

In a default or normal position, the grip pawls 228A, 228B can be substantially perpendicular to the alignment tube 226. With the second ends 290A, 290B of the first and second grip pawls 228A, 228B positioned in the alignment tube 226, there is a first gripping portion 300A and a second gripping portion 300B that come together and form a generally cylindrical or tubular area or clamp that is configured to hold, clamp, retain, lock, and/or grip the deployment catheter 102 within the alignment tube 226.

The first and second gripping portions 300A, 300B comprise peaks, sharp features or ribs 302. As shown, the ribs 302 preferably are configured to define a larger inner diameter at the proximal and distal ends and a smaller inner diameter in the middle. Thus, as the grip pawls 228A, 228B rotate in the proximal direction, the diameter defined by the ribs that are generally normal to each other is greater than the diameter defined by the ribs in the middle that are generally normal to each other when the grip pawls 228A, 228B rotate back toward the starting position (i.e., corresponding to the first position of the insert tube 226). Thus, in the starting position, the center ribs of the ribs 302 cooperate to retain the end of the deployment catheter while, once rotated from the starting position in the proximal direction, the larger ribs cooperate together and define a larger diameter such that the deployment catheter can be inserted or removed from the grip pawls 228A, 228B.

In some configurations, one or more of the grip pawls 228A, 228B abuts against at least a portion of a release mechanism 304. The illustrated release mechanism 304 comprises a leaf spring 306. A first portion 308 of the leaf spring 306 is supported by and/or coupled to a pivot pin 310 and the leaf spring 306 is allowed to at least partially rotate about the pivot pin 310. The first portion 308 of the leaf spring 306 comprises a cantilever portion 312 that can be engaged with a button 314. The leaf spring 306 comprises a second portion 316 that can be configured to rest at least partially on an inner structure of the outer housing 202, the alignment tube 226 or the like. The first portion 308 and the second portion 316 can be joined at a proximal end and can extend at an angle relative to each other. In addition, the first portion 308 preferably is more rigid (e.g., has a greater thickness to resist bending) than the second portion 310. Rotation of the first portion 308 about the pivot pin 310 causes flexure of the second portion 316 such that the second portion 316 acts to resist rotation of the first portion 308 about the pivot pin 310. More preferably, the second portion 316 biases the first portion 308 to a starting position if the cantilever portion 312 is moved downward in the illustrated configuration by the button 314.

As illustrated in FIGS. 10 and 11, the leaf spring 306, in certain embodiments, comprises a cam portion 318 that is engaged with the grip pawl 228A. In certain embodiments, the grip pawl 228A, 228B comprises a ledge, lip, groove, or cavity 320 that can be engaged by the cam portion 318 of the leaf spring 306 when the cam portion 318 slides upward along the side of the grip pawl 228A a sufficient distance. Thus, the cam portion 318 of the grip pawl 228A can be locked into the deflected position until a proximally directed force is provided to the alignment tube 226. The leaf spring 308 can make a distinct clicking sound or other audible sound when snapping into position on the ledge of the grip pawl 228A.

As discussed above, when the button 314 is pressed into the housing structure 202, the button 314 applies a force on the cantilever portion 312 thereby causing the leaf spring 306 to rotate, pivot or swing about the pivot pin 310. The movement of the cantilever portion 312, and therefore the first portion 308, of the leaf spring 306 causes the cam portion 318 to rotate, which causes the cam portion 318 to effectively slide along a portion of the grip pawl 228A and snap into position alongside the grip pawl 228A. The interaction between the cam portion 318 and the grip pawl 228A causes the grip pawl 228A to rotate away from the pivot pin 310. The movement of the grip pawl 228A causes movement of the alignment tube 226 in the proximal direction due to the interface between the mounting recesses 296A, 296B and the posts 284. The movement of the alignment tube 226 results in rotation of both of the grip pawls 228A, 228B and the grip on any catheter previously secured within the alignment tube 226 is released such that the catheter can be removed.

Preferably, the cam portion 318 remains in contact with the surface of the grip pawl 228A until a subsequent catheter insertion occurs. In the illustrated embodiment, the slight step 320 is provided onto which a portion of the cam portion 318 rests. The movement of the cam portion 318 over the edge of the step 320 results in a sound that indicates the unclamping of the catheter for removal. A subsequent insertion of a catheter drives the alignment tube 226 further in the proximal direction, which allows cam portion 318 of the leaf spring to drop off of the step 320 and to snap back to its original position with an accompanying sound that indicates that clamping of the catheter has occurred.

The button 314 can be constructed of plastic, metal or other suitable material and the button 314 can be moveably positioned within the housing structure 202. In certain embodiments, the button 314 is coupled to, connected to or engaged by a spring or other biasing element 322 that applies a force to push the button 314 towards the outer surface of the top side 204 of the housing structure 202, which is the normal position for the button 314. The button 314 comprises a lip or ledge 324 that can be configured to prevent the button 314 from being forced entirely out of the housing structure 202 by the spring or biasing element 322. The spring or biasing element 322 can be mounted over a stem 323 of the button 314. When the button 314 is pressed into the housing structure 202, the button 314 moves toward a second position in which the spring 322 is compressed. In the second position, the button 314 engages and/or applies a force on the cantilever portion 312 of the leaf spring 306, thereby causing the cam portion 318 of the leaf spring 306 to engage the first grip pawl 228A to release the deployment catheter 102. In certain embodiments, the button 314 engages and/or applies a force on the cantilever portion 312 of the leaf spring 306, thereby causing the cam portion 318 of the leaf spring 306 to engage the first grip pawl 228A to move or rotate the first grip pawl 228A towards the proximal end thereby causing the release the deployment catheter 102. In certain embodiments, the first and second grip pawls 228A, 228B are coupled (for example, due to their connection to the alignment tube 226), and accordingly, when the first grip pawl 228A is moved or rotated by the leaf spring 306 toward the proximal end, both the first and second grip pawls 228A, 228B move or rotate in concert toward the proximal end thereby releasing their grip on the deployment catheter 102.

In certain embodiments, the button 314 is also coupled and/or engaged with a safety slide mechanism 326 as illustrated in FIGS. 10 and 11. The safety slide mechanism 326 can be configured to reduce or eliminate the likelihood of the button 314 being pushed into the housing structure 202 unless such a movement is desired. The safety slide mechanism 326 can be constructed of plastic, metal, or other like material. The safety slide mechanism 326 comprises a proximal end 328 and a distal end 330. In certain embodiments, the proximal end 328 comprises a cavity or groove 332 that can be configured to engage or receive the lip or ledge 324 of the button 314. In other words, when the slide mechanism is in a proximal position, the rim, ridge, lip or ledge 324 of the button 314 is positioned within the cavity or groove 332 of the slide mechanism 326 and, therefore, the slide mechanism 326 reduces the likelihood of unintended depression of the button 314.

The distal end 330 of the safety slide mechanism 326 is coupled to, connected with, in contact with or engaged with a spring or other biasing element 336 that applies a force to push the safety slide mechanism 326 towards the button 314 to engage the lip or ledge 324 of the button 314 with the cavity or groove 332 of the safety slide mechanism 326. In some configurations, the safety slide mechanism 326 comprises a recess that receives at least a portion of the spring or other biasing element 336. When the safety slide mechanism is moved or slid distally toward a second position, the safety slide mechanism 326 releases, disengages, and/or allows the button 314 to be pressed into the housing structure 202.

Thus, to remove or unlock or release the distal end of the deployment catheter 102 from the alignment tube, a two step unlocking process is used in certain embodiments. In order to unlock the deployment catheter 102, the user first slides the safety slide mechanism 326 toward the distal end and the user then pushes the button 314 into the housing structure 202 in order to unlock and pull out the deployment catheter 102 from the housing structure 202. The two step unlocking process reduces or eliminates the possibility of breaking the deployment catheter 102 while positioning the valve 704 into the deployment catheter 102. Additionally, the two step unlocking process reduces or eliminates the possibility of removing the deployment catheter 102 before the valve 704 has been properly positioned within the deployment catheter 102.

Cartridge

The cartridge 104 can have any suitable size, shape or configuration. In the illustrated embodiment, the cartridge 104 is sized, shaped and configured to be received within the first open cavity 214. More preferably, the cartridge 104 is sized, shaped and configured to be received within the first open cavity 214 in only one orientation.

The illustrated cartridge 104, as shown in FIGS. 12-21, generally comprises a proximal wall 400 and a distal wall 402. A first side wall 404 and a second side wall 406 generally extend between the proximal wall 400 and the distal wall 402. The illustrated cartridge also comprises a top wall 408 that, for aesthetic reasons, can correlate in shape and configuration (for example, a mating shape) to the outer housing 202 of the valve loader 106. The term "wall" should not be construed narrowly to mean any single surface or member but rather should be construed broadly and a wall can be comprised of multiple surfaces that are not in a single plane but that, in cooperation with one another, form a general boundary. The illustrated cartridge 104 therefore comprises a generally rectangular box shape with a rounded top wall. Other configurations and shapes, for example, circular, cylindrical square, triangular, cone, trapezoidal, elliptical, or a combination thereof, also are possible.

The cartridge 104 can be formed in any suitable manner and of any suitable material. In some embodiments, the majority of the cartridge 104 is molded of plastic or metal or another suitable material.

The cartridge 104 preferably defines at least one passage 410 that extends in a proximal to distal direction. In some embodiments, the passage 410 extends from the proximal wall 400 to the distal wall 402. Preferably, the passage 410 comprises a first tapering portion or tapered lumen 412 that tapers from proximal to distal, a generally cylindrical portion 414 and a second tapering portion 416 that also tapers from proximal to distal. Thus, the passage 410 extends from a proximal opening 418 to a distal opening 420 and the proximal opening 418 is larger than the distal opening 420. Other configurations are possible but the passage 410 preferably generally reduces in diameter from the proximal opening 418 to the distal opening 420.

Figure 14:
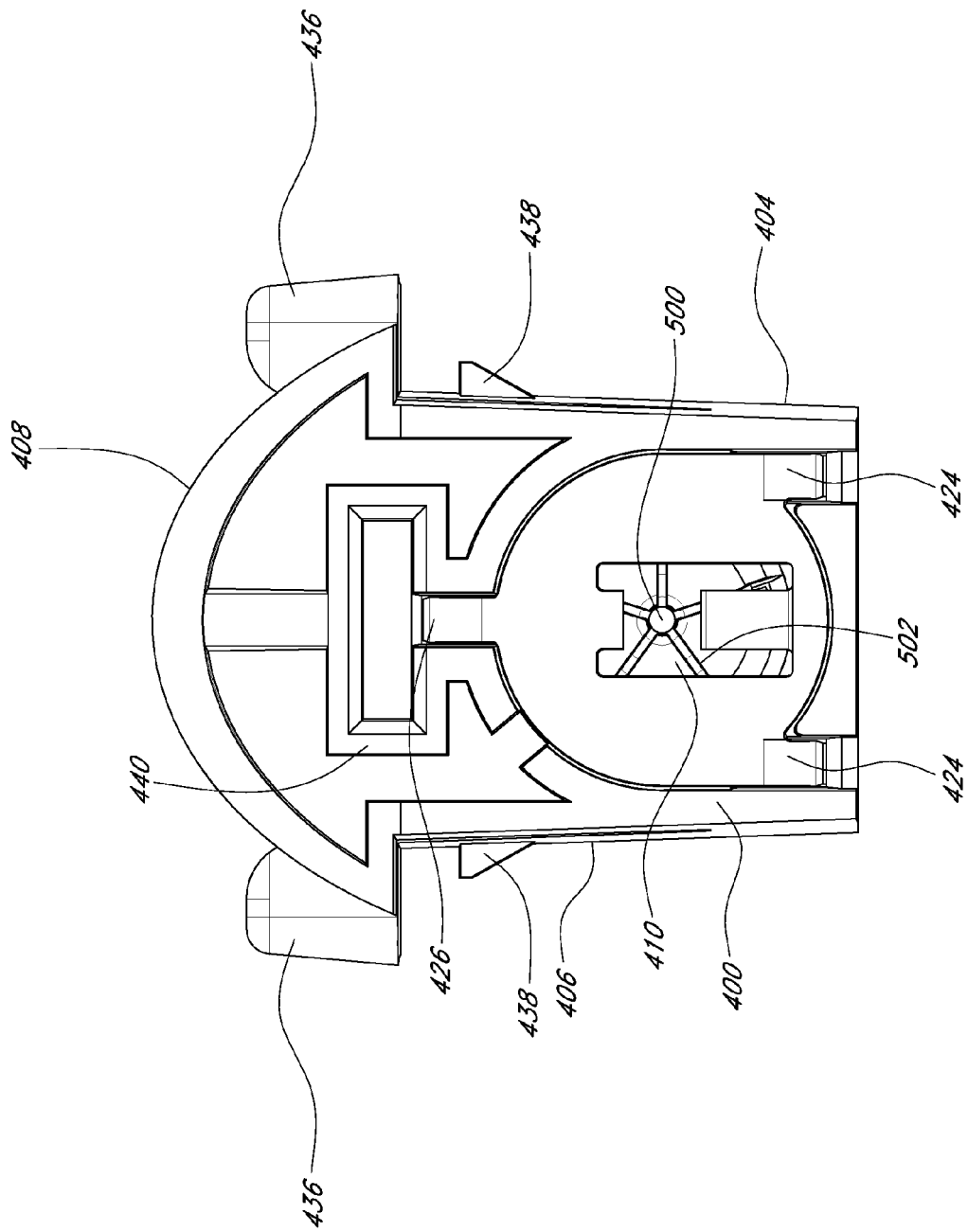
FIG. 14 is a front view of the cartridge of FIG. 12.
Figure 15:
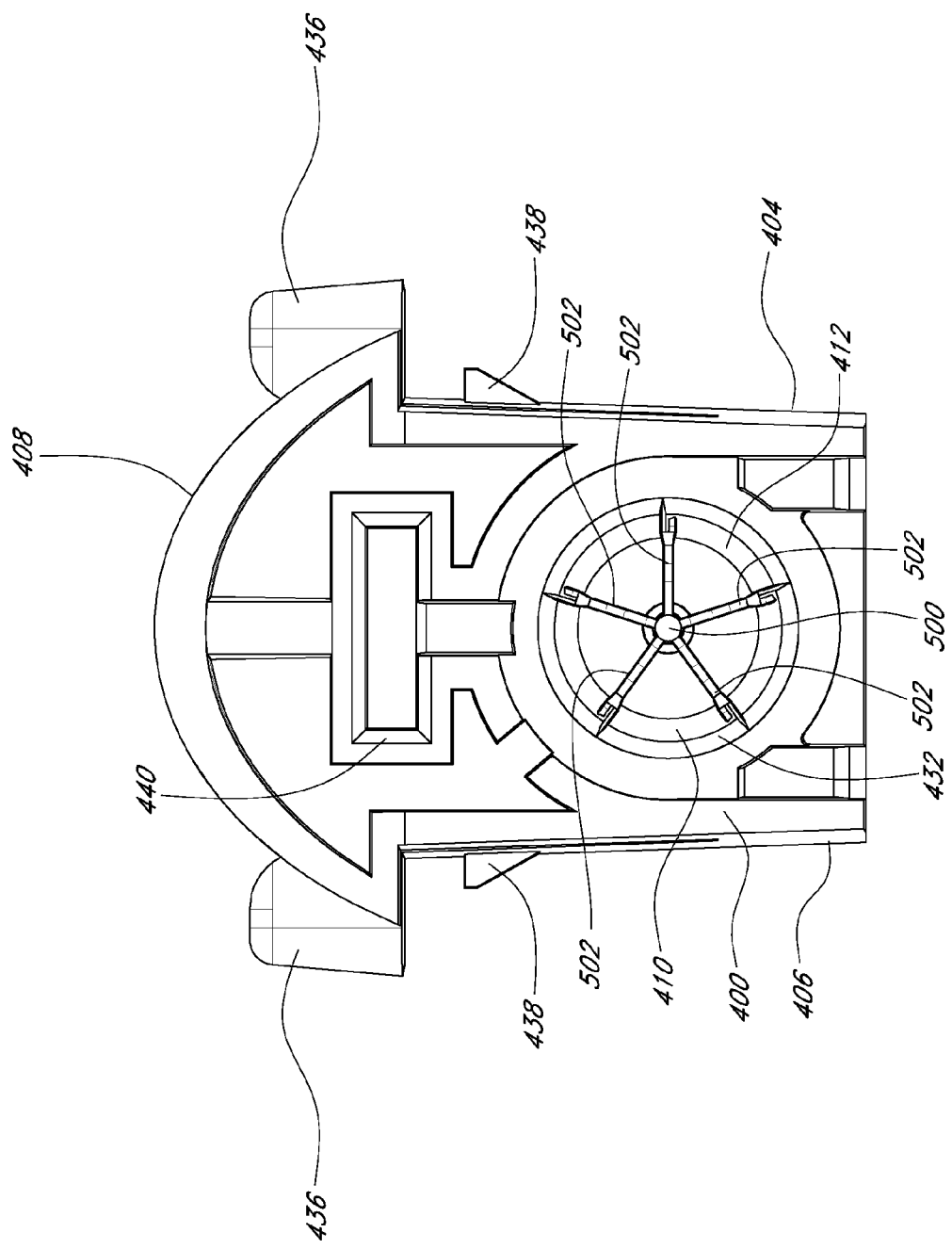
FIG. 15 is a further front view of the cartridge of FIG. 12 with a cover removed.
Figure 16:
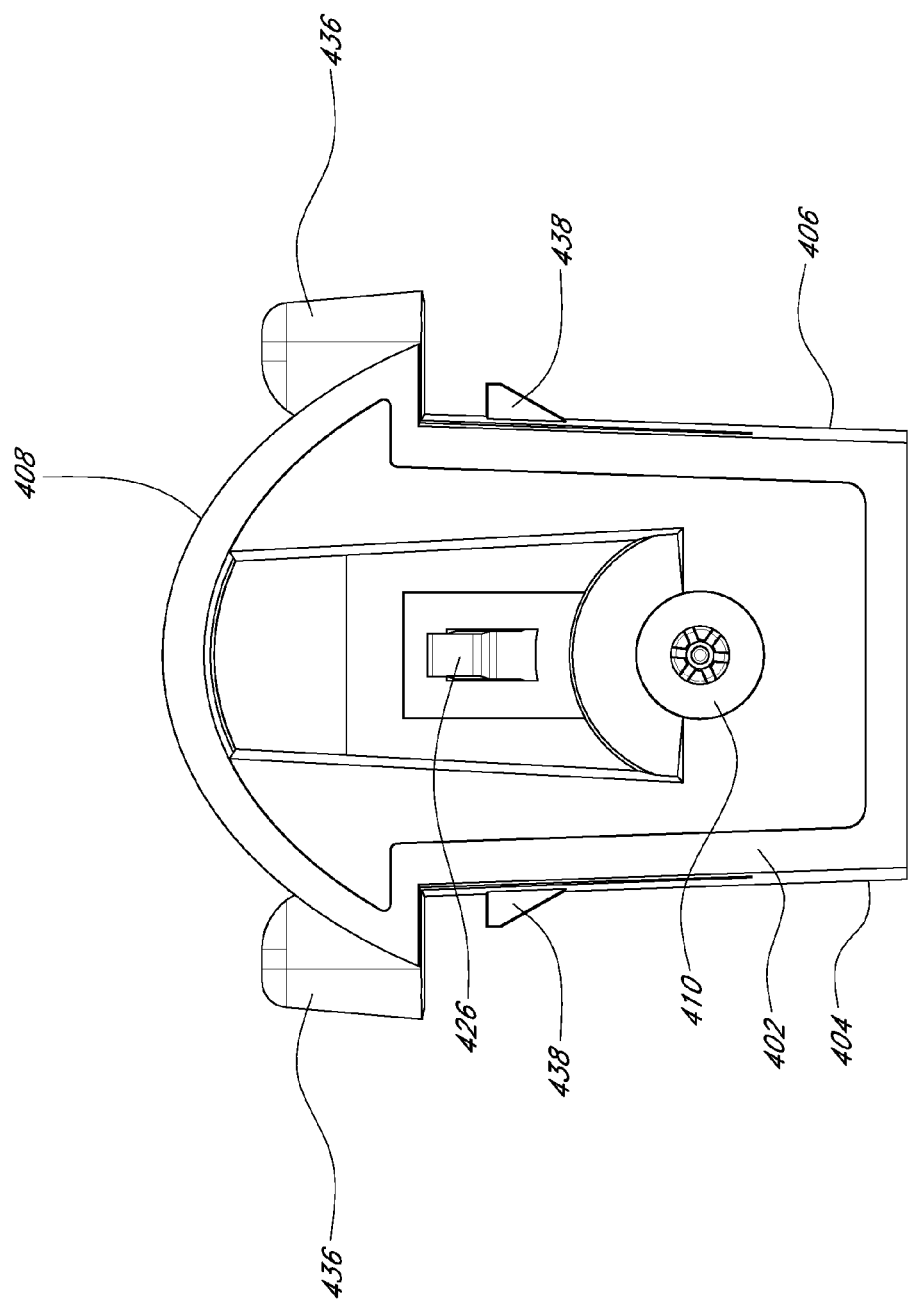
FIG. 16 is a rear view of the cartridge of FIG. 12.
Figure 17:
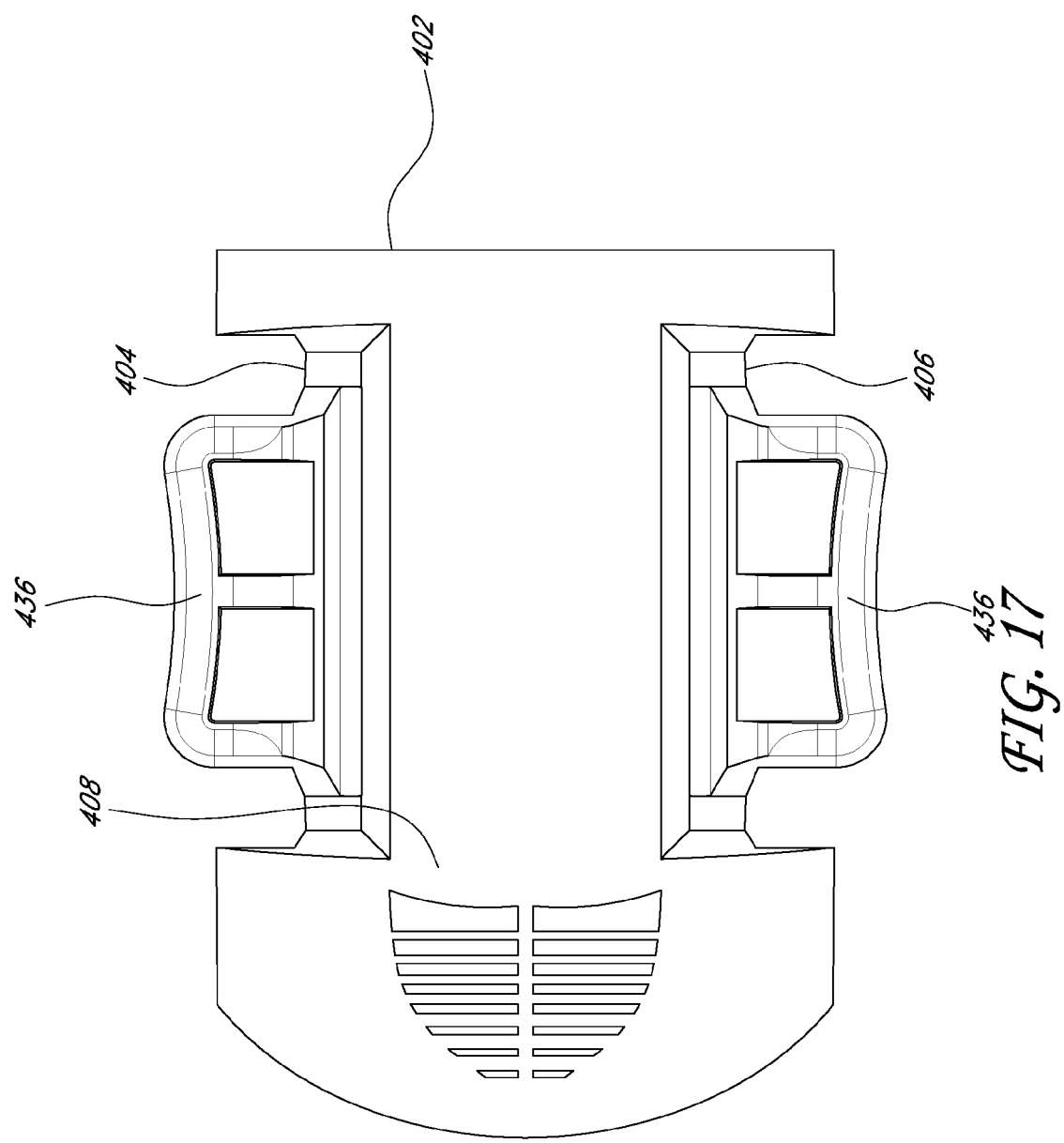
FIG. 17 is a top view of the cartridge of FIG. 12.
Figure 18:
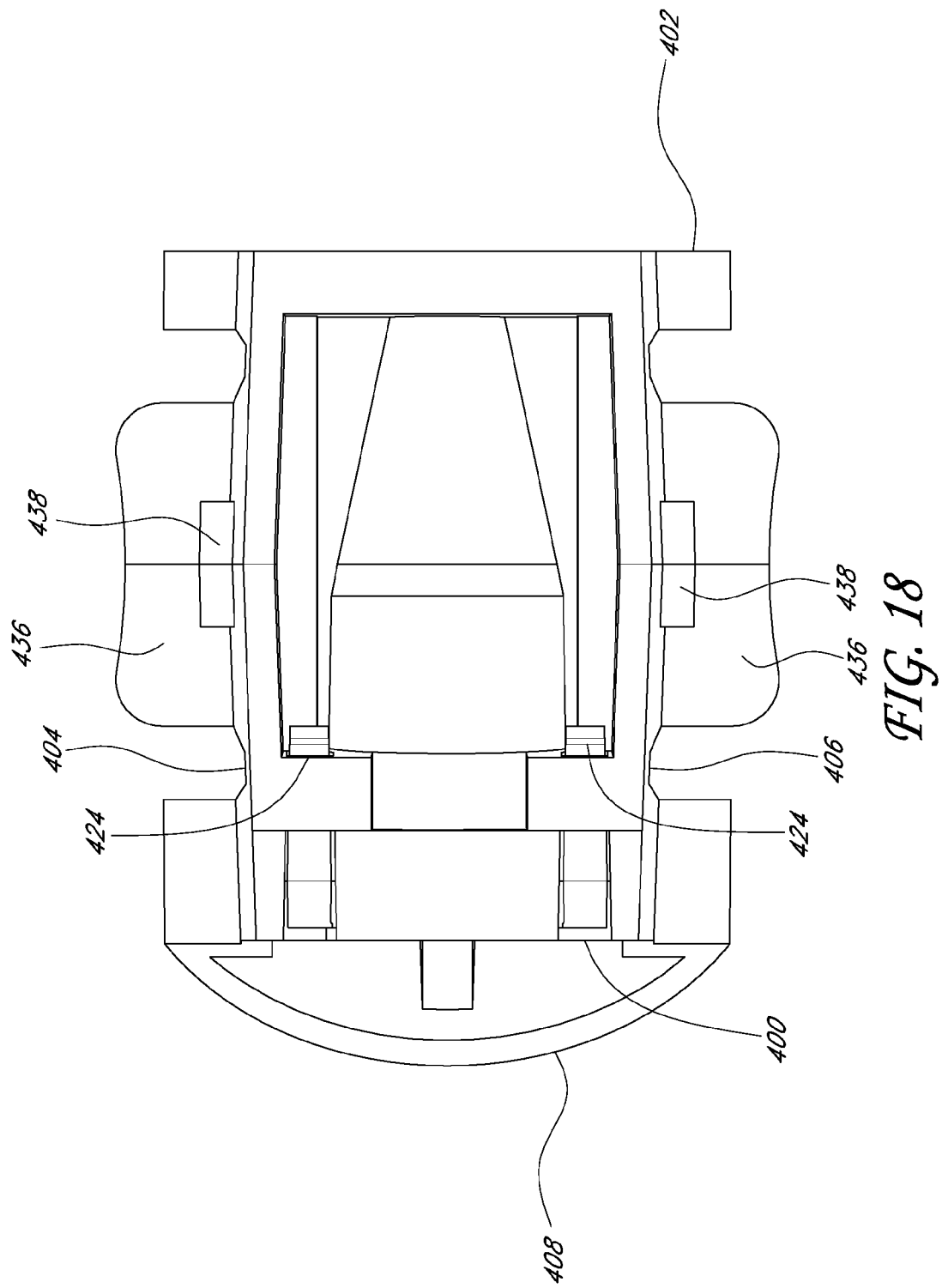
FIG. 18 is a bottom view of the cartridge of FIG. 12.
Figure 19:
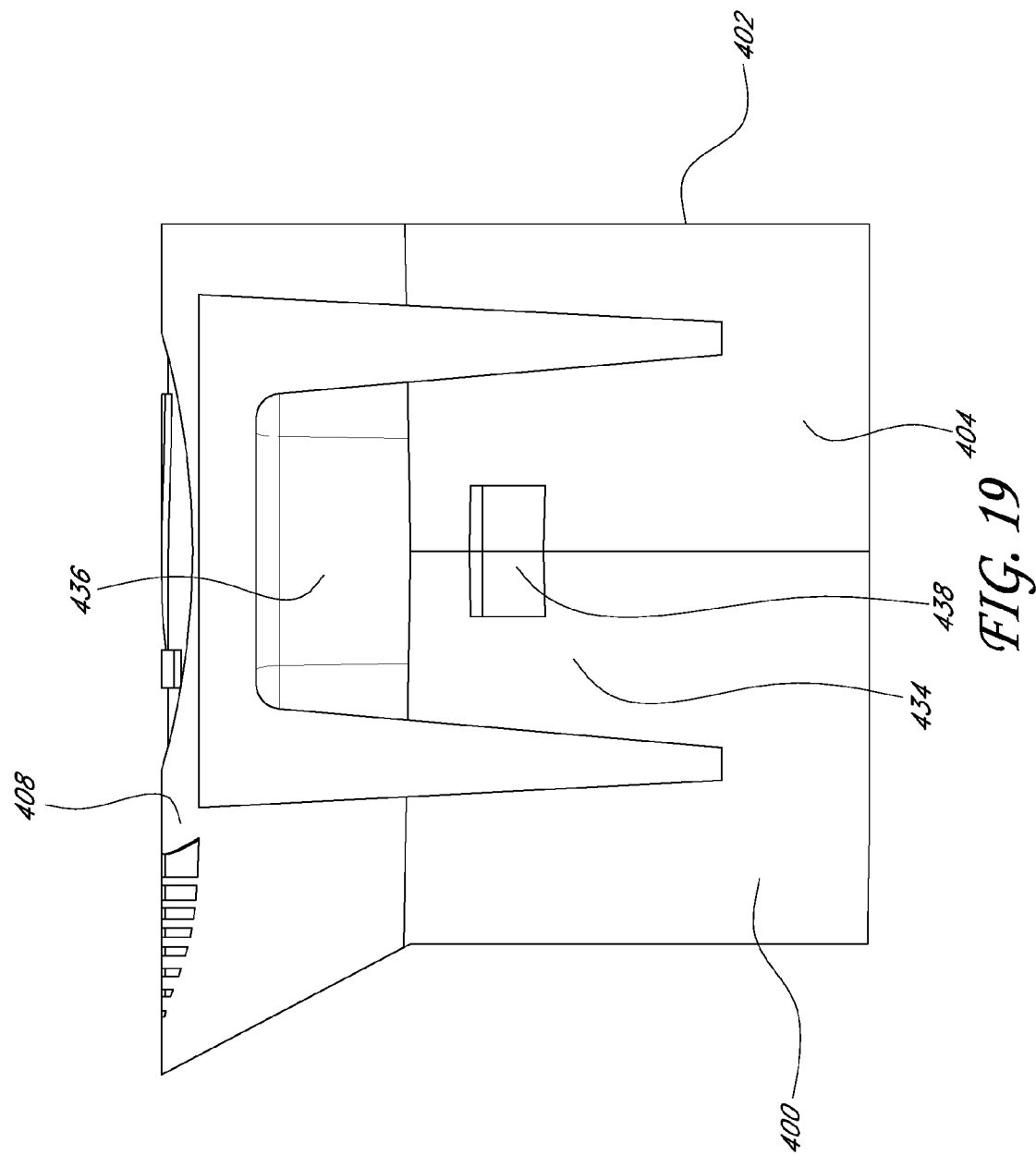
FIG. 19 is a left side view of the cartridge of FIG. 12.
Figure 20:
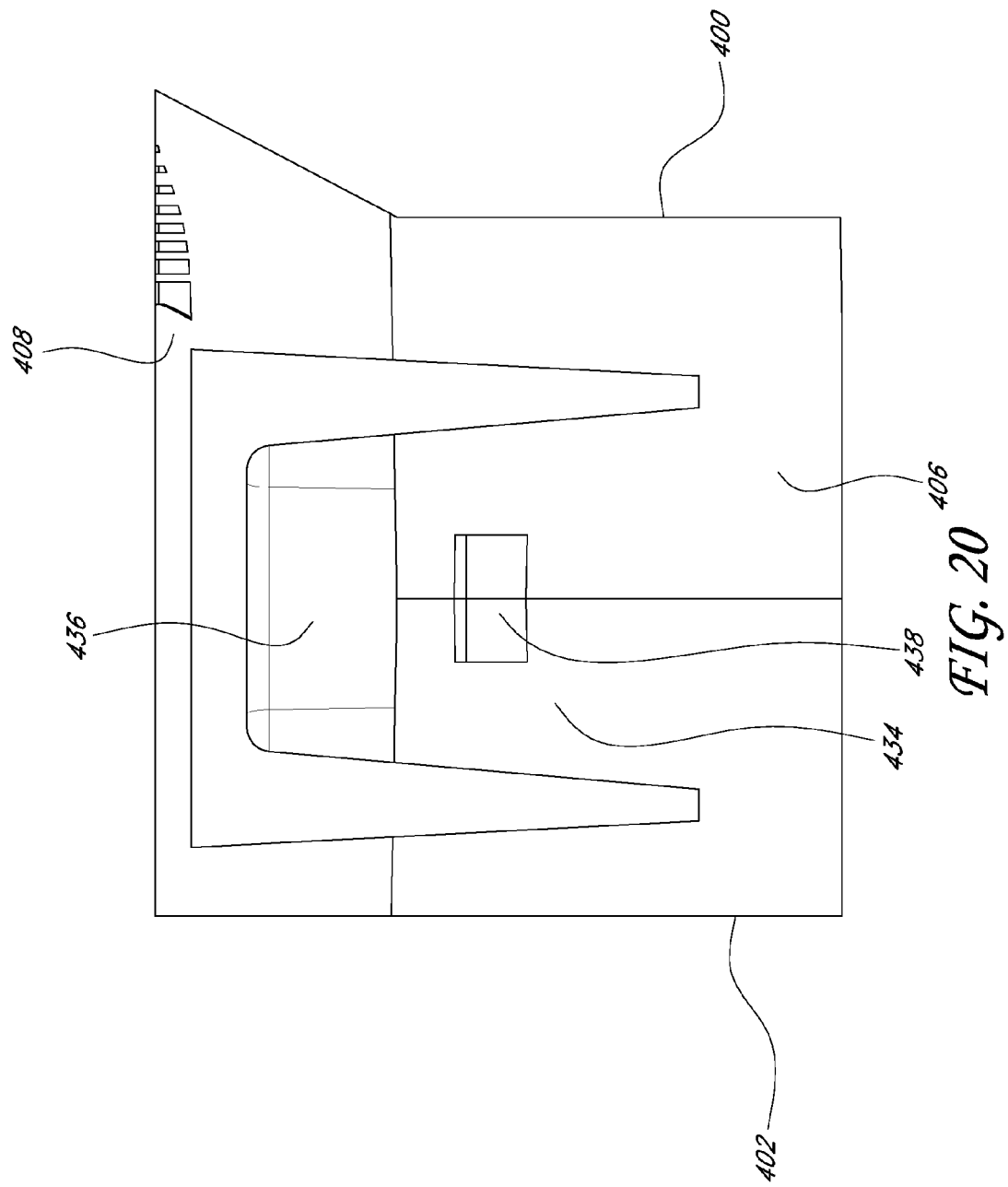
FIG. 20 is a right side view of the cartridge of FIG. 12.
Figure 21:
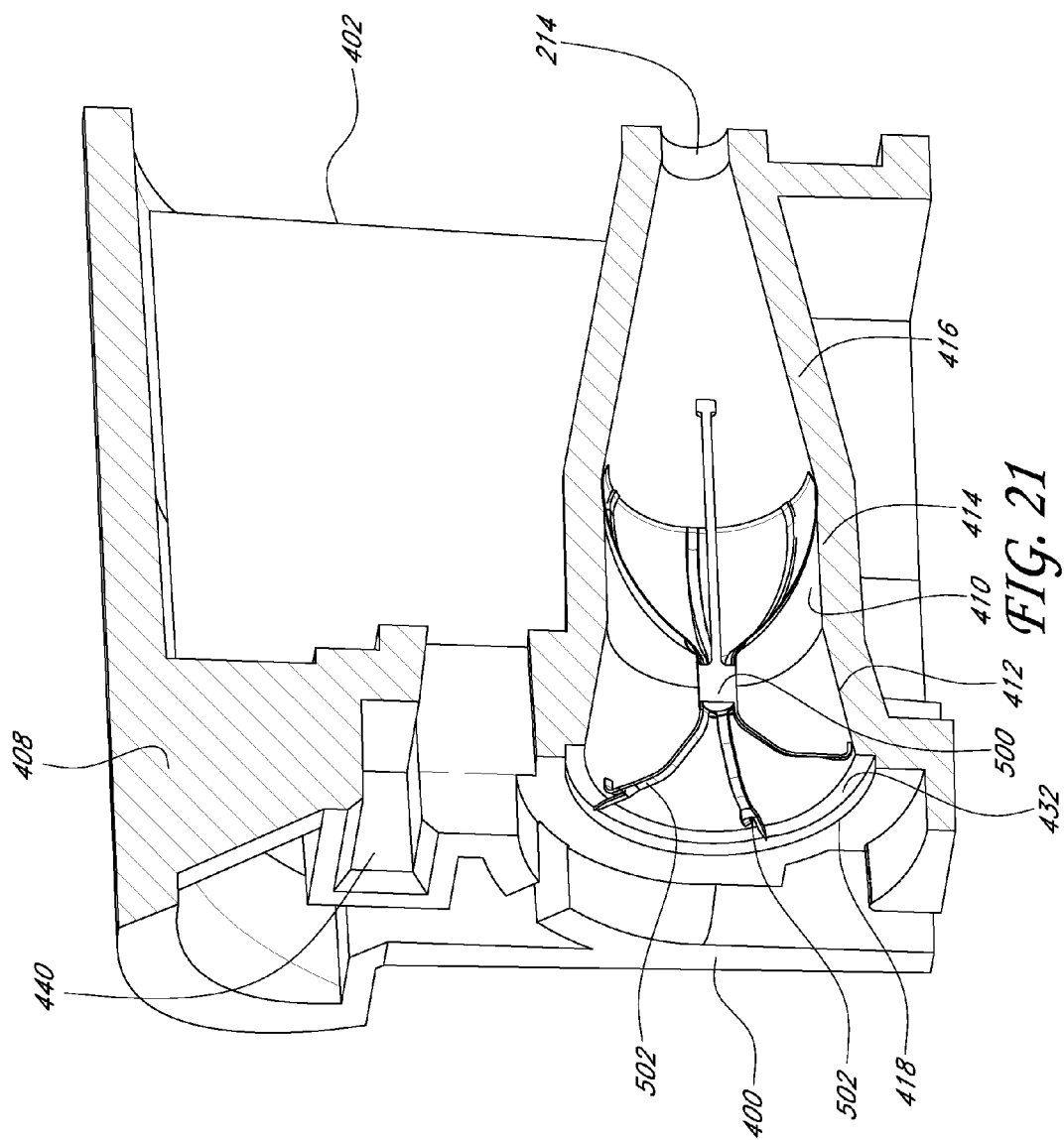
FIG. 21 is a sectioned perspective view of the cartridge of FIG. 12.

The proximal opening 418 preferably is generally closeable using a cover, cap or lid 422. The cover 422 is shown in FIG. 14 and is shown removed in FIG. 15. The cover 422 can have any suitable configuration. In the illustrated embodiment, the cover 422 is generally transparent or translucent and is formed of a plastic material. The illustrated cover 422 snaps into place on the cartridge 104 but other configurations are possible. The illustrated cover 422 comprises two lower legs 424 and one upper leg 426 that snap into corresponding openings formed within the cartridge 104.

The cover 422 preferably defines an opening 428. The opening 428 can have any suitable size and configuration. In the illustrated embodiment, the size and shape of the opening 428 generally correlates to a cross-sectional configuration of the plunger 220. In addition, a tooth or thinner tab 430 extends upward into the illustrated opening 428. The tooth 430 preferably is deflectable. The plunger 220 is received within the opening 428 during use and the tooth 430 snaps into position over a rib formed on the plunger. The tooth 430, therefore, acts to indicate when the plunger 220 is fully depressed and the tooth 430 also maintains the fully depressed position of the plunger 220 until the plunger 220 is acted upon by a sufficient force to retract the plunger 220 in a proximal direction.

The at least one passage 410 preferably is configured to receive and store a valve or other medical device 500. The cover 422 is configured to reduce or eliminate the likelihood of the valve or medical device 500 being removed from the cartridge 104 while the valve or medical device 500 is intended to be stored in the cartridge 104. As shown, the medical device 500 can comprise multiple anchors 502. The anchors 502 can define a diameter. Preferably, the proximal opening 418, between the cover 422 and the first tapering portion 412, comprises a counterbore 432 that has an outer diameter larger than the diameter defined by the anchors 502 and an inner diameter that is slightly smaller than the diameter defined by the anchors 502. Thus, the anchors 502 can be captured between the distal wall of the counterbore 432 and the cover 422.

In certain embodiments, the passage 410 can be configured to receive and/or store more than one valve or medical device 500 that are of the same or different size, shape, or type. Preferably, different cartridges 104 comprise different colors, symbols, numbers, and/or other unique identifiers to indicate that different size valves or medical devices 500 are stored within the cartridges 104. In some configurations, the cartridges 104 can use other identifying indicial (e.g., numbers, colors, letters, patterns, etc.) to indicate differing medical devices, including whether different pharmaceuticals, coatings, or the like are used.

In certain embodiments, the cartridge 104 can comprise multiple passages 410 or chambers for storing multiple valves or medical devices 500, and the multiple hollow centers or chambers can be coupled to a daisy wheel or other revolver within the cartridge 104 such that the daisy wheel or other revolver can be rotated or otherwise moved e.g., raised or lowered) by the user so as to allow multiple valves 500 to be loaded into the deployment catheter 102.

The cartridge 104 preferably also comprises at least one release tab 434. The release tab 434 is joined to the cartridge at a base and can be integrally formed with the cartridge 104. In the illustrated embodiment, each of the two lateral sides has a release tab 434. The end of each release tab 434 comprises a finger pad 436 and, just below the finger pad 436, a locking protrusion 438. The locking protrusion 438 engages a corresponding structure on the valve loader 106 to lock the cartridge 104 into the first open cavity 214 of the housing structure 202. When the finger pads 436 of the two release tabs 434 are squeezed toward each other, the locking protrusions 438 separate from the structure of the housing 202 and the cartridge 104 is released from the first open cavity 214 of the housing structure 202. In one embodiment, the release tabs 434 are integrally formed with the cartridge 104 and are constructed of plastic, polymer, or other suitable material. Other locking configurations also can be used.

The proximal wall 400 of the cartridge 104 can comprise at least one groove region or recess 440 that receives the arm, bracket, or bar of the second end 250 of the cartridge locking mechanism 222. Thus, when the second end 250 extends into the first open cavity 214, the second end 250 engages with the groove region 440 of the cartridge 104.

Deployment Catheter

It will be appreciated that any kind of deployment catheter 102 can be used with the valve loader 106, and that the following description of the illustrated deployment catheter 102 is intended to be generally illustrative only and not limiting.

Figure 22:
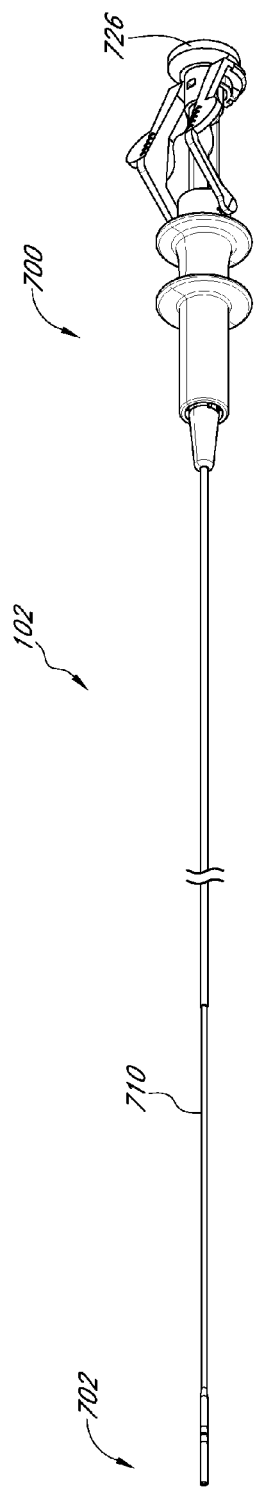
FIG. 22 is a perspective view of an embodiment of a deployment catheter or other deployment apparatus used in the system of FIG. 1.
Figure 23:
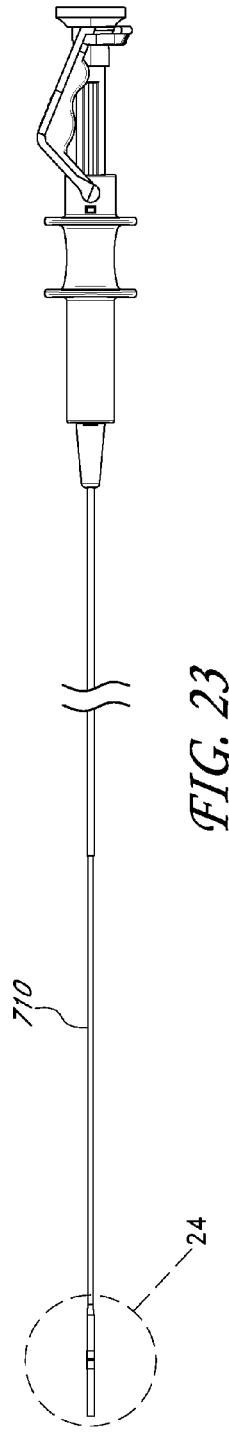
FIG. 23 is a side view of the deployment catheter or other deployment apparatus of FIG. 22.
Figure 24:
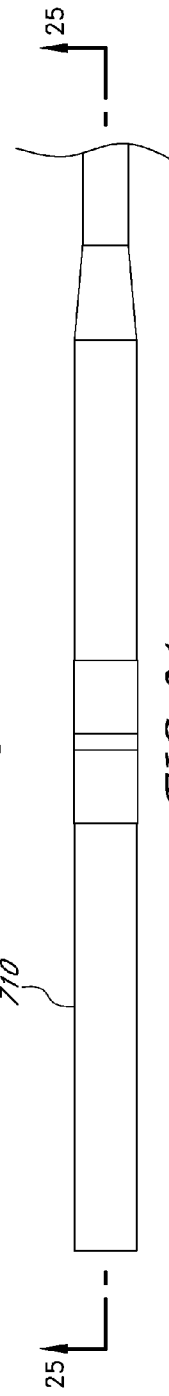
FIG. 24 is an enlarged view of a distal end of the deployment catheter or other deployment apparatus of FIG. 23 taken in the circle 24 of FIG. 23.

With reference to FIG. 22, the deployment catheter 102 has a proximal end 700 and a distal end 702. A control portion 704 is located at the proximal end 700 and a delivery portion 706 is located at the distal end 702.

With reference to FIGS. 22-25, a catheter shaft 710 extends from proximal end to distal end. The catheter shaft 710 can be configured to be inserted into a bronchoscope or the body. Preferably, the catheter shaft 710 comprises an internal lumen 712 and a distally-located cavity 714. The internal lumen 712 can have a distal end that is in communication with the cavity 714. In some embodiments, the lumen 712 of the catheter shaft 710 can have a coating, for example, Teflon, or a lining, for example, a polytetrafluoroethylene (PTFE) liner, or some combination of the two. Other configurations are possible.

The catheter shaft 710 can be constructed of plastic, metal, polymer, rubber, nylon, other flexible materials, or a combination thereof. In certain embodiments, the catheter shaft 710 is constructed of a flexible polymer extrusion, for example, PEBAX® or nylon. In certain embodiments, the catheter shaft 710 may have different regions comprising a different durometer level. For example, a majority of the proximal end of the catheter shaft 710 may have a harder durometer that prevents elongation, whereas the distal end of the catheter shaft 710 may have a softer durometer for increased flexibility. In some configurations, the catheter shaft 710 can comprise various fillers or components, for example, colorants for color, barium sulfate for radiopaque applications, and Teflon for lubricity.

The distal end of the catheter shaft 710 can comprise a catheter tip 716. In some embodiments, the catheter tip 716 can be located at the most distant portion of the distal end 702. The catheter tip 716 can define at least a part of a catheter sheath 718 that is retractable relative to the valve 500 so the valve 500 can be deployed or implanted from the catheter shaft 710 into the body.

In some embodiments, at least a portion of the catheter sheath 718 comprises a clear or translucent material. With reference to FIG. 29A a visualization window 801 into cavity 714 may be provided in certain embodiments to permit an operator to verify that a device (such as valve 500) has been loaded or inserted into the distal end 702 of the deployment catheter. This visualization window 801 may be constructed of a material that is at least translucent, but preferably transparent.

The catheter sheath 718 and/or catheter tip 716 can comprise a valve line (in certain embodiments, the valve line comprises a marker embedded in or applied to the catheter sheath 718 to verify the proper placement of the valve 500. In a preferred embodiment, the valve line indicates where the valve 500 will deploy in the body. For example, one or more locator markings (e.g., lines 802, 803) may be provided on the distal end 702, permitting an operator to visualize where a device will be deployed. These locator markings 802, 803 may comprise a thin yellow-pigmented line 803 embedded in the catheter sheath 718 denoting the approximate location where a device (such as the valve 500) will be deployed. Further, the line 803 may be surrounded by wider black-pigmented bands 802 to provide additional contrast for ease of visualization by the operator, for example through a bronchoscope. Some embodiments may have coils or other structural elements present at the distal end. Accordingly, the lines 802 may then be useful to mask or hide such underlying structural elements to avoid confusing an operator as to the location of the line 803. In certain embodiments, a valve 500 may have one or more lines 802 or 803 disposed or printed directly upon it. Although the line 803 may be colored with different pigments, a yellow pigment was found to be easily visible through the visualization channel of a bronchoscope. Any method may be employed to place these locator markings on the distal end 702. For example, pad printing or inkjet printing may be used to mark the lines 802 and 803 on the distal end 702. Other practices may be used to mark lines 802 and 803, including hot stamping, swaging, or reflowing a marker band. Lines 802 could also be printed second on each side of the first printed line 803. Other configurations are possible, and of course, different pigments and locator markings may be employed.

Figure 30:
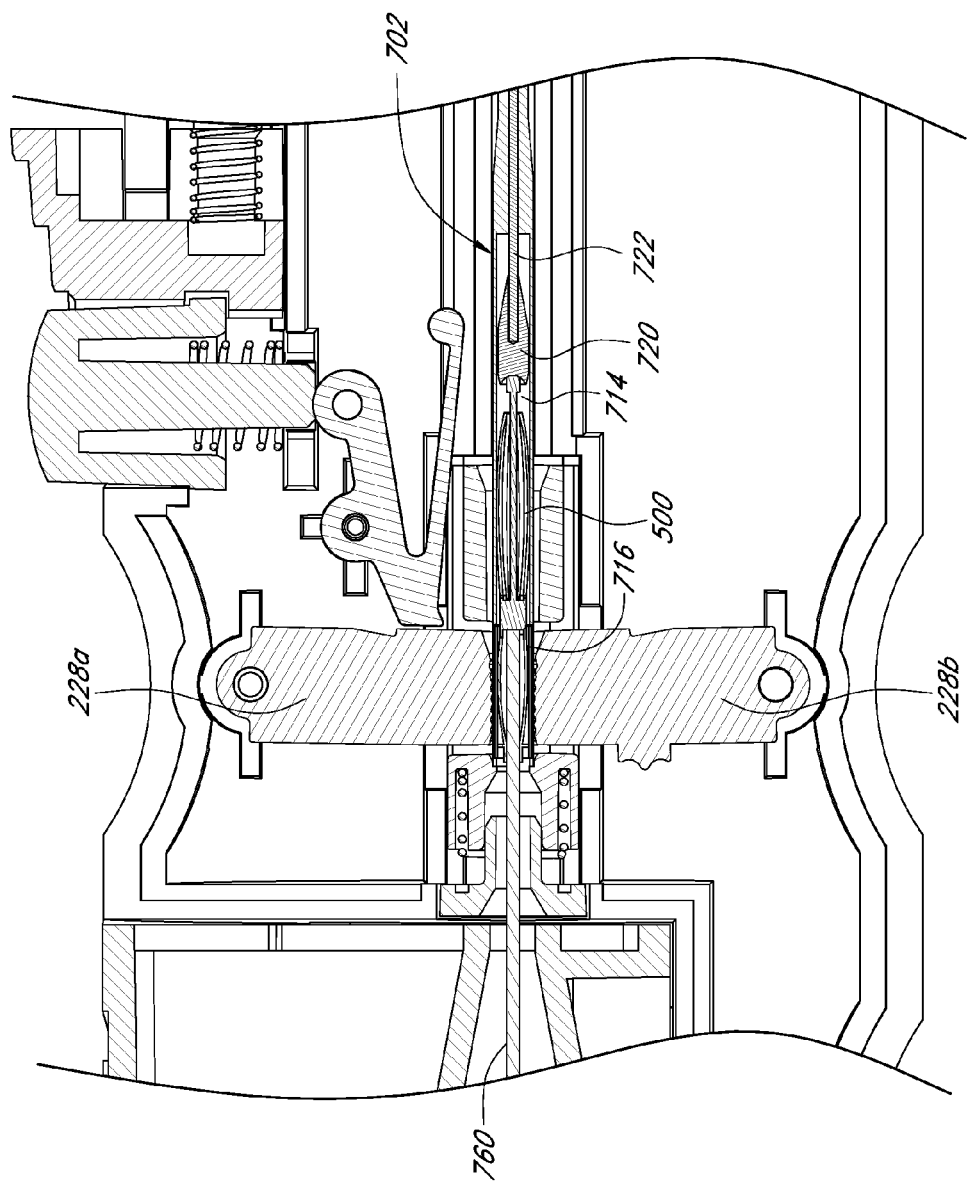
FIG. 30 is an enlarged view of the distal end of an embodiment of the deployment catheter being loaded with a device.

With reference to FIG. 30, the catheter tip 716 preferably comprises a metal tip (e.g., titanium, nitinol) and/or plastic tip (e.g., PEBAX®, ISOPLAST™ or other urethanes, PEEK, polyetherimide, polyphenylene sulfide) or other suitably rigid structure that will allow the grip pawls 228A, 228B to grip the deployment catheter 102 during loading. An insertion rod 760 may also be provided to push valve 500 past catheter tip 716 and into the cavity 714. In certain embodiments, the plastic and/or metal tip 716 is bonded to, adhered to, and/or embedded in the distal end of the deployment catheter 102. The catheter tip 716 preferably is manufactured such that compression forces or other forces, such as those encountered during loading and deployment of the catheter, do not cause appreciable deformation of the distal catheter tip. In certain embodiments, the insertion rod 760 may also comprise a low-friction material, such as PTFE coating. Such a coating, may, for example, be added on by means of a heat-shrink tubing. Coating the insertion rod 760 or manufacturing it from a low-friction material may prevent the valve 500 from being dragged out when the insertion rod 760 is withdrawn.

Referring to FIG. 29B, certain embodiments may have the catheter tip 716 located within a catheter sheath 718. In further embodiments, the catheter tip 716 can be configured to contain the anchors 502 of the medical device 500, thereby keeping the device 500 compressed within the cavity 714. The catheter tip 716 also reduces the likelihood of the device 500 (especially anchors 502) scoring the inside of the catheter cavity 714 (which may create undesirable shavings) and snagging inside the deployment catheter. Moreover, in use, some embodiments of the deployment catheter 102 are capable of multiple deployments and, therefore, the tip 716 provides an enhanced lifespan for the deployment catheter 102. Certain embodiments may also have a tip 716 with a visualization window 801 cut through it. In further embodiments, the tip 716 may have struts cut into it, providing additional flexibility to the catheter 102 when being maneuvered through a tight turn.

In certain embodiments, an inner surface of the tip 718 can be coated with a polyurethane anti-block coating to reduce friction during valve loading and deployment. In some embodiments, the inner surface of the tip 716 or the deployment catheter 102 has no coating. Instead, the inner surface of the tip 716 or the deployment catheter 102 may comprise a polytetrafluoroethylene (PTFE) liner on a portion of the end of the deployment catheter 102 and/or on the inner surface of the tip 718 and/or the tip 716 to reduce the friction between the deployment catheter 102 and the valve 500, including but not limited to any membrane material on the valve 500. In certain embodiments, the PTFE liner can be a more robust coating (e.g., a reduced wear coating).

In certain embodiments, the PTFE liner can be smooth on the inner diameter of the deployment catheter 102, which contacts the valve 500, and can be chemically etched on the outer diameter of the deployment catheter 102 to provide a rough surface for better adhesion with an outer extrusion. The PTFE liner can be very thin (e.g., approximately 0.001 inch to 0.002 inch in wall thickness). In certain embodiments, the liner can be then reflowed onto the outer extrusion of the catheter using a heat process and a sacrificial extrusion (e.g., fluorinated ethylene-propylene (FEP) or Olefin) on the outside of the outer catheter extrusion. The process can concurrently apply heat to adhere the liner to the extrusion while the sacrificial extrusion (FEP or Olefin) compresses in diameter providing force to melt the two materials together.

In certain embodiments, the deployment catheter 102 can comprise a deployment guide on the exterior of the deployment catheter. The deployment guide can be positioned or embedded at the distal end of the deployment catheter 102. The deployment guide can comprise a radiopaque material that is visible through the patient and/or the bronchoscope. The visible nature of the deployment guide allows the user to correctly position the valve at the target location.

Figure 25:
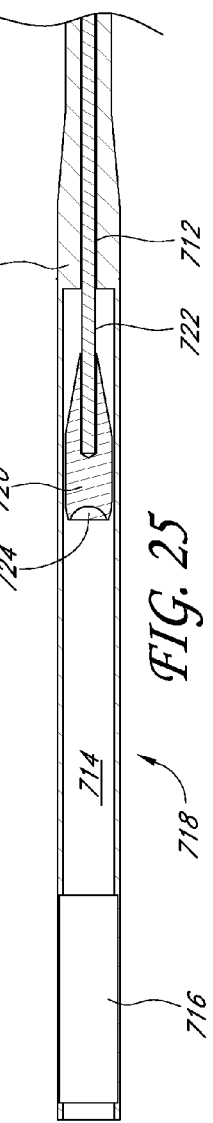
FIG. 25 is a sectioned view taken along the line 25-25 of FIG. 24 showing the distal end of the deployment catheter or other deployment apparatus of FIG. 22.

With reference to FIG. 25, the proximal end of the catheter shaft cavity 714 contains a tip 720 for a stabilization wire 722. The stabilization wire tip 720 preferably is connected or coupled to a stabilization wire 722 such that the two components move together in an axial direction relative to the catheter shaft 710. The tip 720 can have any suitable configuration but preferably comprises a recess 724 in the distal end. The recess 724 can be used to enhance control over the valve 500 during deployment.

The stabilization wire 722 extends through the lumen 712 or passageway in the catheter shaft 710. As discussed above, the lumen 712 of the catheter shaft 710 can be coated to allow the stabilization wire 724 to move more easily within the catheter shaft 710. For example, such coatings may include a PTFE liner embedded in lumen 712; such a liner may be added using any means available, such as a reflow process. Depending on the composition of the catheter shaft and/or the coating of the stabilization wire, no coating or PTFE liner may be needed. The stabilization wire 722 will move axially relative to the catheter shaft 710. More particularly, in some embodiments the stabilization wire 722 is held stationary while the catheter shaft 710 is retracted proximally. Thus, the stabilization wire 722 can be slideable within, moved through or advanced within the catheter shaft 710. The stabilization wire 722 can be a Teflon coated stainless steel coil over a stainless steel wire to allow the catheter shaft 710 to easily traverse the bronchoscope or body passageway.

In some embodiments, at the proximal end of the catheter shaft 710, there can be a reinforced shaft portion comprising a PTFE liner on the interior of the catheter shaft 710. The liner at the proximal end of the catheter shaft 710 preferably is generally thicker than at the distal end of the catheter shaft 710. The thicker liner improves pushability but decreases the bendability of the reinforced portions thus the thinner liner at the distal end enables the catheter shaft 710 to turn tighter radiuses than the proximal end.

In certain embodiments, the proximal end of the catheter shaft 710 comprises a braid that is laid between the PTFE liner and the polymer extrusion comprising, for example, PEBAX® or nylon. In some embodiments, the braid provides resistances to stretching, buckling, and/or kinking while delivering the valve or medical device 500 to the desired location. The braid preferably is located closer to the inside diameter to reduce stiffness thereby increasing flexibility of the catheter shaft 710. The braid can comprise a polymer (e.g., nylon, which can be clear and used for MRI applications), flat wire (e.g., 0.001 inch by 0.005 inch), or other like materials. In certain embodiments, the braid comprises a 60 pixs/inch configuration, wherein pixs refer to the number of open spaces in one inch.

Figure 26:
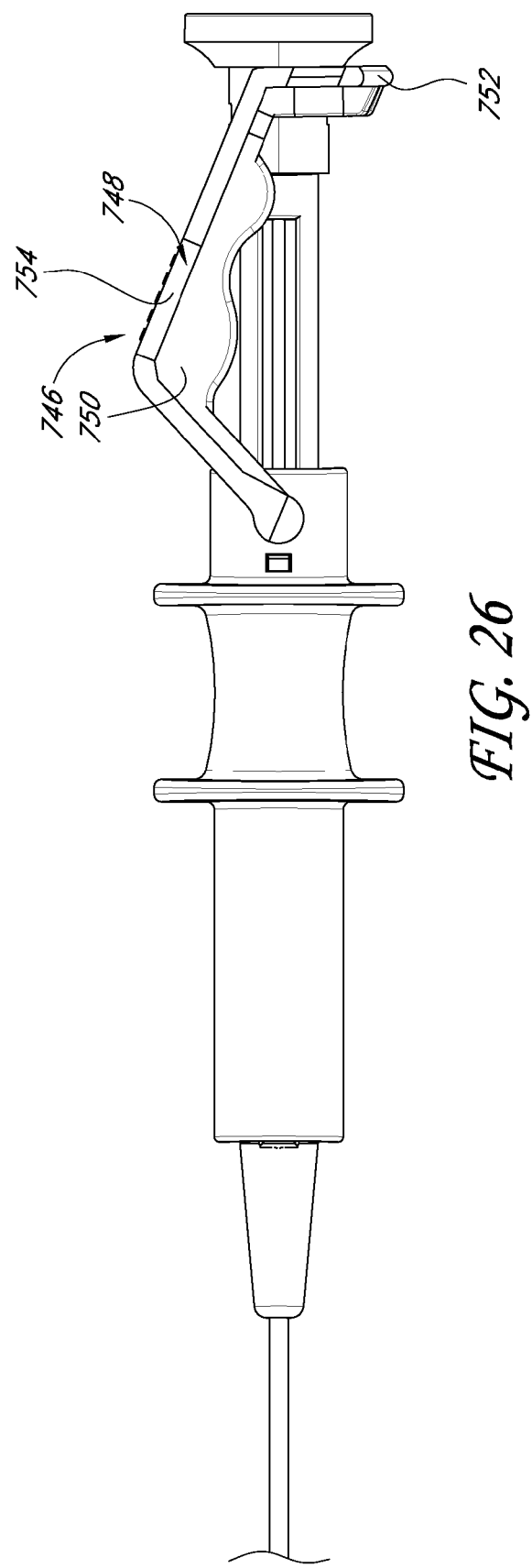
FIG. 26 is an enlarged perspective view of a control portion of the deployment catheter or other deployment apparatus of FIG. 22.
Figure 27:
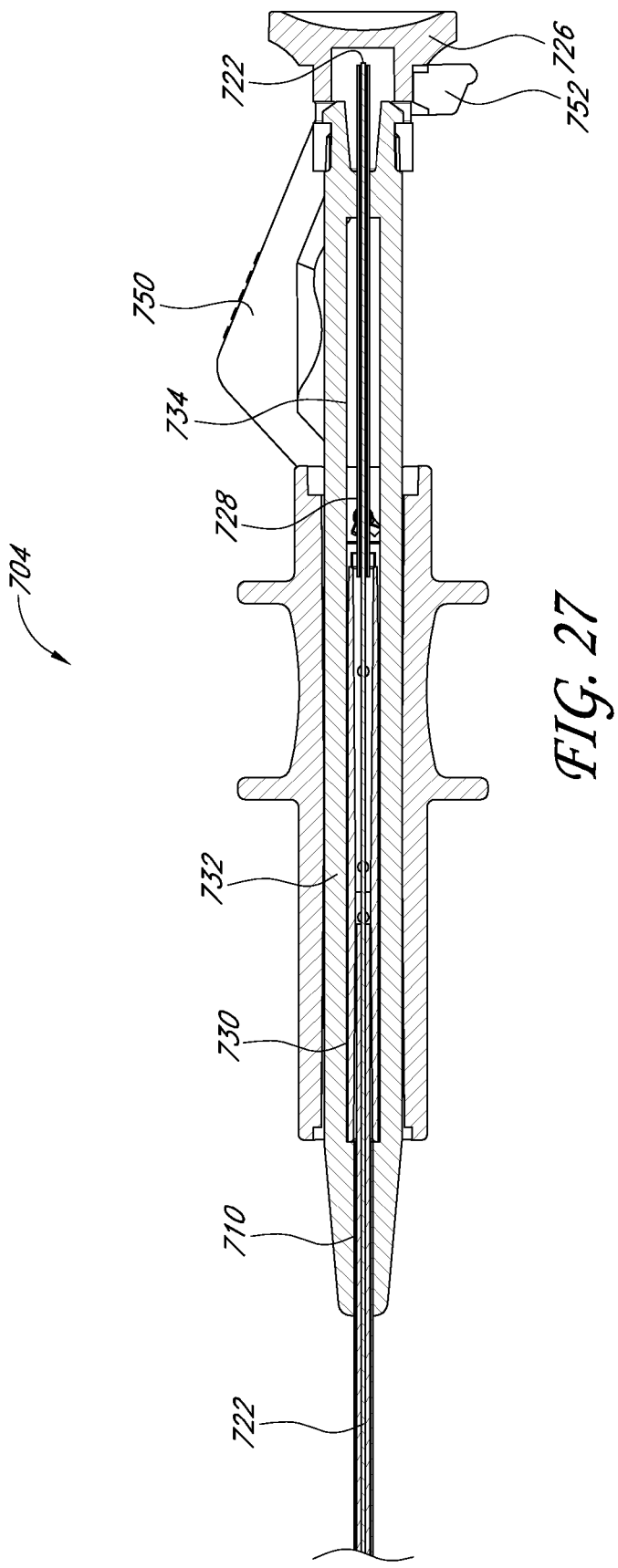
FIG. 27 is a first section taken through the deployment catheter or other deployment apparatus of FIG. 22.

With reference to FIG. 26 and FIG. 27, the stabilization wire 722, which is connected at its distal end to the stabilization wire tip 724, extends proximally to a cap 726 of control portion 704. To better illustrate this, the stabilization wire 722 has been identified at both the proximal end of the control portion 704 (i.e., at the cap 726) and at the distal end of the control portion 704. The proximal end of the stabilization wire 722 can be connected to the cap 726 in any suitable manner. In some instances, the stabilization wire 722 and the cap 726 are press fit, glued, adhered, cohered, comolded or the like.

At its proximal end, the stabilization wire 722 extends through a telescoping hypotube 728. The hypotube 728 encloses a portion of the stabilization wire 722. Thus, the hypotube 728 can provide lateral support to the stabilization wire 722 and can assist is reducing the likelihood of the stabilization wire 722 buckling, bending or overly deforming in the region of the hypotube 728. The hypotube 728 preferably connects to the cap 726 at a proximal end and abuts upon a proximal end of a sheath holder 730 at its distal end.

The distal end of the hypotube 728 nests within the sheath holder 730. Preferably, the hypotube 728 is axially moveable within the sheath holder 730. Thus, in this manner, the hypotube 728 is telescoping relative to the sheath holder 730. The sheath holder 730 extends distally of the hypotube 728 and extends over a proximal end of the catheter shaft 710. Preferably, the proximal end of the catheter shaft 710 extends into the central portion of the sheath holder 730. More preferably, the catheter shaft 710 and the sheath holder 730 are joined together for axial movement. Any suitable connection can be used.

A proximal end of a sleeve slider housing 732 snaps into the cap 726 while the distal portion of the sleeve slider housing 732 encloses the sheath holder 730. Other connections also can be used to join the sleeve slider housing 732 and the cap 726. The snap fit, however, simplifies construction and manufacturing.

The distal end of the sleeve slider housing 732 tapers toward the proximal portion of the catheter shaft 710. The sleeve slider housing 732 allows relative axial movement to occur between the sheath holder 730 and the sleeve slider housing 732. In other words, the sleeve slider housing 732 is designed to allow the sheath holder 730 to slide proximally relative to the sleeve slider housing 732 during deployment of the valve 500. The relative proximal movement results in relative movement between the catheter shaft 710, which is connected to the sheath holder 730, and the stabilization wire 722, which is connected to the sleeve slider housing 732 through the mutual connection to the cap 726.

Figure 28:
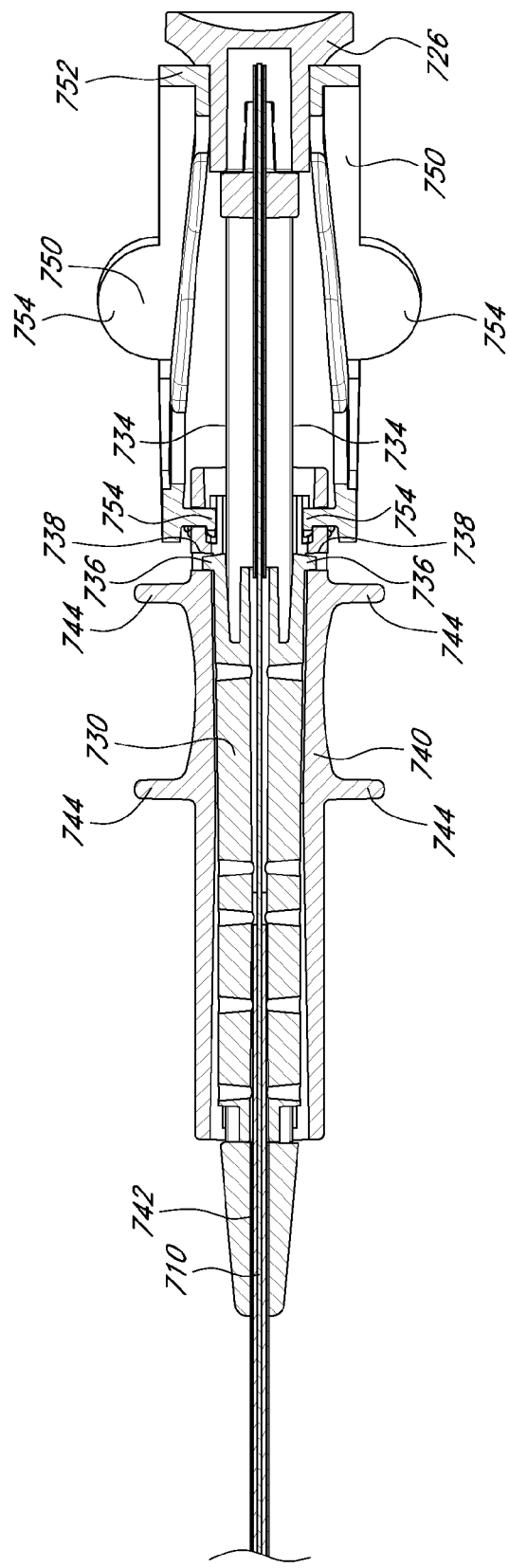
FIG. 28 is a second section taken at about ninety degrees from the first section shown in FIG. 27.

Preferably, the sleeve slider housing 732 comprises an enlarged slot or window 734. As shown in FIG. 28, the slot or window 734 accommodates two fingers 736 of the sheath holder 730. The fingers 736 engage with slots 738 formed in a sleeve slider 740. The sleeve slider 740, therefore, is joined for axial movement with the sheath holder 730 and, through the sheath holder 730, to the catheter shaft 710. Thus, any proximally-directed axial movement of the sleeve slider 740 will cause corresponding proximally-directed axial movement of the catheter shaft 710 relative to the sleeve slider housing 732 and the attached stabilization wire 722. In other words, movement of the outer sleeve slider 740 relative to the cap 726 and sleeve slider housing 732 will result in movement of the catheter shaft 710 relative to the stabilization wire 722.

A strain relief tube 742 can enclose at least a proximal portion of the catheter shaft 710. The strain relief tube 742 can extend distally from the control portion 704 to a location somewhat proximal of the distal end of the catheter shaft 710. In some configurations, the strain relief tube 742 extends between the catheter shaft 710 and the passage in the sleeve slider housing 732, relative to which the catheter shaft 710 moves. Thus, the catheter shaft 710, in some configurations, is capable of axial movement relative to the strain relief tube 742. Any suitable material can form the strain relief tube 742. In some embodiments, the strain relief tube 742 may be made from a lubricious material such as PTFE. Some embodiments may also have an outer layer made of PEBAX®.

With reference to FIG. 31A, a view of the strain relief tube 742 is presented. In certain embodiments, this strain relief tube extends over at least a portion of the catheter shaft 710, and is dimensioned to fit within the space between the outer surface of the catheter 710 and the inner surface of a bronchoscope (not shown). The strain relief tube 742 minimizes clearance between the outer diameter of the catheter shaft 710 and the inner lumen diameter of a bronchoscope working channel that the catheter is inserted into (although other types of endoscopes may be used). By minimizing clearance, more accurate positioning of a device to be delivered with the deployment catheter is possible. The clearance between the inner lumen diameter of the working channel and the outer diameter of the strain relief tube 742 can be as small as possible while still permitting insertion into and axial movement within the bronchoscope working channel. In certain embodiments, the clearance between the bronchoscope inner lumen diameter and the strain relief tube 742 outer diameter may be as low as about 0.5%, although values of about 3% still permit relatively accurate device delivery. Similarly, and as depicted in FIG. 31A, the clearance between the outer diameter of catheter 710 and the inner diameter of strain relief tube 742 can be minimized in consideration of the factors discussed above. In certain embodiments, the clearance between these two diameters may be as low as about 1.8%, although values of about 5.1% still permit relatively accurate device delivery. While the strain relief tube 742 does not usually extend over the distal tip 702, minimization of clearances between the distal tip and the inner lumen of a bronchoscope working channel helps to maintain placement accuracy of the device being delivered through the catheter. In certain embodiments, the clearance between the distal tip 702 and the bronchoscope working channel inner lumen diameter may be as low as about 0.7%, although values of about 2.5% still permit relatively accurate device delivery. The clearance between the outer diameter of stabilization wire 722 and the inner diameter of catheter 710 may also be minimized in consideration of the factors discussed above. In certain embodiments, the clearance between these two diameters may be as low as about 4.2%, although values of 11.3% still permit relatively accurate device delivery.

Holes 821 may also be provided through the strain relief tube 742 and/or the catheter shaft 710. In some embodiments, these holes may be used during sterilization procedures, for example sterilization procedures employing sterilization fluids, including gases such as ethylene oxide. These holes permit a sterilizing gas to pass into the body of the catheter and other interstitial spaces. In certain embodiments, the diameter of the holes 821 may be tailored to effectuate an appropriate pressure difference between the interstitial spaces present in the catheter 102 and the flow rate of sterilizing gas. In certain embodiments, the holes 821 only extend to the center of the strain relief tube 742 and/or the catheter shaft 710, without passing completely through the strain relief tube 742 and/or the catheter shaft 710. Preferably, the holes 821 in the catheter shaft 710 and the holes 821 in the strain relief tube 742 are staggered, thus ensuring that sterilizing gas may pass through a larger area of the interstitial space between the strain relief tube 742 and the catheter shaft 710. In certain embodiments, the diameter of the holes 821 in the catheter shaft 710 are preferably 0.01", although holes 821 measuring from 0.008" to 0.012" were found to function acceptably. In certain embodiments, the diameter of the holes 821 in the strain relief tube 742 are preferably 0.020", although holes 821 measuring from 0.018" to 0.025" were found to function acceptably. In an embodiment of a catheter adapted to fit in a 2.0 mm bronchoscope with holes measuring 0.01", the flow rate was measured to be 0.03 SLPM with 6 psi of pressure difference of nitrogen oxide gas, and 0.06 SLPM with 10 psi of pressure difference. This flow rate compares favorably to the same catheter with no holes, where no measurable flow rate was found with up to 20 psi of pressure difference. Some embodiments may not require holes 821 if the flow rate is adequate to ensure acceptable sterilization. A catheter adapted to fit in a 2.6 mm bronchoscope was measured to have a flow rate of 0.04 SLPM at 6 psi of pressure difference, and 0.09 SLPM at 10 psi of pressure difference while having no holes. A person of ordinary skill in the art will optimize the hole diameter depending upon the particular catheter size and sterilization protocol used to achieve a sufficient flow rate of sterilizing fluid.

FIGS. 31B-D depict cross sections taken along various parts of the catheter 102 depicted in FIG. 31A. The apparent size of the cross sections may not be to scale. FIG. 31B depicts a cross section through the strain relief tube 742, the catheter shaft 710, and the stabilization wire 722. In certain embodiments, the catheter 710 may be composed of a first layer 822, which can consist of a lubricious material such as PTFE. In certain embodiments, this first layer 822 may have a thickness of 0.001". A braid 823 is then overlaid over the layer 822, and a third layer 824, which can consist of PEBAX® or other material with similar properties is overlaid. In certain embodiments, the braid 823 may be composed of stainless steel wire. The braid 823 may also have a thickness of 0.001". In certain embodiments, the layer 824 may have a thickness of 0.014". This assembly is heated, causing softening or at least partial melting of the layer 824 into the braid 823. The braid 823 is typically formed of a flexible material which does not deform substantially when stretched; it may be formed from a suitable metal such as stainless steel, for example but without limitation. The braid 823 serves to prevent stretching and kinking of the catheter 710, while increasing flexibility. An optional fourth layer 825 may also be added either before the heating step or subsequently. This fourth layer 825 may consist of fluorinated ethylene propylene (FEP), or any suitable material. This fourth layer 825 may be lubricious, and may be added to the assembled catheter 710 by means of heat-shrink tubing.

FIG. 31C shows a cross-section of the catheter 710 near the distal end 702. Here, the stabilization wire tip 720 which contacts a medical device inserted into the catheter cavity 714 is now visible. The strain relief tube 742 is not typically disposed over the distal end 702, and as such, is not illustrated here. Near the distal end 702, the catheter 710 may be composed of a first layer 822, usually of the same composition as described above. In certain embodiments, coils 826 may be provided instead of a braid 823, and these coils 826 may then be overlaid over the layer 822. Coils 826 provide additional resistance to kinking of the catheter when manipulated during operation. During manufacturing, the portion of the catheter 710 with coils 826 may be overlaid partially with the more proximal portion of the catheter 710 with braids 823. A third layer 824, which can which can consist of PEBAX® or other material with similar properties, may be overlaid on top of the coils 826. This assembly may then be heated, causing softening or at least partial melting of the layer 824 into the coils 826. A fourth layer 825, described above, is optionally present. The third layer and fourth layers 824 and 825 are optionally constructed of a different material nearer the distal end than what is used at the proximal end. For example, the layer 824 may be constructed of a material that is at least partially transparent, so as to form a visualization window 801. Other possibilities, such as modifying material thicknesses or other physical parameters, are also possible.

FIG. 31D shows a cross section of catheter 710 at the most distal end, through tip 716. Valve 500 is positioned within cavity 714, and is contained by tip 716. Preferably, the extreme distal end of the tip 716 extends beyond the valve 500 and forms an atraumatic tip structure. Outer sheath 718 is usually composed of the same material as the third layer 824 or the optional fourth layer 825. Tip 716 may be bonded to sheath 718 by any means, including gluing or melting of the layer 718 around tip 716. To provide a simplified structure resulting in the visualization window 801 described above, the tip 716 can be spaced from and not directly connected with the coils 826. Thus, the tip 716 may be joined to the coils 826 with the outer sheath 718, which may be constructed from polymeric materials such as PEBAX®, for example.

Figure 33A:
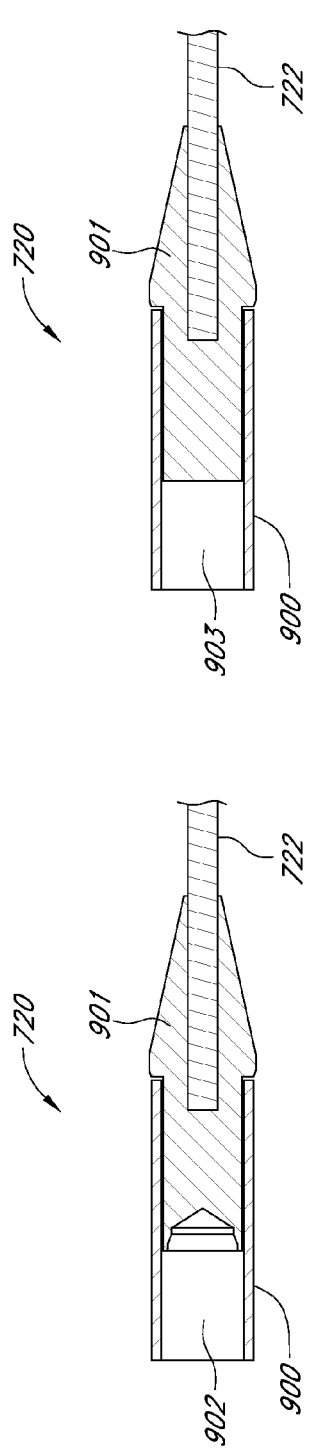
FIGS. 33A-E are enlarged views depicting embodiments of the stabilization wire tip 720.
Figure 33B:
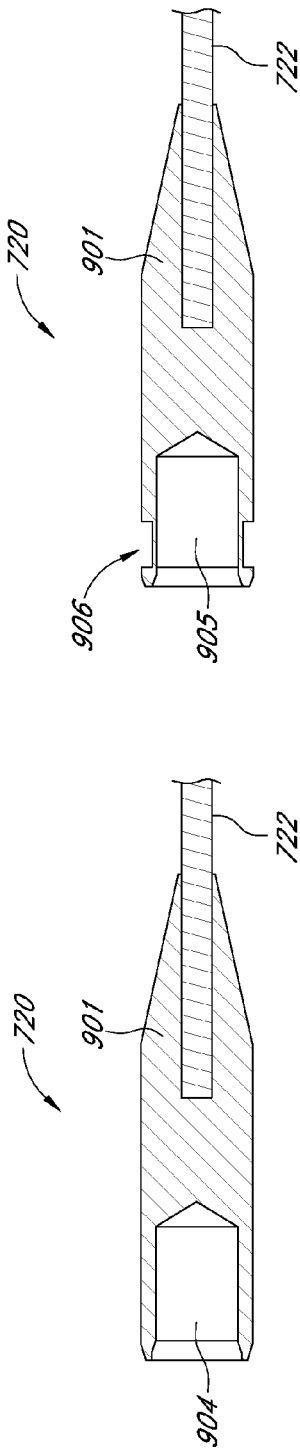
Figure 33C:
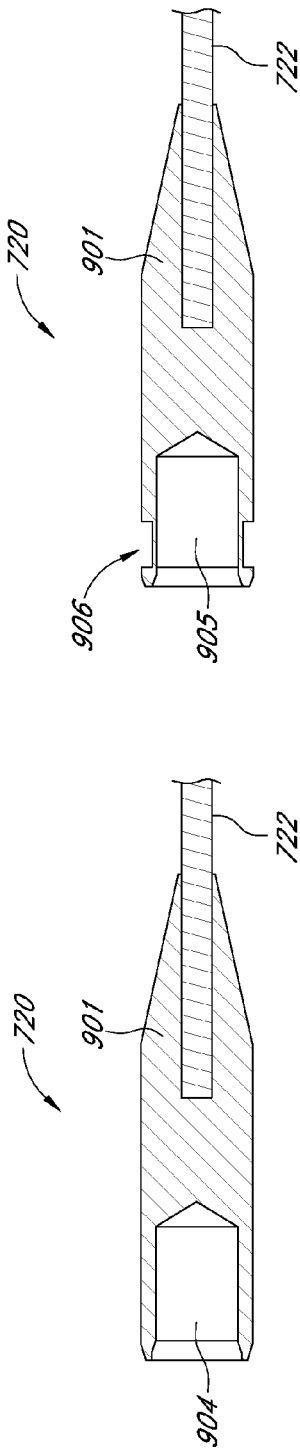
Figure 33D:

FIGS. 33A-E show various embodiments of the stabilization wire tip 720. In certain embodiments, the stabilization wire tip 720 may be of a two-part construction comprising a cone 901 and a sleeve 900, as shown in FIG. 33A. The cone 901 is inserted over the stabilization wire 722. The cone 901 may be constructed from a rigid material, including metal and/or plastic. A sleeve 900 may be affixed to the cone 901. There may also be provided a cavity 902 capable of accepting at least part of a medical device, such as a valve 500. In certain embodiments, the sleeve 900 may extend to the tip of the cup portion of a valve 500. In a preferred embodiment, the sleeve 900 extends past the tip of the cup portion of a valve 500 to its apex. FIG. 33C depicts an embodiment of the stabilization wire tip 720 manufactured as a single piece, with the cone 901 also possessing a sleeve capable of receiving at least part of a medical device, such as a valve 500. FIG. 33B shows a stabilization wire tip 720 possessing a cavity 903 with a flat end. The cavity 903 with a flat end is not necessarily limited to two-part stabilization wire tip embodiments of the type depicted in FIG. 33B. A cavity 903 with a flat end may also be provided with a one-piece stabilization wire tip design of the type depicted in FIG. 33C. Depending on the medical device accepted into the cavity 903, such a flat end may prevent such a medical device from snagging or becoming stuck within the cavity when deployed. Of course, cavities with different ends, such as those shown in the other illustrations are possible. In some embodiments, the ends of the cavities may be conical (for example the cavities 902, 904, 905). FIGS. 33C-D also depict non-limiting embodiments of the stabilization wire tip 720 possessing chamfered or beveled edges at the entrance of the cavity 903. Such edges may aid in preventing the stabilization wire tip 720 from snagging or catching on various internal portions of the catheter 710, including the catheter sheath 718 or the distal tip 716, as well as any device inserted into it, such as a valve 500.

Figure 33E:
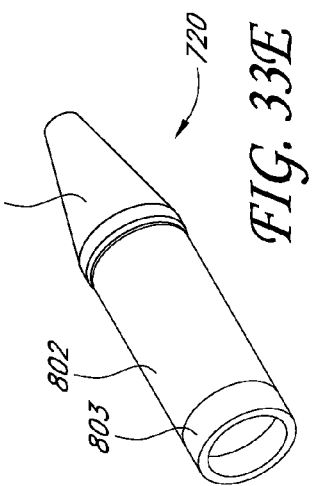

Also, and as shown in FIG. 33E, sleeve 900 may comprise locator markings 802 and 803 disposed upon it. With reference to FIG. 33D, certain embodiments may provide a recess 905, which may for example be machined out or molded from the cone tip 901. Such a recess 906 may be used to place one or more locator markings 802 and/or 803 onto the cone tip 901, for example by means of a heat shrink tubing. In some embodiments, the recess 906 may also be widened to permit placement of one or more wider locator markings. In embodiments of the stabilization wire tip 720 possessing lines 802 and/or 803, the catheter sheath 718 is translucent or preferably transparent on at least the portion of the sheath 718 that lies above the stabilization wire tip 720, such that an an operator may visualize these lines. In a preferred embodiment, the sleeve 900 extends to the apex of a valve 500, and has at least one marking (e.g., line 803) disposed near this apex Referring to FIG. 28, the control portion 704 can be constructed of plastic, metal, or other suitable materials. Preferably, the sleeve slider 740 is a plastic molded piece. Accordingly, formation of ribs 744 that define finger holds can be relatively cost effective and simple. Other configurations also are possible.

As explained above, movement of the sleeve slider 740 toward to the cap 726 can cause deployment movement through retracting the catheter shaft 710 relative to the stabilization wire tip 720, which pushes the valve 500 out of the catheter tip 716 of the catheter shaft 710. Thus, in some embodiments, a locking feature 746 is desired that can reduce or eliminate the likelihood of inadvertent deployment of the valve 500 from the catheter tip 716.

The illustrated locking feature 746 comprises at least one member that extends between the cap 726 and the sleeve slider 740. By extending between at least these two components, the locking feature 746 can reduce the likelihood of inadvertent relative movement between the catheter shaft 710 and the stabilization wire tip 720. Of course, it is possible to configure another locking feature between the catheter shaft 710 and the stabilization wire tip 720 in other manners by connecting either directly or indirectly to the catheter shaft 710 and the stabilization wire.

With reference to FIG. 26, the locking feature 746 comprises a yoke shaped lock lever 748. The lever 748 comprises two legs 750 that connect together at a partial collar 752. The legs 750 each have a peg 754 that snaps into an opening in the sleeve slider 740. The pegs 754 can pivot relative to the sleeve slider 740 such that the legs 750, and therefore the lever 748 as a whole, can pivot relative to the sleeve slider 740.

As discussed above, the lever 748 comprises the partial collar 752. The partial collar can extend about half way around a lower portion of the cap 726. The degree to which the cap 726 is encircled can vary depending upon the application but the partial collar 752 preferably extends slightly more than 180 degrees around the cap 726. Other configurations are possible.

The legs 750 are bowed in a direction opposite of the partial collar 752. The bowing of the legs 750 enables easy manipulation with a single hand by a user. In other words, the bowed legs 750 create a pair of manipulating locations 754, which are further enhanced with large pads, to facilitate easy disengagement of the collar 752 from the cap 726. Once the collar 752 is disengaged from the cap 726, the lever 748 can be moved out of the way and the sleeve slider 740 can be pulled upward toward the cap 726 such that the valve 500 can be deployed. With reference again to FIG. 1, the shipping lock 114 is a generally cylindrical tube in certain embodiments, and can comprise an internal lumen. The shipping lock 114 can generally comprise a similar shape and dimension to that of the catheter shaft 710 of the deployment catheter 102. The shipping lock 114 can be configured to be positioned into the second open cavity 218 of the housing structure 202 when the valve loader 106 is being shipped or stored for future use. In one embodiment, the shipping lock 114 can be inserted into the second open cavity 214 of the housing structure 202 and into the alignment tube 226, wherein the alignment tube 226 grips and/or locks the shipping lock 114 into the alignment tube 226 in a similar to way the deployment catheter 102 can be locked in the alignment tube 226.

In certain embodiments, the loader plunger 220 can be positioned or pushed into the housing structure 202, and through the first open cavity 214 of the housing structure 202, and into the inner lumen of the shipping lock 114. With the distal end of the loader plunger 220 telescoped, nested and/or positioned in the inner lumen of the shipping lock 126, the loader plunger 220 can be generally stabilized during shipping and storage, and the loader plunger 220 can be generally prevented from vibrating or moving laterally or otherwise within the alignment tube 226 during shipping and/or storage. With the loader plunger 220 substantially positioned within the housing structure 202, the loader plunger 220 is protected from breakage during shipping and storage of the valve loader 106. By inserting the shipping lock 114 into the alignment tube 226, the grip pawls 228A, 228B are put under tension, stress, and/or strain, which substantially prevents the leaf spring 306 from becoming disengaged or decoupled from the first grip pawl 228A. In removing the shipping lock 114, the grip pawls 228A, 228B advantageously return to their default position and can be configured to receive the deployment catheter 102.

In certain embodiments, the valve loading system 100 is a kit for storage, transport, and/or loading that comprises a deployment catheter 102, at least one cartridge 104 that comprises a valve 500, and a valve loader 106. In certain embodiments, the cartridges 104 are individually packaged sterilized cartridges 104 for single use and/or to be disposable. In certain embodiments, the kit and/or components are treated with ethylene oxide to make sterile for single patient use or to be disposable. In certain embodiments, the cartridge, the valve loader, the kit and/or other components are configured to be sterilized or treated for multiple use.

Methods of Use

A method of using the valve loading system 100 may be described in connection with the figures. However, it will be appreciated that the various surgical procedures (for example, lung valve implantation procedures, stent implantation procedures, or the like) that may use the valve loading system 100 may vary from one procedure to the next, depending on the specific purpose and/or technique of the procedure. Accordingly the following description is intended to be generally illustrative only and not limiting as to the present method.

As noted above, a user obtains the valve loading system 100. In some configurations, the valve loading system 100 can be obtained from a sterile single patient use kit that comprises, among other things, a deployment catheter 102, at least one cartridge 104 that comprises a valve 500, and a valve loader 106. The user may slide or move the safety slide mechanism 326 toward the distal end of the housing structure 202 to unlock or allow the button 314 to be depressed into the housing structure 202. By depressing the button 314 into the housing structure 202, the shipping lock 114 can be unlocked and the user can remove the shipping lock 126 from the second open cavity 218. After removing the shipping lock 114, the user may release the button 314 and the safety slide mechanism 326. In some configurations, simply depressing the button 314 causes the shipping lock 114 to be released and, therefore, the button 314 can be released before the shipping lock 114 is removed. The distal end of the deployment catheter 102 then can be inserted into the second open cavity 218. The user can insert the deployment catheter 102 into the second open cavity 218 until the user hears a click sound or other audible sound, which indicates to the user that the deployment catheter 102 has been locked into the housing structure 202 and has been properly positioned within the alignment tube 226. In certain embodiments, the visualization window 801 is provided at the distal tip of the catheter, permitting visual confirmation that a medical device (e.g., valve 500) is properly loaded into the distal tip of the deployment catheter 102.

In certain embodiments, the user may retract, slide back, or move the loader plunger 220 from within the housing structure 202, thereby moving the arm, bracket, or bar of the second end 250 of the cartridge locking mechanism 222 from the first open cavity 214. The user may select a desired cartridge 104 containing the appropriate size, shape, and/or type valve or medical device 500. In certain embodiments, the user may proper align the cartridge 104 with the first open cavity 214 in order to insert the cartridge 104 into the first open cavity 214. After the cartridge 104 has been fully inserted into the first open cavity 214, the user may push, slide, or move the loader plunger 220 into the housing structure 202, thereby allowing a bayonet end of the loader plunger 220 to contact the valve or medical device 500 within the cartridge 104.

As the plunger 220 contacts and pushes the valve or medical device 500 toward the distal end of the cartridge 104 and through the tapered or funnel portion of the cartridge 104, the valve or medical device 500 becomes compressed. With the valve or medical device 500 compressed, the user can continue to push the loader plunger 220 into the housing structure 202, thereby pushing the compressed valve or medical device 500 through the alignment insert 224 and the alignment tube 226, and into the distal end of the deployment catheter 102. With the deployment catheter 102 loaded with the valve or medical device. 500, the user may slide or move the safety slide mechanism 326 toward the distal end of the housing structure 202, to unlock or allow the button 314 to be depressed into the housing structure 202.

In depressing the button 314 into the housing structure 202, the deployment catheter 102 can be unlocked, and the user can remove the deployment catheter 102 from the second open cavity 218. In certain embodiments, the user can position the loaded deployment catheter 102 into the body of the patient at the desired location in order to implant the valve or medical device 500 in the patient. In certain embodiments, the deployment catheter 102 is advanced through a channel of a bronchoscope and navigated to the target implant location. In certain embodiments, the valve or medical device 500 (e.g., comprising radiopaque material) is visible through the deployment catheter 102 to allow the user to correctly position the valve at the target location. In certain embodiments, the user can use the deployment guide, which can comprise a radiopaque material that is visible through the body, to allow the user to correctly position the valve the target location.

To deploy the valve or medical device 500, the user, in certain embodiments, unlatches, turns, or swings the locking feature 746 to disengage the locking feature 746 from the cap 726. The user can actuate control portion 704 to cause the catheter sheath 710 to retract relative to the stabilization wire 722 to release the valve or medical device 500. The position of the valve or medical device 500 is stabilized at the target location during deployment with the stabilization wire 722.

In certain embodiments, after the valve or medical device 500 has been deployed, the deployment catheter 102 can be retrieved from the body of the patient, and be reloaded with another valve or medical device 500 using the foregoing process. With the foregoing process, the deployment catheter 102 can be reloaded with different valves or medical devices 500 having different shapes, sizes, and/or types. The foregoing process also allows the valve or medical device 500 to remain in a default configuration, as opposed to a substantially compressed or stressed configuration, thereby reducing the possible failure, wear, and/or deterioration of the valve or medical device 500. In other words, the cartridge 104 stores the valve or medical device 500 in a non-compressed state, which reduces wear and tear on the medical device 500 and reduces the likelihood of an adverse clinical event relating to the materials or structure of the medical device 500.

Figure 32C:
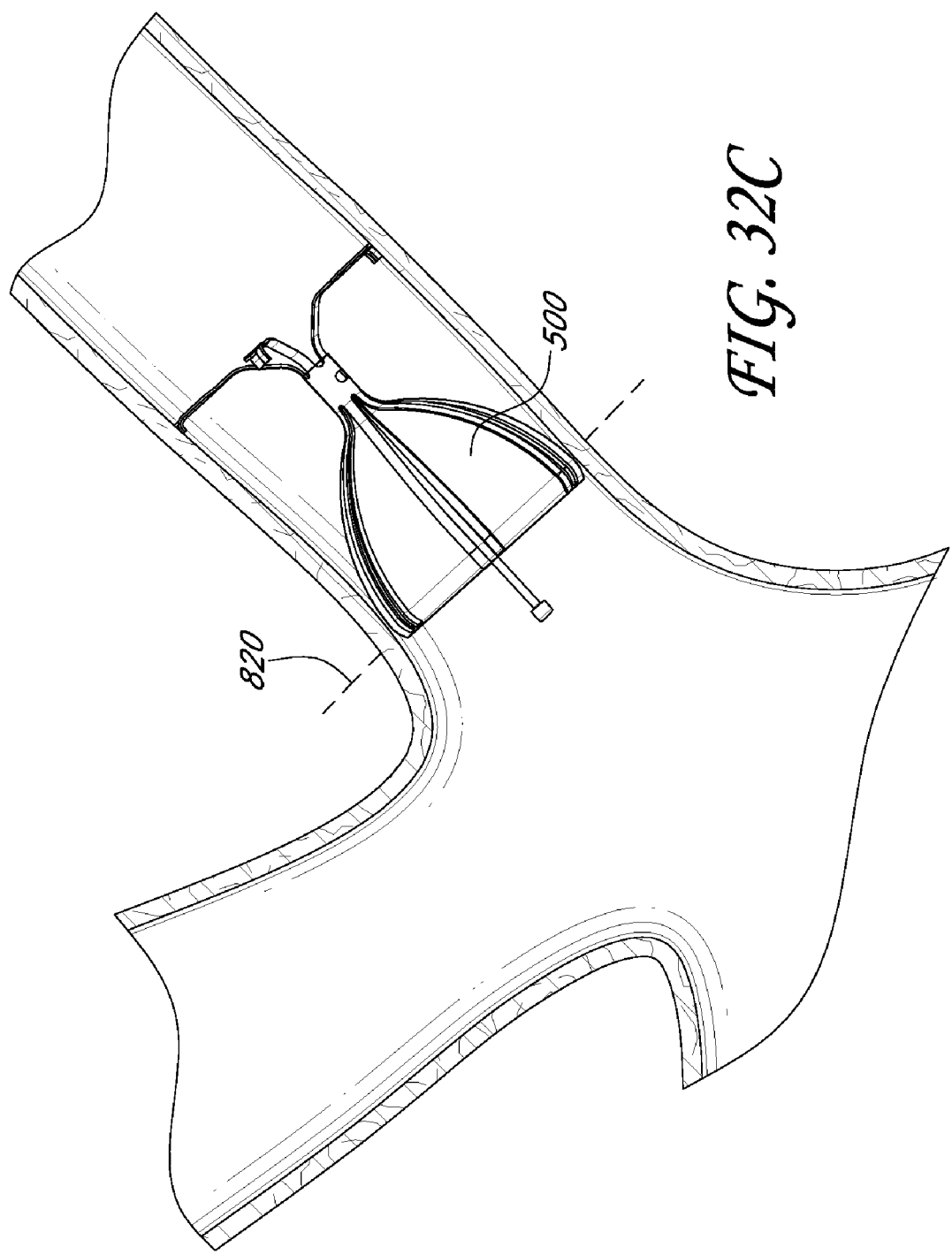

FIGS. 32 A-C shows an embodiment of catheter 201 with a valve 500 loaded within it. A deployment catheter 102 is inserted into a bronchoscope (not shown), and the bronchoscope is guided to a portion of a lung requiring treatment. In determining an appropriate deployment site for the valve 500 (here, denoted as deployment site 820), an operator may use the yellow line 803 to align the catheter with the site where the valve will be deployed, as the valve 500 will be released from the distal end of the catheter at the approximate location denoted by the yellow line. In some embodiments, the line 803 generally aligns with an air passageway region that the membrane of the valve 500 will seal. The black bands 802 provide additional contrast so that the operator can easily see the line 803 through a bronchoscope viewing port. Moreover, an operator can extend the catheter distally beyond the visualization of the black bands and then retract the catheter proximally. While retracting the first black band 802 encountered can be used as a landmark indicating that the line 803 is approaching. With the line 803 aligned with the deployment site 820, the operator depresses the plunger 220 (shown in FIG. 1), thereby retracting catheter sheath 710 while the stabilization wire 722 remains generally stationary. The stabilization wire tip 720 at the end of the stabilization wire 722 contacts the central rod 821 of valve 500 within recess 724, thereby maintaining valve 500 in substantially the same position while the sheath 710 is retracted. Freed from the catheter, the anchors expand into contact with the air passageway wall and the valve 500 expands so that the apex of its cup portion makes contact with the lung walls generally at the site 820 selected along the lung passageway wall.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

What is claimed is:

1. A deployment catheter system for the deployment of a medical device, the deployment catheter system comprising:
   a catheter shaft comprising a proximal end and a distal end;
   a cavity inside a distal portion of the catheter shaft adapted to receive a medical device;
   a locator marking disposed along the distal portion of the catheter shaft, the locator marking being viewable from an outside of the catheter shaft, and the locator marking corresponding to an approximate deployment site of the medical device disposed within the catheter shaft;
   a rigid tip disposed at a distal end of the cavity inside the catheter shaft, the rigid tip able to accommodate at least a portion of the medical device loaded therein; and
   an at least partially transparent segment disposed between the locator marking and the rigid tip, the at least partially transparent segment permitting visualization of at least a portion of the cavity near the distal end of the catheter shaft;
   wherein the locator marking comprises one or more pigmented bands;
   wherein the pigmented bands comprise a yellow pigmented band with two black pigmented bands disposed on either side of the yellow pigmented band;
   wherein the medical device is a valve,
   wherein the catheter shaft further comprises a strain relief tube extending over at least a proximal portion of the catheter shaft,
   wherein a thickness of the strain relief tube is adapted to fill substantially all of the distance between an outer surface of the catheter shaft and an inner surface of a bronchoscope into which the catheter shaft is inserted.

2. The catheter system of claim 1, wherein the catheter shaft further comprises a stabilization wire extending within the catheter shaft.

3. The catheter system of claim 2, wherein the catheter shaft retracts relative to the stabilization wire during deployment of the medical device.

4. The catheter system of claim 1, wherein the strain relief tube comprises a lubricious material.

5. The catheter system of claim 4, wherein the lubricious material is polytetrafluoroethylene.

6. The catheter system of claim 1, wherein the catheter shaft is disposed within a working channel of the bronchoscope and wherein the bronchoscope is a 2.0 mm bronchoscope.

7. The catheter system of claim 1, wherein the catheter shaft is disposed within a working channel of the bronchoscope and wherein the bronchoscope is a 2.6 mm bronchoscope.

8. The catheter system of claim 1, wherein a clearance between an outer surface of the strain relief tube and an inner lumen surface of the bronchoscope is between 0.5% and 3%.

9. The catheter system of claim 1, wherein a clearance between an inner surface of the strain relief tube and an outer surface of the catheter shaft is between 1.8% to 5.1%.

10. The catheter system of claim 1, wherein the distal portion of the catheter shaft further comprises at least a segment of coils.

* * * * *

UNITED STATES PATENT AND TRADEMARK OFFICE
CERTIFICATE OF CORRECTION

PATENT NO. : 8,043,301 B2
APPLICATION NO. : 12/422179
DATED : October 25, 2011
INVENTOR(S) : Adams et al.

It is certified that error appears in the above-identified patent and that said Letters Patent is hereby corrected as shown below:

On the Title page:

At (Item 56) Page 5, Col. 2, line 3, Under Other Publications, change "Nvel" to --Novel--.

At (Item 56) Page 5, Col. 2, line 6, Under Other Publications, change "Certamics" to --Ceramics--.

At (Item 56) Page 5, Col. 2, line 16, Under Other Publications, change "Asthatic" to --Asthmatic--.

At (Item 56) Page 5, Col. 2, line 16, Under Other Publications, change "Interatracheal" to --Intratracheal--.

At (Item 56) Page 5, Col. 2, line 19, Under Other Publications, change "Sucessfully" to --Successfully--.

At (Item 56) Page 5, Col. 2, line 25, Under Other Publications, change "Cyanocrylate" to --Cyanoacrylate--.

At (Item 56) Page 5, Col. 2, line 48, Under Other Publications, change "Thorascostomy;" to --Thoracostomy;--.

At (Item 56) Page 5, Col. 2, line 48, Under Other Publications, change "mmanual;" to --manual;--.

At Column 4, line 11, Change "FIGS" to --FIGS.--.

At Column 21, line 45, After "that" delete "an".

At Column 21, line 49, After "apex" insert --.--.

At Column 22, line 42, Change "to way" to --way to--.

At Column 24, line 5, Change "device." to --device--.

Signed and Sealed this
Thirty-first Day of July, 2012

David J. Kappos
*Director of the United States Patent and Trademark Office*